US011939631B2

United States Patent
Ju et al.

(10) Patent No.: US 11,939,631 B2
(45) Date of Patent: *Mar. 26, 2024

(54) FOUR-COLOR DNA SEQUENCING BY SYNTHESIS USING CLEAVABLE FLUORESCENT NUCLEOTIDE REVERSIBLE TERMINATORS

(71) Applicant: The Trustees of Columbia University in the City of New York, New York, NY (US)

(72) Inventors: Jingyue Ju, Englewood Cliffs, NJ (US); Dae Hyun Kim, Northbrook, IL (US); Lanrong Bi, Hancock, MI (US); Qinglin Meng, Foster City, CA (US); Xiaoxu Li, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 203 days.

This patent is subject to a terminal disclaimer.

(21) Appl. No.: 17/405,341

(22) Filed: Aug. 18, 2021

(65) Prior Publication Data

US 2021/0381043 A1    Dec. 9, 2021

Related U.S. Application Data

(63) Continuation of application No. 16/722,702, filed on Dec. 20, 2019, now Pat. No. 11,098,353, which is a continuation of application No. 15/988,321, filed on May 24, 2018, now abandoned, which is a continuation of application No. 15/354,531, filed on Nov. 17, 2016, now Pat. No. 10,000,801, which is a continuation of application No. 14/242,487, filed on Apr. 1, 2014, now Pat. No. 9,528,151, which is a continuation of application No. 13/665,588, filed on Oct. 31, 2012, now abandoned, which is a continuation of application No. 13/023,283, filed on Feb. 8, 2011, now Pat. No. 8,298,792, which is a continuation of application No. 12/312,903, filed as application No. PCT/US2007/024646 on Nov. 30, 2007, now Pat. No. 7,883,869.

(60) Provisional application No. 60/872,240, filed on Dec. 1, 2006.

(51) Int. Cl.
C12Q 1/68 (2018.01)
C12Q 1/6823 (2018.01)
C12Q 1/6869 (2018.01)

(52) U.S. Cl.
CPC ......... *C12Q 1/6869* (2013.01); *C12Q 1/6823* (2013.01)

(58) Field of Classification Search
CPC ..................... C12Q 1/6869; C12Q 1/6823
See application file for complete search history.

(56) References Cited

U.S. PATENT DOCUMENTS

| | | |
|---|---|---|
| 4,711,955 A | 12/1987 | Ward et al. |
| 4,772,691 A | 9/1988 | Herman |
| 4,804,748 A | 2/1989 | Seela |
| 4,824,775 A | 4/1989 | Dattagupta |
| 4,863,849 A | 9/1989 | Melamede |
| 4,888,274 A | 12/1989 | Radding et al. |
| 5,043,272 A | 8/1991 | Hartley |
| 5,047,519 A | 9/1991 | Hobbs, Jr. et al. |
| 5,118,605 A | 6/1992 | Urdea |
| 5,151,507 A | 9/1992 | Hobbs, Jr. et al. |
| 5,174,962 A | 12/1992 | Brennan |
| 5,175,269 A | 12/1992 | Stavrianopoulos |
| 5,242,796 A | 9/1993 | Prober et al. |
| 5,302,509 A | 4/1994 | Cheeseman |
| 5,308,990 A | 5/1994 | Takahashi |
| 5,328,824 A | 7/1994 | Ward et al. |
| 5,332,666 A | 7/1994 | Prober et al. |
| 5,383,858 A | 1/1995 | Reilly et al. |
| 5,436,143 A | 7/1995 | Hyman |
| 5,437,975 A | 8/1995 | McClelland et al. |
| 5,449,767 A | 9/1995 | Ward et al. |
| 5,476,928 A | 12/1995 | Ward et al. |
| 5,516,664 A | 5/1996 | Hyman |
| 5,534,424 A | 7/1996 | Uhlen |
| 5,547,839 A | 8/1996 | Dower |
| 5,547,859 A | 8/1996 | Goodman |
| 5,556,748 A | 9/1996 | Douglas |
| 5,599,675 A | 2/1997 | Brenner |
| 5,602,000 A | 2/1997 | Hyman |
| 5,637,469 A | 6/1997 | Wilding et al. |
| 5,654,419 A | 8/1997 | Mathies |
| 5,658,736 A | 8/1997 | Wong |
| 5,709,999 A | 1/1998 | Shattuck et al. |
| 5,728,528 A | 3/1998 | Mathies |
| 5,763,594 A | 6/1998 | Hiatt et al. |
| 5,770,365 A | 6/1998 | Lane et al. |

(Continued)

FOREIGN PATENT DOCUMENTS

| | | |
|---|---|---|
| CA | 2425112 | 9/2011 |
| DE | 4141178 | 6/1993 |

(Continued)

OTHER PUBLICATIONS

U.S. Appl. No. 09/266,187, filed Mar. 10, 1999, Stemple et al.

(Continued)

*Primary Examiner* — Jezia Riley

(74) *Attorney, Agent, or Firm* — Gary J. Gershik

(57) ABSTRACT

This invention provides a process for sequencing single-stranded DNA by employing a nanopore and modified nucleotides.

5 Claims, 14 Drawing Sheets

Specification includes a Sequence Listing.

(56) References Cited

U.S. PATENT DOCUMENTS

| | | |
|---|---|---|
| 5,770,367 A | 6/1998 | Southern et al. |
| 5,789,167 A | 8/1998 | Konrad |
| 5,798,210 A | 8/1998 | Canard et al. |
| 5,804,386 A | 9/1998 | Ju |
| 5,808,045 A | 9/1998 | Hiatt et al. |
| 5,814,454 A | 9/1998 | Ju |
| 5,821,356 A | 10/1998 | Khan et al. |
| 5,834,203 A | 11/1998 | Katzir |
| 5,844,106 A | 12/1998 | Seela et al. |
| 5,849,542 A | 12/1998 | Reeve et al. |
| 5,853,992 A | 12/1998 | Glazer |
| 5,856,104 A | 1/1999 | Chee et al. |
| 5,869,255 A | 2/1999 | Mathies |
| 5,872,244 A | 2/1999 | Hiatt et al. |
| 5,876,936 A | 3/1999 | Ju |
| 5,885,775 A | 3/1999 | Haff et al. |
| 5,908,755 A | 6/1999 | Kumar et al. |
| 5,945,283 A | 8/1999 | Kwok |
| 5,948,648 A | 9/1999 | Khan et al. |
| 5,952,180 A | 9/1999 | Ju |
| 5,959,089 A | 9/1999 | Hannessian |
| 5,962,228 A | 10/1999 | Brenner |
| 6,001,566 A | 12/1999 | Canard et al. |
| 6,001,611 A | 12/1999 | Will |
| 6,008,379 A | 12/1999 | Benson et al. |
| 6,013,445 A | 1/2000 | Albrecht et al. |
| 6,028,190 A | 2/2000 | Mathies |
| 6,046,005 A | 4/2000 | Ju et al. |
| 6,074,823 A | 6/2000 | Koster |
| 6,087,095 A | 7/2000 | Rosenthal et al. |
| 6,136,543 A | 10/2000 | Anazawa |
| 6,175,107 B1 | 1/2001 | Juvinall |
| 6,197,557 B1 | 3/2001 | Markarov |
| 6,207,831 B1 | 3/2001 | Auer et al. |
| 6,210,891 B1 | 4/2001 | Nyren |
| 6,214,987 B1 | 4/2001 | Hiatt |
| 6,218,118 B1 | 4/2001 | Sampson |
| 6,218,530 B1 | 4/2001 | Rothschild |
| 6,221,592 B1 | 4/2001 | Schwartz |
| 6,232,465 B1 | 5/2001 | Hiatt et al. |
| 6,242,193 B1 | 6/2001 | Anazawa et al. |
| 6,245,507 B1 | 6/2001 | Bogdanov |
| 6,255,083 B1 | 7/2001 | Williams |
| 6,255,475 B1 | 7/2001 | Kwiatkowski |
| 6,274,320 B1 | 8/2001 | Rothberg et al. |
| 6,277,607 B1 | 8/2001 | Tyagi et al. |
| 6,287,821 B1 | 9/2001 | Shi et al. |
| 6,294,324 B1 | 9/2001 | Bensimon et al. |
| 6,309,829 B1 | 10/2001 | Livak et al. |
| 6,309,836 B1 | 10/2001 | Kwiatkowski |
| 6,312,893 B1 | 11/2001 | Van Ness et al. |
| 6,316,230 B1 | 11/2001 | Egholm |
| 6,361,940 B1 | 3/2002 | Van Ness et al. |
| 6,380,378 B1 | 4/2002 | Kitamura et al. |
| 6,524,829 B1 | 2/2003 | Seeger |
| 6,555,349 B1 | 4/2003 | O'Donnell |
| 6,613,508 B1 | 9/2003 | Ness et al. |
| 6,613,513 B1 | 9/2003 | Parce et al. |
| 6,627,748 B1 | 9/2003 | Ju et al. |
| 6,632,655 B1 | 10/2003 | Mehta et al. |
| 6,639,088 B2 | 10/2003 | Kwiatkowski |
| 6,664,079 B2 | 12/2003 | Ju et al. |
| 6,664,399 B1 | 12/2003 | Sabesan |
| 6,713,255 B1 | 3/2004 | Makino et al. |
| 6,780,591 B2 | 8/2004 | Williams et al. |
| 6,787,308 B2 | 9/2004 | Balasubramanian et al. |
| 6,818,395 B1 | 11/2004 | Quake et al. |
| 6,833,246 B2 | 12/2004 | Balasubramanian et al. |
| 6,864,052 B1 | 3/2005 | Drmanac et al. |
| 6,911,345 B2 | 6/2005 | Quake et al. |
| 6,934,636 B1 | 8/2005 | Skierczynski et al. |
| 6,982,146 B1 | 1/2006 | Schneider et al. |
| 7,037,687 B2 | 5/2006 | Williams et al. |
| 7,056,661 B2 | 6/2006 | Korlach et al. |
| 7,056,666 B2 | 6/2006 | Dower et al. |
| 7,057,026 B2 | 6/2006 | Barnes et al. |
| 7,057,031 B2 | 6/2006 | Olejnik |
| 7,057,206 B2 | 6/2006 | Barnes et al. |
| 7,074,597 B2 | 7/2006 | Ju |
| 7,078,499 B2 | 7/2006 | Odedra et al. |
| 7,105,300 B2 | 9/2006 | Parce et al. |
| 7,270,951 B1 | 9/2007 | Stemple et al. |
| 7,279,563 B2 | 10/2007 | Kwiatkowski |
| 7,329,496 B2 | 2/2008 | Dower et al. |
| 7,345,159 B2 | 3/2008 | Ju |
| 7,393,533 B1 | 7/2008 | Crotty et al. |
| 7,414,116 B2 | 8/2008 | Milton et al. |
| 7,427,673 B2 | 9/2008 | Balasubramanian et al. |
| 7,459,275 B2 | 12/2008 | Dower et al. |
| 7,566,537 B2 | 7/2009 | Balasubramanian et al. |
| 7,622,279 B2 | 11/2009 | Ju et al. |
| 7,635,578 B2 | 12/2009 | Ju et al. |
| 7,713,698 B2 | 5/2010 | Ju et al. |
| 7,785,790 B1 | 8/2010 | Church et al. |
| 7,790,869 B2 | 9/2010 | Ju et al. |
| 7,883,869 B2 | 2/2011 | Ju et al. |
| 7,982,029 B2 | 7/2011 | Ju et al. |
| 8,088,575 B2 | 1/2012 | Ju et al. |
| 8,158,346 B2 | 4/2012 | Balasubramanian et al. |
| 8,298,792 B2 | 10/2012 | Ju et al. |
| 8,399,188 B2 | 3/2013 | Zhao et al. |
| 8,796,432 B2 | 8/2014 | Ju et al. |
| 8,889,348 B2 | 11/2014 | Ju |
| 9,115,163 B2 | 8/2015 | Ju et al. |
| 9,528,151 B2 * | 12/2016 | Ju ..................... C12Q 1/6823 |
| 10,000,801 B2 * | 6/2018 | Ju ..................... C12Q 1/6823 |
| 11,098,353 B2 * | 8/2021 | Ju ..................... C12Q 1/6823 |
| 2002/0012966 A1 | 1/2002 | Shi et al. |
| 2002/0168642 A1 | 11/2002 | Drukier |
| 2003/0008285 A1 | 1/2003 | Fischer |
| 2003/0022225 A1 | 1/2003 | Monforte |
| 2003/0027140 A1 | 2/2003 | Ju et al. |
| 2003/0044871 A1 | 3/2003 | Cutsforth et al. |
| 2003/0054360 A1 | 3/2003 | Gold et al. |
| 2003/0099972 A1 | 5/2003 | Olejnik et al. |
| 2003/0166282 A1 | 9/2003 | Brown et al. |
| 2003/0180769 A1 | 9/2003 | Metzker |
| 2003/0186256 A1 | 10/2003 | Fischer |
| 2003/0190680 A1 | 10/2003 | Rothschild et al. |
| 2003/0198982 A1 | 10/2003 | Seela et al. |
| 2004/0014096 A1 | 1/2004 | Anderson et al. |
| 2004/0096825 A1 | 5/2004 | Chenna et al. |
| 2005/0032081 A1 | 2/2005 | Ju et al. |
| 2005/0239134 A1 | 10/2005 | Gorenstein et al. |
| 2006/0003352 A1 | 1/2006 | Lipkin et al. |
| 2006/0057565 A1 | 3/2006 | Ju et al. |
| 2006/0105461 A1 | 5/2006 | Tom-Moy et al. |
| 2006/0160081 A1 | 7/2006 | Milton et al. |
| 2006/0240439 A1 | 10/2006 | Smith et al. |
| 2006/0252038 A1 | 11/2006 | Ju et al. |
| 2007/0166705 A1 | 7/2007 | Milton et al. |
| 2009/0088332 A1 | 4/2009 | Ju et al. |
| 2009/0240030 A1 | 9/2009 | Ju et al. |
| 2009/0263791 A1 | 10/2009 | Ju et al. |
| 2009/0298072 A1 | 12/2009 | Ju et al. |
| 2009/0325154 A1 | 12/2009 | Ju et al. |
| 2010/0159531 A1 | 6/2010 | Gordon et al. |
| 2010/0323350 A1 | 12/2010 | Gordon et al. |
| 2011/0014611 A1 | 1/2011 | Ju et al. |
| 2011/0039259 A1 | 2/2011 | Ju et al. |
| 2011/0124054 A1 | 5/2011 | Olejnik et al. |
| 2012/0052489 A1 | 3/2012 | Gordon et al. |
| 2012/0142006 A1 | 6/2012 | Ju et al. |
| 2012/0156680 A1 | 6/2012 | Ju et al. |
| 2013/0264207 A1 | 10/2013 | Ju et al. |
| 2013/0280700 A1 | 10/2013 | Ju et al. |
| 2014/0093869 A1 | 4/2014 | Ju et al. |
| 2014/0206553 A1 | 7/2014 | Ju et al. |
| 2014/0377743 A1 | 12/2014 | Ju et al. |
| 2015/0037788 A1 | 2/2015 | Ju et al. |

(56) References Cited

U.S. PATENT DOCUMENTS

| | | |
|---|---|---|
| 2015/0080232 A1 | 3/2015 | Ju et al. |
| 2019/0136308 A1 | 5/2019 | Ju et al. |

FOREIGN PATENT DOCUMENTS

| | | |
|---|---|---|
| DE | 20122767.3 U1 | 8/2008 |
| DE | 112007002932.3 | 8/2015 |
| EP | 0251786 B1 | 11/1994 |
| EP | 0995804 | 4/2000 |
| EP | 1182267 | 2/2002 |
| EP | 1291354 | 3/2003 |
| EP | 0808320 | 4/2003 |
| EP | 1337541 B1 | 3/2007 |
| EP | 1218391 | 4/2007 |
| EP | 1790736 A2 | 5/2007 |
| EP | 0992511 | 3/2009 |
| EP | 2209911 B1 | 10/2013 |
| GB | 2000 0013276 | 6/2000 |
| GB | 2001 0029012 | 12/2001 |
| GB | 2446083 | 3/2011 |
| GB | 2446084 | 3/2011 |
| GB | 2457402 | 9/2011 |
| WO | WO 89/09282 | 10/1989 |
| WO | WO 89/10977 | 11/1989 |
| WO | WO 89/11548 | 11/1989 |
| WO | WO 90/13666 | 11/1990 |
| WO | WO 91/06678 | 5/1991 |
| WO | WO 92/10587 | 6/1992 |
| WO | WO 93/05183 | 3/1993 |
| WO | WO 93/12340 | 10/1993 |
| WO | WO 93/21340 | 10/1993 |
| WO | WO 94/14972 | 7/1994 |
| WO | WO 96/07669 | 3/1996 |
| WO | WO 96/23807 | 8/1996 |
| WO | WO 96/27025 | 9/1996 |
| WO | WO 97/08183 | 3/1997 |
| WO | WO 97/27317 | 7/1997 |
| WO | WO 97/35033 | 9/1997 |
| WO | WO 98/30720 | 7/1998 |
| WO | WO 98/33939 | 8/1998 |
| WO | WO 98/44151 | 10/1998 |
| WO | WO 99/05315 | 2/1999 |
| WO | WO 99/49082 | 9/1999 |
| WO | WO 99/57321 | 11/1999 |
| WO | WO 00/02895 | 1/2000 |
| WO | WO 00/06770 | 2/2000 |
| WO | WO 00/09753 | 2/2000 |
| WO | WO 00/15844 | 3/2000 |
| WO | WO 00/18956 | 4/2000 |
| WO | WO 00/21974 | 4/2000 |
| WO | WO 00/50172 | 8/2000 |
| WO | WO 00/50642 | 8/2000 |
| WO | WO 00/53805 | 9/2000 |
| WO | WO 00/53812 | 9/2000 |
| WO | WO 00/70073 | 11/2000 |
| WO | WO 01/16375 | 3/2001 |
| WO | WO 01/23610 | 4/2001 |
| WO | WO 01/25247 | 4/2001 |
| WO | WO 01/27625 | 4/2001 |
| WO | WO 01/32930 | 5/2001 |
| WO | WO 01/57248 | 8/2001 |
| WO | WO 01/57249 | 8/2001 |
| WO | WO 01/92284 | 12/2001 |
| WO | WO 02/02813 | 1/2002 |
| WO | WO 02/21098 | 3/2002 |
| WO | WO 02/22883 A1 | 3/2002 |
| WO | WO 02/29003 | 4/2002 |
| WO | WO 02/72892 | 9/2002 |
| WO | WO 02/79519 A1 | 10/2002 |
| WO | WO 02/88381 | 11/2002 |
| WO | WO 02/88382 | 11/2002 |
| WO | WO 03/02767 | 1/2003 |
| WO | WO 03/20968 | 3/2003 |
| WO | WO 03/48178 | 6/2003 |
| WO | WO 03/48387 | 6/2003 |
| WO | WO 03/85135 | 10/2003 |
| WO | WO 04/18493 | 3/2004 |
| WO | WO 04/18497 | 3/2004 |
| WO | WO 04/55160 | 7/2004 |
| WO | WO 06/73436 | 7/2006 |
| WO | WO 07/62105 | 5/2007 |
| WO | WO 2012/162429 | 11/2012 |
| WO | WO 2013/154999 | 10/2013 |
| WO | WO 2013/191793 | 12/2013 |
| WO | WO 2014/144883 | 9/2014 |
| WO | WO 2014/144898 | 9/2014 |
| WO | WO 2014/123430 | 8/2015 |

OTHER PUBLICATIONS

U.S. Appl. No. 12/804,025, filed Jul. 13, 2010, Balasubramanian et al.
U.S. Appl. No. 10/227,131, filed Aug. 23, 2002, Barnes et al.
U.S. Appl. No. 09/684,670, filed Oct. 16, 2000, Ju et al.
U.S. Appl. No. 09/684,670, filed Oct. 6, 2000, Ju et al.
Apr. 18, 2014 Patentee Motion to Exclude Evidence in connection with IPR2013-00266.
Apr. 18, 2014 Petitioner Motion for Observations on the Cross-Examination Testimony of Dr. Romesberg, in connection with IPR2013-00266.
Apr. 18, 2014 Petitioner Motion to Exclude Evidence in connection with IPR2013-00266.
Apr. 26, 2013 Opposition to Request for Reconsideration (Rehearing) Under 37 C.F.R. 42.71. (C) in connection with IPR2012-00006.
Apr. 26, 2013 Opposition to Request for Reconsideration (Rehearing) Under 37 C.F.R. 42.71. (C) in connection with IPR2012-00007.
Apr. 26, 2013 Opposition to Request for Reconsideration (Rehearing) Under 37 C.F.R. 42.71. (C) in connection with IPR2013-00011.
Arbo et al. (1993) "Solid Phase Synthesis of Protected Peptides Using New Cobalt (III) Amine Linkers," Int. J. Peptide Protein Res. 42:138-154.
Aug. 19, 2013 Petition 1 of 2 for Inter Partes Review of U.S. Pat. No. 7,566, 537, dated Jul. 28, 2009.
Aug. 19, 2013 Petition 2 of 2 for Inter Partes Review of U.S. Pat. No. 7,566,537, dated Aug. 19, 2013.
Aug. 30, 2013 Revised Petition 1 of 2 for Inter Partes Review of U.S. Pat. No. 7,566,537, dated Jul. 28, 2009.
Aug. 30, 2013 Substitute Patent Owner Motion to Amend Under 37 C.F.R. 42.121 in connection with IPR2012-00006.
Aug. 30, 2013 Substitute Patent Owner Motion to Amend Under 37 C.F.R. 42.121 in connection with IPR2012-00007.
Aug. 30, 2013 Substitute Patent Owner Response Under 37 C.F.R. 42.120 in connection with IPR2012-00006.
Aug. 30, 2013 Substitute Patent Owner Response Under 37 C.F.R. 42.120 in connection with IPR2012-00007.
Aug. 30, 2013 Substitute Patent Owner Response Under 37 C.F.R. 42.120 in connection with IPR2013-00011.
Aug. 5, 2013 Patent Owner Preliminary Response to Petition for Inter Partes Review of U.S. Pat. No. 8,158,246, dated Apr. 17, 2012.
Axelrod, V. D. et al. (1978) "Specific termination of RNA polymerase synthesis as a method of RNA and DNA sequencing," Nucleic Acids Res. 5(10):3549-3563.
Badman, E. R. et al. (2000) "A Parallel Miniature Cylindrical Ion Trap Array, " Anal. Chem (2000) 72:3291-3297.
Badman, E. R. et al. (2000) "Cylindrical Ion Trap Array with Mass Selection by Variation in Trap Dimensions," Anal. Chem. 72:5079-5086.
Bai et al. (2003) "Photocleavage of a 2-nitrobenzyl Linker Bridging a Fluorophore to the 5' end of DNA, " PNAS, vol. 100, No. 2, pp. 409-413.
Bai, X., Kim, S., Li, Z., Turro, N.J. and Ju, J. "Design and synthesis of a photocleavable biotinylated nucleotide for DNA analysis by mass spectrometry." Nucleic Acids Research 2004, 32(2) ; pp. 534-541.
Benson, S. C., Mathies, R. A., and Glazer, A. N. (1993) "Heterodimeric DNA-binding dyes designed for energy transfer: stability and applications of the DNA complexes," Nucleic Acids Res, 21:5720-5726.

(56) References Cited

OTHER PUBLICATIONS

Benson, S.C., Singh, P., and Glazer, A.N. (1993) "Heterodimeric DNA-binding dyes designed for energy transfer: synthesis and spectroscopic properties, " Nucleic Acids Res. 21: 5727-5735.

Bergmann et al. (1995) "Allyl As Internucleotide Protecting Group in DNA Synthesis to be Cleaved Off By Ammonia," Tetrahedron, 51:6971-6976.

Bergseid M., Baytan A.R., Wiley J.P., Ankener W. M. , Stolowitz, Hughs K.A., and Chestnut J.D. (2000) "Small-molecule base chemical affinity system for the purification of proteins," BioTechniques 29:1126-1133.

Bi, L.; Kim D. H.; and Ju, J. (2006) "Design and Synthesis of a Chemically Cleavable Fluorescent Nucleotide, 3'-O-Ally1-dGTP-allyl-Bodipy-FL-510, as a Reversible Terminator for DNA Sequencing by Synthesis." J. Am. Chem. Soc., 128, pp. 2542-2543.

Braslavsky, I.; Hebert, B. ; Kartalov, E. ; et al. (2003) "Sequence information can be obtained from single DNA molecules." Proc. Natl. Acad. Sci., 100(7), pp. 3960-3964.

Brunckova, J. et al. (1994) "Intramolecular Hydrogen Atom Abstrction in Carbohydrates and Nucleosides; Inversion of an $\alpha$- to $\beta$-Mannopyranoside and Generation of Thymidine C-4' Radicals." Tetrahedron Letters, vol. 35, pp. 6619-6622.

Buck, G.A. et al. (1999) "Design Strategies and Performance of Custom DNA Sequencing Primers," BioTechniques 27(3):528-536.

Burgess, K. et al. (1997) "Photolytic Mass Laddering for Fast Characterization of Oligomers on Single Resin Beads," J. Org. Chem, 62:5662-5663.

Buschmann et al. (1999) "The Complex Formation of alpha, omega—Dicarboxylic Acids and alpha, omega—Diols with Cucurbituril and alpha-Cyclodextrin," Acta Chim. Slov. 46(3):405-411.

Buschmann et al. (2003) "Spectroscopic Study and Evaluation of Red-Absorbing Fluorescent Dyes," Bioconjugate Chem., 14:195-204.

Caetano-Anolies (1994) "DNA Amplification Fingerprinting Using Arbitrary Mini-hairpin Oligonucleotide Primers." Nature Biotechnology, 12:619-623.

Canard, B. et al. (1994) "DNA polymerase fluorescent substrates with reversible 3'-tags," Gene, 148:1-6.

Canard, B. et al. (1995) "Catalytic editing properties of DNA polymerases," Proc. Natl. Acad. Sci. USA 92:10859-10863.

Caruthers, M.H. (1985) "Gene synthesis machines: DNA chemistry and its uses," Science 230:281-285.

Chee, M. et al. (1996) "Accessing genetic information with high density DNA arrays," Science 274:610-614.

Chen, X. and Kwok, P.-Y. (1997) "Template-directed dye-terminator incorporation (TDI) assay; a homogeneous DNA diagnostic method based on fluorescence resonance energy transfer," Nucleic Acids Res. 25:347-353.

Chiu, N.H., Tang, K., Yip, P., Braun, A., Koster, H., and Cantor, C.R. (2000) "Mass spectrometry of single-stranded restriction fragments captured by an undigested complementary sequence, " Nucleic Acids Res, 28:E31.

Collins, F. S.; Morgan, M.; Patrinos, A. (2003) "The Human GenomeProject: Lessons from Large-Scale Biology." Science, 300, pp. 286-290.

Communication Pursuant to Article 94 (3) EPC dated Apr. 30, 2009 in connection with counterpart European Patent Application No. 07004522.4.

Crespo-Hernandez et al., (2000) "Part 1. Photochemical and Photophysical Studies of Guanine Derivatives: Intermediates Contributing to its Photodestruction Mechanism in Aqueous Solution and the Participation of the Electron Adduct," Photochemistry and Photobiology, 71(5):534-543.

Dec. 20, 2012 Preliminary Response under 37 C.F.R. 42.107 in connection with IPR2012-00006.

Dec. 21, 2012 Preliminary Response under 37 C.F.R. 42.107 in connection with IPR2012-00007.

Dec. 3, 2013 Patent Owner Reply on Motion to Exclude in connection with IPR2012-00006.

Dec. 3, 2013 Patent Owner Reply on Motion to Exclude in connection with IPR2012-00007.

Dec. 3, 2013 Patent Owner Reply on Motion to Exclude in connection with IPR2013-00011.

Dec. 3, 2013 Petitioner Reply to Patent Owner's Opposition to Motion to Exclude in connection with IPR2012-00006.

Dec. 3, 2013 Petitioner Reply to Patent Owner's Opposition to Motion to Exclude in connection with IPR2012-00007.

Dec. 3, 2013 Petitioner Reply to Patent Owner's Opposition to Motion to Exclude in connection with IPR2013-00011.

Dec. 30, 2013 Illumina Motion to Amend Under 37 C.F.R. §42.121 in connection with IPR2013-00266.

Dec. 8, 2014 Office Action issued in connection with German Patent Application No. 11 2007 002 932.3, including allowable claims (with translation of claims only).

Dec. 8, 2014 Office Action issued in connection with German Patent Application No. 11 2007 002 932.3.

Demonstrative Exhibits of Illumina for Apr. 23, 2014 hearing, filed Apr. 21, 2014 in connection with IPR2013-00128.

Demonstrative Exhibits of Intelligent Bio-Systems, Inc., for Apr. 23, 2014 hearing, filed Apr. 18, 2014 in connection with IPR2013-00128.

Drmanac, S.; Kita, D.; Labat, I.; et al. (1998) "Accurate sequencing by hybridization for DNA diagnostics and individual genomics." Nat. Biotech., 16, pp. 54-58.

Edwards, J. et al. (2001) "DNA sequencing using biotinylated dideoxynucleotides and mass spectrometry." Nucleic Acids Res., 29(21), pp. 1041-1046.

Elango, N. et al. (1983) "Amino Acid Sequence of Human Respiratory Syncytial Virus Nucleocapsid Protein," Nucleic Acids Research 11(17):5941-5951.

European Search Report dated Feb. 27, 2004 in connection with European Patent Application No. 01977533.7.

Exhibit 1003, filed Sep. 16, 2012 in connection with IPR2012-00006: Prober et al. (1987), "A System for Rapid DNA Sequencing with Fluorescent Chain-Terminating Dideoxynucleotides", *Science* vol. 238, Oct. 16, 1987, pp. 336-341.

Exhibit 1004, filed Aug. 19, 2013 in connection with IPR2013-00517: Zavgorodny et al., 1-Alkylthioalkylation of Nucleoside Hydroxyl Functions and Its Synthetic Applications: A New Versatile Method in Nucleoside Chemistry, 32 Tetrahedron Letters 7593 (1991).

Exhibit 1004, filed Aug. 19, 2013 in connection with IPR2013-00518: Kamal et al., A Mild and Rapid Regeneration of Alcohols from their Allylic Ethers by Chlorotrimethylsilane / Sodium Iodide, 40 Tetrahedron Letters 371 (1999).

Exhibit 1004, filed Jun. 4, 2013 in connection with IPR2013-00324: J. Meinwald, An Approach To the Synthesis of Pederin, 49 Pure and Appl. Chem, 1275 (1977).

Exhibit 1004, filed May 4, 2013 in connection with IPR2013-00266; Kamal et al., A Mild and Rapid Regeneration of Alcohols from their Allylic Ethers by Chlorotrimethylsilane/Sodium Iodide, 40 Tetrahedron Letters 371 (1999).

Exhibit 1005, filed Aug. 19, 2013 in connection with IPR2013-00517: Protective Groups in Organic Synthesis (Theodora W. Greene & Peter G. M. Wuts eds., John Wiley & Sons, Inc. 3rd ed. 1999) (1991).

Exhibit 1005, filed Aug. 19, 2013 in connection with IPR2013-00518: Jung et al., Conversion of Alkyl Carbamates into Amines via Treatment with Trimethylsilyl Iodide, 7 J.C.S. Chem. Comm. 315 (1978).

Exhibit 1005, filed Jun. 4, 2013 in connection with IPR2013-00324: Takeshi Matsumoto et al., A Revised Structure of Pederin, 60 Tetrahedron Letters 6297 (1968).

Exhibit 1005, filed May 4, 2013 in connection with IPR2013-00266: Jung et al., Conversion of Alkyl Carbamates into Amines vie Treatment with Trimethylsilyl Iodide, 7 J.C.S. Chem. Comm. 315 (1978).

Exhibit 1006, filed Jan. 29, 2013 in connection with IPR2013-00128: Beckman Coulter CEQTM 2000 DNA Analysis System User's Guide, Jun. 2000.

(56) References Cited

OTHER PUBLICATIONS

Exhibit 1007, filed Aug. 19, 2013 in connection with IPR2013-00518: Prober et al., A System for Rapid DNA Sequencing with Fluorescent Chain-Terminating Dideoxynucleotides, 238 Science 336 (1987).
Exhibit 1008, filed Jun. 4, 2013 in connection with IPR2013-00324: Beckman Coulter CEQTM 2000 DNA Analysis System User's Guide, Jun. 2000.
Exhibit 1009, filed Aug. 19, 2013 in connection with IPR2013-00517: Prober et al., A System for Rapid DNA Sequencing with Fluorescent Chain-Terminating Dideoxynucleotides, 238 Science 336 (1987).
Exhibit 1009, filed Jun. 4, 2013 in connection with IPR2013-00324: Jun. 4, 2013 Declaration of Dr. Bruce Branchaud;.
Exhibit 1010, filed Jan. 29, 2013 in connection with IPR2013-00128: Kamal, Tetrahedron Letters 40(2):371-372, 1999.
Exhibit 1010, filed Jun. 4, 2013 in connection with IPR2013-00324: Excerpts from the '026 Patent File History.
Exhibit 1011, filed Aug. 19, 2013 in connection with IPR2013-00517: Aug. 16, 2013 Declaration of Dr. Bruce Branchaud.
Exhibit 1011, filed Jan. 29, 2013 in connection with IPR2013-00128: Jung, J.C.S. Chem. Comm. (7):315-316, 1978.
Exhibit 1011, filed Jun. 4, 2013 in connection with IPR2013-00324: Excerpts from the file history of European Patent Application No. 02781434.2.
Exhibit 1011, filed May 4, 2013 in connection with IPR2013-00266: May 3, 2013 Declaration of Dr. Bruce Branchaud.
Exhibit 1012, filed Aug. 19, 2013 in connection with IPR2013-00517: Excerpts from the Mar. 20, 2013 Deposition Transcript of Dr. Xiaohai Liu.
Exhibit 1012, filed May 4, 2013 in connection with IPR2013-00266; Excerpts from the '346 Patent File History.
Exhibit 1013, filed Aug. 19, 2013 in connection with IPR2013-00517: Sep. 16, 2012 Petition for Inter Partes Review of U.S. Pat. No. 7,713,698.
Exhibit 1013, filed Jan. 29, 2013 in connection with IPR2013-100128: Prober et al., *Science* 238, 336-341 (1987).
Exhibit 1013, filed May 4, 2013 in connection with IPR2013-00266; Excerpts from the file history of European Patent Application No. 02781434.2.
Exhibit 1014, filed Aug. 19, 2013 in connection with IPR2013-00517: Sep. 16, 2012 Petition for Inter Partes Review of U.S. Pat. No. 7,790,869.
Exhibit 1014, filed May 4, 2013 in connection with IPR2013-00266: Sep. 16, 2013 Petition for Inter Partes Review of U.S. Pat. No. 7,713,698.
Exhibit 1015, filed Aug. 19, 2013 in connection with IPR2013-00517: Oct. 3, 2012 Petition for Inter Partes Review of U.S. Pat. No. 8,088,575.
Exhibit 1015, filed Aug. 19, 2013 in connection with IPR2013-00518: Aug. 16, 2013 Declaration of Dr. Bruce Branchaud.
Exhibit 1015, filed Jan. 29, 2013 in connection with IPR2013-00128: Jan. 28, 2013 Declaration of Dr. Bruce Branchaud.
Exhibit 1015, filed May 4, 2013 in connection with IPR2013-00266: Sep. 16, 2013 Petition for Inter Partes Review of U.S. Pat. No. 7,790,869.
Exhibit 1016, filed Aug. 19, 2013 in connection with IPR2013-00518: Excerpts from the 1537 Patent File History.
Exhibit 1016, filed Jan. 29, 2013 in connection with IPR2013-00128: Excerpts from the '026 Patent File History.
Exhibit 1016, filed May 4, 2013 in connection with IPR2013-00266: Oct. 3, 2013 Petition for Inter Partes Review of U.S. Pat. No. 8,088,575.
Exhibit 1017, filed Aug. 19, 2013 in connection with IPR2013-00518: Excerpts from the file history of European Patent Application No. 02781434.2.
Exhibit 1017, filed Jan. 29, 2013 in connection with IPR2013-00128: Sep. 16, 2012 Petition for Inter Partes Review of U.S. Pat. No. 7,713, 98.

Exhibit 1018, filed Aug. 19, 2013 in connection with IPR2013-00518: Sep. 16, 2012 Petition for Inter Partes Review of U.S. Pat. No. 7,713,698.
Exhibit 1018, filed Jan. 29, 2013 in connection with IPR2013-00128: Sep. 16, 2012 Petition for Inter Partes Review of U.S. Pat. No. 7,790,869.
Exhibit 1019, filed Aug. 19, 2013 in connection with IPR2013-00518: Sep. 16, 2012 Petition for Inter Partes Review of U.S. Pat. No. 7,790,869.
Exhibit 1019, filed Jan. 29, 2013 in connection with IPR2013-00128: Oct. 3, 2012 Petition for Inter Partes Review of U.S. Pat. No. 8,088,575.
Exhibit 1019, filed Jul. 28, 2014 in connection with IPR2013-00517; Ireland et al., Approach to the Total Synthesis of Chlorothricolide: Synthesis of (+)-19,20-Dihydro-24-O-methylchlorothricolide, Methyl Ester, Ethyl Carbonate, 51 J. Org. Chem. 635 (1986).
Exhibit 1020, filed Aug. 19, 2013 in connection with IPR2013-100518: Sep. 16, 2012 Petition for Inter Partes Review of U.S. Pat. No. 8, 088,575.
Exhibit 1020, filed Feb. 28, 2014 in connection with IPR2013-00266: Mitra et al, "Fluorescent in situ sequencing on polymerase colonies" Analytical Biochem. 320:55-65 (2003).
Exhibit 1020, filed Jan. 29, 2013 in connection with IPR2013-00128: Transcript of Initial Conference Call Held on Aug. 29, 2013.
Exhibit 1020, filed Jul. 28, 2014 in connection with IPR2013-00517; Gordon et al., Abstract, The Relationship of Structure to Effectiveness of Denaturing Agents for DNA, Biophysical Society 6th Annual Meeting (Washington, 1962).
Exhibit 1021, filed Dec. 23, 2013 in connection with IPR2013-00128: Excerpts from Protective Groups in Organic Synthesis (Theodora W. Greene & Peter G. M. Wuts eds., John Wiley & Sons, Inc. 3rd ed. 1999) (1991).
Exhibit 1021, filed Feb. 28, 2014 in connection with IPR2013-00266: Second Declaration of Dr. Bruce Branchaud in support of Intelligent Bio-Systems, Inc.'s Opposition to Illumina's Motion to Amend, from Feb. 28, 2014.
Exhibit 1021, filed Oct. 3, 2012 in connection with IPR2013-00011: Oct. 2, 2012 Declaration of George Weinstock Under Rule 37 C.F.R. §1.132.
Exhibit 1021, filed Sep. 16, 2012 in connection with IPR2012-100006: Sep. 15, 2012 Declaration of George Weinstock Under Rule 37 C.F.R. §1.132.
Exhibit 1022, filed Dec. 23, 2013 in connection with IPR2013-00128: Signed Deposition Transcript of Dr. Bruce Branchaud on Oct. 3, 2013.
Exhibit 1022, filed Feb. 28, 2014 in connection with IPR2013-00266: Deposition of Floyd Romesberg, Ph. D., from Jan. 14, 2014.
Exhibit 1022, filed Jul. 28, 2014 in connection with IPR2013-00517; p. 295 from Mar. 20, 2003 deposition of Dr. Xiaohai Liu, *The Trustees of Columbia University and Intelligent Bio-Systems, Inc, v. Illumina,* 12-376 (GMS) (D. Del.).
Exhibit 1022, filed Oct. 3, 2012 in connection with IPR2013-00011: Excerpts of File History of U.S. Pat. No. 8,088,575.
Exhibit 1022, filed Sep. 16, 2012 in connection with IPR2012-00006: Excerpts of File History of U.S. Pat. No. 7,713,698.
Exhibit 1022, filed Sep. 16, 2012 in connection with IPR2012-00007: Excerpts of File History of U.S. Pat. No. 7,790,869.
Exhibit 1025, filed Apr. 30, 2013 in connection with IPR2012-00006: *Columbia's Amended Complaint from The Trustees of Columbia University in the City of New York v. Illumina, Inc.,* D. Del C.A. No. 12-376 (GMS), filed Apr. 11, 2012.
Exhibit 1025, filed Jan. 24, 2014 in connection with IPR2013-00128: Substitute Eric Vermaas Declaration, Dec. 20, 2013.
Exhibit 1025, filed Jul. 28, 2014 in connection with IPR2013-00517: Transcript, Jul. 8, 2014 Deposition of Floyd Romesberg, Ph. D.
Exhibit 1026, filed Apr. 30, 2013 in connection with IPR2012-00006: Illumina's Answer to Amended Complaint from *The Trustees of Columbia University in the City of New York v. Illumina, Inc.,* D. Del C.A. No. 12-376 (GMS), filed Dec. 21, 2012.
Exhibit 1026, filed Jul. 28, 2014 in connection with IPR2013-00517: Transcript, Jul. 15, 2014 Deposition of Kevin Burgess, Ph.D.

(56) References Cited

OTHER PUBLICATIONS

Exhibit 1027, filed Feb. 28, 2014 in connection with IPR2013-100266: Dawson et al., "Affinity Isolation of Transcriptionally Active Murine Erythroleukemia Cell DNA Using a Cleavable Biotinylated Nucleotide Analog" J. of Biol. Chem., 264:12830-37 (1989).
Exhibit 1028, filed Feb. 28, 2014 in connection with IPR2013-00266: Canard et al., "DNA polymerase fluorescent substrates with reversible 3'-tags" Gene, 148: 1-6 (1994).
Exhibit 1029, filed Feb. 28, 2014 in connection with IPR2013-00266: Deposition of Eric Vermaas from Jan. 13, 2014.
Exhibit 1029, filed Jan. 24, 2014 in connection with IPR2013-00128: Jan. 9, 2014 Substitute Declaration of Floyd Romesberg, Ph.D.
Exhibit 1030, filed Jan. 24, 2014 in connection with IPR2013-00128: Dawson et al., "Affinity Isolation of Transcriptionally Active Murine Erythroleukemia Cell DNA Using a Cleavable Biotinylated Nucleotide Analog" J. of Biol. Chem., 264, 12830-37 (1989).
Exhibit 1030, filed Jul. 28, 2014 in connection with IPR2013-00517: Patent prosecution excerpt from file history of U.S. Pat. No. 7,566,537 (U.S. Appl. No. 11/301,578).
Exhibit 1030, filed Jun. 18, 2013 in connection with IPR2012-00006; Rosenblum et al., "New Dye-Labeled Terminators for Improved DNA Sequencing Patterns," Nucleic Acid Research, 1997, vol. 25, No. 22, pp. 4500-4504.
Exhibit 1031, filed Feb. 28, 2014 in connection with IPR2013-00266: Lukesh et al., "A Potent, Versatile Disulfide-Reducing Agent from Aspartic Acid" J. Am. Chem. Soc., 134:4057-59 (2012).
Exhibit 1031, filed Jul. 28, 2014 in connection with IPR2013-00517: Second Declaration of Dr. Bruce Branchaud in Support Of Intelligent Bio-Systems, Inc.'s Reply to Illumina's Patent Owner Response.
Exhibit 1032, filed Feb. 28, 2014 in connection with IPR2013-00266: Prober et al., "A System for Rapid DNA Sequencing with Fluorescent Chain Terminating Dideoxynucleotides" Science, 238:336-341 (1987).
Exhibit 1032, filed Jan. 24, 2014 in connection with IPR2013-00128: Mitra et al., "Fluorescent in situ sequencing on polymerase colonies" Analytical Biochem. 320, 55-65 (2003).
Exhibit 1032, filed Jul. 28, 2014 in connection with IPR2013-00517; Gololobov and Kasukhin, Recent advances in the Staudinger reaction, Tetrahedron 48:1353-1406 (1992).
Exhibit 1033, filed Feb. 28, 2014 in connection with IPR2013-00266: Klausner, Nat. Biotech., "DuPont's New DNA Sequencer Uses New Chemistry" 5:1111-12 (1987).
Exhibit 1033, filed Jan. 24, 2014 in connection with IPR2013-00128: Deposition of Floyd Romesberg, Ph. D., from Jan. 14, 2014.
Exhibit 1034, filed Feb. 28, 2014 in connection with IPR2013-00266: Murakami, et al., "Structure of a *Plasmodium yoelii* gene-encoded protein homologous to the $Ca^{2+}$-ATPase of rabbit skeletal muscle sarcoplasmic reticulum" J. Cell Sci., 97, 487-95 (1990).
Exhibit 1034, filed Jan. 24, 2014 in connection with IPR2013-00128: 1999/2000 Pierce Chemical Company catalog (1999).
Exhibit 1034, filed Jul. 28, 2014 in connection with IPR2013-00517: Saxon and Bertozzi, Cell Surface Engineering by a Modified Staudinger Reaction, Science 287:2007-2010 (2000).
Exhibit 1034, filed Jun. 18, 2013 in connection with IPR2012-00006: Jun. 8, 2013 Videotaped Deposition Transcript of George M. Weinstock, Ph.D.
Exhibit 1035, filed Feb. 28, 2014 in connection with IPR2013-100266: Excerpts from Protective Groups in Organic Synthesis (Theodora W. Greene & Peter G. M. Wuts eds., John Wiley & Sons, Inc. 3rd ed. 1999) (1991).
Exhibit 1035, filed Jan. 24, 2014 in connection with IPR2013-49400128: Second Declaration of Dr. Bruce Branchaud, dated Jan. 23, 2014.
Exhibit 1036, filed Feb. 28, 2014 in connection with IPR2013-00266: Letsinger, et al., "2, 4-Dinitrobenzenesulfenyl as a Blocking Group for Hydroxyl Functions in Nucleosides" J. Org. Chem, , 29, 2615-2618 (1964).

Exhibit 1036, filed Jul. 28, 2014 in connection with IPR2013-00517: Faucher and Grand-Maitre, tris (2-Carboxyethyl) phosphine (TCEP) for the Reduction of Sulfoxides, Sulfonylchlorides, N-Oxides, and Azides, Synthetic Communications 33:3503-3511 (2003).
Exhibit 1036, filed Sep. 27, 2013 in connection with IPR2012-49700006: "Next Generation Genomics: World Map of High-throughput Sequencers," Sep. 1, 2013.
Exhibit 1037, filed Feb. 28, 2014 in connection with IPR2013-00266: Handlon & Oppenheimer, "Thiol Reduction of 3'-Azidothymidine to 3'-Aminothymidine: Kinetics and Biomedical Implications" Pharm. Res. 5:297-99 (1988).
Exhibit 1038, filed Feb. 28, 2014 in connection with IPR2013-00266: Zavgorodny et al., "1-Alkylthioalkylation of Nucleoside Hydroxyl Functions and Its Synthetic Applications; A New Versatile Method in Nucleoside Chemistry" 32 Tetrahedron Letters 7593 (1991).
Exhibit 1039, filed Feb. 28, 2014 in connection with IPR2013-50000266: Burns, et al., "Selective Reduction of Disulfides by Tris (2-carboxyethyl)phosphine" J. Org. Chem., 56, 2648-50 (1991).
Exhibit 1039, filed Jan. 24, 2014 in connection with IPR2013-00128: Excerpts from the file history of European Patent Application No. 02781434.2.
Exhibit 1039, filed Sep. 27, 2013 in connection with IPR2012-00006: Videotaped Deposition Transcript of Dr. Xiaohai Liu, Mar. 20, 2013.
Exhibit 1040, filed Sep. 27, 2013 in connection with IPR2012-00006: Excerpt from videotaped Deposition Transcript of George M. Weinstock, Ph.D., Jun. 8, 2013.
Exhibit 1041, filed Jan. 24, 2014 in connection with IPR2013-00128: Lukesh et al., "A Potent, Versatile Disulfide-Reducing Agent from Aspartic Acid" J. Am. Chem. Soc., 134: 4057-59 (2012).
Exhibit 1041, filed Jul. 28, 2014 in connection with IPR2013-00517: Mag and Engels, Synthesis and selective cleavage of oligodeoxyribonucleotides containing non-chiral internucleotide phosphoramidate linkages, Nucleic Acids Research 15:5973-5988 (1989).
Exhibit 1041, filed Sep. 27, 2013 in connection with IPR2012-100006: Seela et al., "Oligonucleotide Duplex Stability Controlled by the 7-Substituents of 7-Deazaguanine Bases," Bioorganic & Medical Chemistry Letters, vol. 5, No. 24, pp. 3049-3052, 1995.
Exhibit 1042, filed Apr. 18, 2014 in connection with IPR2013-00266: Apr. 10, 2014 transcript of Deposition of Floyd Romesberg.
Exhibit 1042, filed Jan. 24, 2014 in connection with IPR2013-00128: Klausner, "DuPont's DNA Sequencer Uses New Chemistry" Nat. Biotech., 5:1111-12 (1987).
Exhibit 1042, filed Sep. 27, 2013 in connection with IPR2012-00006: Ramzaeva et al., "123. 7-Deazaguanine DNA: Oligonucleotides with Hydrophobic or Cationic Side Chains," Helvetica Chimica Acta, vol. 80, pp. 1809-1822, 1997.
Exhibit 1043, filed Jan. 24, 2014 in connection with IPR2013-00128: Murakami et al., "Structure of a *Plasmodium yoelii* gene-encoded protein homologous to the $Ca^{2+}$-ATPase of rabbit skeletal muscle sarcoplasmic reticulum" J. Cell Sci., 97, 487-95 (1990).
Exhibit 1043, filed Jul. 28, 2014 in connection with IPR2013-00517: Chang and Bollum, Molecular biology of terminal transferase, CRC Critical Reviews in Biochemistry 21:27-52 (1986).
Exhibit 1043, filed Sep. 27, 2013 in connection with IPR2012-00006: Ramzaeva et al., "88. 7-Substituted 7-Deaza-2'-deoxyguanosines: Regioselective Halogenation of Pyrrolo [2, 3-d]pyrimidine Nucleosides," Helvetica Chimica Acta, vol. 78, pp. 1083-1090, 1995.
Exhibit 1044, filed Jan. 24, 2014 in connection with IPR2013-00128: Letsinger et al., "2, 4-Dinitrobenzenesulfenyl as a Blocking Group for Hydroxyl Functions in Nucleosides" J. Org. Chem. , 29:2615-2618 (1964).
Exhibit 1044, filed Jul. 28, 2014 in connection with IPR2013-00517: Chen, DNA polymerases drive DNA sequencing-by-synthesis technologies; both past and present, Frontiers In Microbiology, vol. 5, Article 305, 1-11 (2014).
Exhibit 1044, filed Sep. 27, 2013 in connection with IPR2012-00006: Seela et al., "Duplex Stability of Oligonucleotides Containing 7-Substituted 7-Deaza- and 8-Aza-7-Deazapurine Nucleosides," Nucleosides & Nucleotides, 16(7-9), pp. 963-966, 1997.

(56) References Cited

OTHER PUBLICATIONS

Exhibit 1045, filed Jan. 24, 2014 in connection with IPR2013-00128: Handlon & Oppenheimer, "Thiol Reduction of 3'-Azidothymidine to 3'-Aminothymidine: Kinetics and Biomedical Implications" Pharm. Res., 5:297-99 (1988).
Exhibit 1045, filed May 22, 2014 in connection with IPR2013-00266: Petitioner Demonstratives for May 28, 2014 Oral Hearing.
Exhibit 1045, filed Sep. 27, 2013 in connection with IPR2012-00006: Burgess et al., "Syntheses of Nucleosides Designed for Combinatorial DNA Sequencing," Chemistry—A European Journal, vol. 5, No. 3, pp. 951-960, 1999.
Exhibit 1046, filed Jul. 28, 2014 in connection with IPR2013-00517; Declaration of Dr. Michael Metzker in Support of Intelligent Bio-Systems, Inc's Reply to Illumina's Patent Owner Response.
Exhibit 1047, filed Jan. 24, 2014 in connection with IPR2013-00128: Burns et al., "Selective Reduction of Disulfides by Tris (2-carboxyethyl) phosphine" J. Org. Chem., 56:2648-50 (1991).
Exhibit 1047, filed Jul. 28, 2014 in connection with IPR2013-00517: Lebreton et al., Structure-Immunosuppressive Activity Relationships of New Analogues of 15-Deoxysperqualin. 2. Structural Modifications of the Spermidine Moiety, Journal of Medicinal Chemistry 42:4749-4763 (1999).
Exhibit 1048, filed Jul. 28, 2014 in connection with IPR2013-00517: Levine et al., The Relationship of Structure to the Effectiveness of Denaturing Agents for Deoxyribonucleic Acid, Biochemistry 2:168-175 (1963).
Exhibit 1048, filed Mar. 18, 2014 in connection with IPR2013-00128: Petitioner's Objections to Patentee's Exhibits submitted with its Reply to Petitioner's Opposition to Patentee's Motion to Amend.
Exhibit 1049, filed Jul. 28, 2014 in connection with IPR2013-00517; Efimov et al., An azidomethyl protective group in the synthesis of oligoribonucleotides by the phosphotriester method, 35:250-253 (2009).
Exhibit 1049, filed Sep. 27, 2013 in connection with IPR2012-00006: Jan. 28, 2013 Declaration of Dr. Bruce P. Branchaud in Support of Petition for Inter Partes Review of U.S. Pat. No. 7,057,026.
Exhibit 1050, filed Jul. 28, 2014 in connection with IPR2013-00517: Kirby, A new method for the isolation of deoxyribonucleic acids: Evidence of the nature of bonds between deoxyribonucleic acids and proteins, Biochemical Journal 66:495-504 (1957).
Exhibit 1050, filed Sep. 27, 2013 in connection with IPR2012-00006: Lee et al., "DNA sequencing with dye-labeled terminators and T7 DNA polymerase: effect of dyes and dNTPs on incorporation of dye-terminators and probability analysis of termination fragments," Nucleic Acids Research, vol. 20, No. 10, pp. 2471-2483, 1992.
Exhibit 1051, filed Jul. 28, 2014 in connection with IPR2013-00517: Bentley et al., Accurate whole human genome sequencing using reversible terminator chemistry. Nature 456:53 (2008)—Supplementary Information.
Exhibit 1051, filed Sep. 27, 2013 in connection with IPR2012-00006: http://www.answers.com/topic/incubate, Accessed Sep. 27, 2013.
Exhibit 1052, filed Sep. 27, 2013 in connection with IPR2012-00006: http://en.wikipedia.org/wiki/Fluorenylmethyloxycarbonyl_chloride, Accessed Sep. 27, 2013.
Exhibit 1053, filed Sep. 27, 2013 in connection with IPR2012-00006: Sep. 27, 2013 Declaration of Kevin Burgess.
Exhibit 1053, filed Sep. 27, 2013 in connection with IPR2012-00007: Sep. 27, 2013 Declaration of Kevin Burgess.
Exhibit 1053, filed Sep. 27, 2013 in connection with IPR2013-100011: Sep. 27, 2013 Declaration of Kevin Burgess.
Exhibit 1054, filed Sep. 27, 2013 in connection with IPR2012-00006: Fuji, et al., "An Improved Method for Methoxymethylation of Alcohols under Mild Acidic Conditions," Synthesis—The Journal of Synthetic Organic Chemistry, pp. 276-277, Apr. 1975.

Exhibit 1056, filed Nov. 19, 2013 in connection with IPR2012-00006: Videotaped Deposition Transcript of Kevin Burgess, Ph.D., Oct. 28, 2013, signed with errata.
Exhibit 1057, filed Dec. 16, 2013 in connection with IPR2012-00006: Illumina's Invalidity Demonstratives for Final Hearing Dec. 17, 2013 in connection with IPR2012-00006, IPR2012-00007, and IPR2013-00011.
Exhibit 2001, filed Aug. 5, 2013 in connection with IPR2013-00266: Columbia's Apr. 11, 2012 Amended Complaint in connection with case No. C.A. No. 12-376-GMS.
Exhibit 2001, filed Dec. 21, 2012 in connection with IPR2012-00007: Composition of a Nucleotide.
Exhibit 2001, filed May 1, 2013 in connection with IPR2013-00128: *The Trustees of Columbia University in the City of New York v. Illumina, Inc.*, 1:12-cv-00376-GMS—Columbia's Amended Complaint.
Exhibit 2002, filed Aug. 5, 2013 in connection with IPR2013-00266: Columbia's Jan. 7, 2013 Amended Answer in connection with case No. C.A. No. 12-376-GMS.
Exhibit 2002, filed May 1, 2013 in connection with IPR2013-00128: *The Trustees of Columbia University in the City of New York v. Illumina, Inc.*, 1:12-cv-00376-GMS-Columbia's Amended Answer.
Exhibit 2003, filed May 1, 2013 in connection with IPR2013-00128: *The Trustees of Columbia University in the City of New York v. Illumina, Inc.*, 1:12-cv-00376-GMS-IBS's Responses to Illumina's Requests for Admission.
Exhibit 2004, filed May 1, 2013 in connection with IPR2013-00128: *The Trustees of Columbia University in the City of New York v. Illumina, Inc.*, 1:12-cv-00376-GMS-Columbia's Response to Illumina's Requests for Admission.
Exhibit 2005, filed May 5, 2014 in connection with IPR2013-00517; IBS's Answer, *Affirmative Defenses & Counterclaims to Illumina, Inc. and Illumina Cambridge Ltd.'s Second Amended Counterclaims to Amended Complaint, Columbia v. Illumina*, No. 12-CV-00376 (D. Del).
Exhibit 2006, filed Apr. 26, 2013 in connection with IPR2012-00006: Dower patent with highlights.
Exhibit 2006, filed May 5, 2014 in connection with IPR2013-00517: Excerpts from file history of U.S. Appl. No. 13/305,415, filed Nov. 28, 2011, Gordon et al.
Exhibit 2006, filed Oct. 24, 2013 in connection with IPR2013-100128: Green & Wuts, Protective Groups in Organic Synthesis, excerpts from "Protection From the Hydroxyl Group," (1999).
Exhibit 2007, filed Oct. 24, 2013 in connection with IPR2013-00128: Katagiri et al., "Selective Protection of the Primary Hydroxyl Groups of Oxetanocin A," Chem. Pharm. Bull. 43:884-886 (1995).
Exhibit 2008, filed Dec. 30, 2013 in connection with IPR2013-00266: Maxam & Gilbert, PNAS 74:560-564 (Feb. 1977).
Exhibit 2009, filed Dec. 30, 2013 in connection with IPR2013-00266: Sanger et al., DNA Sequencing, PNAS 74:5463-5467 (1977).
Exhibit 2009, filed Feb. 19, 2014 in connection with IPR2013-00128: Substitute Declaration of Floyd Romesberg, Ph.D., in Support of Patent Owner's Motion to Amend.
Exhibit 2010, filed May 5, 2014 in connection with IPR2013-00517; Excerpts from prosecution history of U.S. Pat. No. 7,566,537, dated Jul. 28, 2009, Barnes et al.
Exhibit 2011, filed Dec. 30, 2013 in connection with IPR2013-00266: Metzker et al., Nucleic Acids Research, 22:4259-4267 (1994).
Exhibit 2011, filed May 5, 2014 in connection with IPR2013-00517: May 5, 2014 Declaration Of Floyd Romesberg, Ph.D.
Exhibit 2012, filed Dec. 30, 2013 in connection with IPR2013-00266: Welch and Burgess, Nucleosides & Nucleotides, 18:197-201 (1999).
Exhibit 2012, filed Oct. 24, 2013 in connection with IPR2013-00128: Oct. 3, 2013 Deposition Transcript of Bruce Branchaud, Ph.D.
Exhibit 2013, filed Dec. 30, 2013 in connection with IPR2013-00266: Bruce P. Branchaud, Ph.D., Jun. 4, 2013 Declaration in IPR2013-00324.
Exhibit 2013, filed Jun. 24, 2013 in connection with IPR2012-00006: Oct. 2, 2012 Declaration of George Weinstock Under 37 CFR 1.132 (Exhibit 1021 in IPR2013-00011).

(56) References Cited

OTHER PUBLICATIONS

Exhibit 2013, filed May 5, 2014 in connection with IPR2013-00517; Ranganathan et al., "Facile Conversion of Adenosine into New 2'-Substituted-2'-Deoxy-Arabinofuranosyladenine Derivatives: Stereospecific Syntheses of 2'-Azido-2'-Deoxy-, 2'-Amino-2'-Deoxy-, and 2'-Mercapto-2'-Deoxy-β-D-Arabinofuranosyladenines" Tetrahedron Letters 45:4341-44 (1978).
Exhibit 2014, filed Jun. 24, 2013 in connection with IPR2012-00006: Petition for Inter Partes Review of U.S. Pat. No. 8,088,575 (Paper 4 in IPR2013-00011).
Exhibit 2014, filed May 5, 2014 in connection with IPR2013-00517: Mungall et al., "Use of the Azido Group in the Synthesis of 5' Terminal Aminodeoxythymidine Oligonucleotides" J. Org. Chem., 40:1659-1662 (1975).
Exhibit 2015, filed Jun. 24, 2013 in connection with IPR2012-00006; Metzker et al. (1994) Termination of DNA synthesis by novel 3'-modified-deoxyribonucleoside 5'-triphosphates. Nucleic Acids Res. 22:4259-4267.
Exhibit 2016, filed Dec. 30, 2013 in connection with IPR2013-00266: Ruby et al., Methods in Enzymology, 181:97-121 (1990).
Exhibit 2016, filed Jun. 24, 2013 in connection with IPR2012-00006: Wu et al. (2007) Termination of DNA synthesis by N6-alkylated, not 3'-O-alkylated, photocleavable 2'-deoxyadenosine triphosphates. Nucleic Acids Res. 35:6339-6349.
Exhibit 2016, filed May 5, 2014 in connection with IPR2013-00517; Pilard et al., "A Stereospecific Synthesis of (±), α-Conhydrine and (+) β-Conhydrine)" Tet. Lett., 25:1555-1556 (1984).
Exhibit 2016, filed Oct. 24, 2013 in connection with IPR2013-00128: Ruby, Methods in Enzymology (1990).
Exhibit 2017, filed Jun. 24, 2013 in connection with IPR2012-00006: Sep. 15, 2012 Declaration of George Weinstock Under 37 CFR 1.132 (Exhibit 1021 in IPR2012-00007).
Exhibit 2017, filed May 5, 2014 in connection with IPR2013-00517; "Synthesis of a Novel Stable GM3-Lactone Analogue as Hapten for a Possible Immunization against Cancer" Tietze et al., Angew. Chem, Int. Ed., 36:1615, 1616 (1997).
Exhibit 2018, filed Jun. 24, 2013 in connection with IPR2012-00006: Sep. 15, 2012 Declaration of George Weinstock Under 37 CFR 1.132 (Exhibit 1021 in IPR2012-00006).
Exhibit 2018, filed May 5, 2014 in connection with IPR2013-00517: Kit, "Deoxyribonucleic Acids" Annual Rev. Biochem, 32:43 (1963).
Exhibit 2019, filed Jun. 24, 2013 in connection with IPR2012-00006: Definition of "DNA microarray." http://en/wikipedia.org/wiki/DNA_microarray.
Exhibit 2019, filed May 5, 2014 in connection with IPR2013-00517; Canard et al., "Catalytic editing properties of DNA polymerases" PNAS USA 92:10859 (1995).
Exhibit 2019, filed Oct. 24, 2013 in connection with IPR2013-00128: Sanger, "DNA Sequencing with Chain-Inhibiting Terminators" PNAS 74(12):6463-5467 (1977).
Exhibit 2020, filed Jun. 24, 2013 in connection with IPR2012-00006: Brettin et al. (2005) Expression capable library for studies of Neisseria gonorrhoeae, version 1.0 BMC Microbiology. 5:50.
Exhibit 2020, filed May 5, 2014 in connection with IPR2013-00517; The Merck Index, p. 9815 (entry for Triphenylphosphine) (13th Edition, 2001).
Exhibit 2021, filed Dec. 30, 2013 in connection with IPR2013-00266: Bystrom, Branchaud et al., "ATP Analogs with Non-transferable Groups in the g Position As Inhibitors of Glycerol Kinase" Bioorganic & Medicinal Chemistry Letters, 7:2613-2616 (1997).
Exhibit 2021, filed Jun. 24, 2013 in connection with IPR2012-00006: George M. Weinstock, Handbook of Molecular Microbial Ecology, vol. 1-Chapter 18: The Impact of Next-Generation Sequencing Technologies on Metagenomics 141-147 Frans J. de Bruijn ed., John Wiley & Sons, Inc. (2011).
Exhibit 2021, filed May 5, 2014 in connection with IPR2013-00517: Lee et al., "Unwinding of double-stranded DNA helix by dehydration" PNAS 78:2838-42 (1981).

Exhibit 2021, filed Oct. 24, 2013 in connection with IPR2013-100128: Metzker, "Termination of DNA synthesis by novel 3'-modified deoxyribonucleoside 5'-triphosphates", Nucleic Acids Research 22(20): 4259-4267 (1994).
Exhibit 2022, filed Dec. 30, 2013 in connection with IPR2013-00266: Pages from Handbook of Reagents for Organic Synthesis: Reagents for Silicon-Mediated Organic Synthesis (Philip L. Fuchs, ed.) (2011).
Exhibit 2022, filed Jun. 24, 2013 in connection with IPR2012-00006: Sep. 16, 2012 Petition for Inter Partes Review of U.S. Pat. No. 7,713,698 (Paper 3 in IPR2012-00006).
Exhibit 2022, filed May 5, 2014 in connection with IPR2013-00517: Christensen et al., "Specific Chemical Synthesis of Ribonucleoside O-Benzyl Ethers" J. Am. Chem. Soc., 37:3398 (1972).
Exhibit 2022, filed Oct. 24, 2013 in connection with IPR2013-00128: Welch & Burgess, Nucleosides and Nucleotides, 18:197-201 (1999).
Exhibit 2023, filed Dec. 30, 2013 in connection with IPR2013-00266: Eric Vermaas Declaration—Redacted version.
Exhibit 2023, filed Jun. 24, 2013 in connection with IPR2012-00006: Sep. 16, 2012 Petition for Inter Partes Review of U.S. Pat. No. 7,790,869 (Paper 5 in IPR2012-00007).
Exhibit 2023, filed May 5, 2014 in connection with IPR2013-00517: Watkins et al., "Synthesis of Oligodeoxyribonucleotides Using N-Benzyloxycarbonyl-Blocked Nucleosides", J. Am. Chem, Soc. 104:5702-08 (1982).
Exhibit 2023, filed Oct. 24, 2013 in connection with IPR2013-00128: Jun. 4, 2013 Declaration of Bruce Branchaud, Ph.D. in IPR2013-00324.
Exhibit 2024, filed Dec. 30, 2013 in connection with IPR2013-00266: Excerpts from Oct. 3, 2013 Bruce Branchaud Deposition Transcript in IPR2013-00128.
Exhibit 2024, filed Jun. 24, 2013 in connection with IPR2012-00006: Maxam and Gilbert (1977) A new method for sequencing DNA, Proc. Natl. Acad. Sci. USA. 74:560-564.
Exhibit 2025, filed Jun. 24, 2013 in connection with IPR2012-00006: Sanger et al. (1977) DNA sequencing with chain-terminating inhibitors, Proc. Natl. Acad. Sci. USA. 74:5463-5467.
Exhibit 2025, filed May 5, 2014 in connection with IPR2013-00517: Yoshimoto et al., "Tris(2,4,6-trimethoxyphenyl)phosphine (TTMPP): A Novel Catalyst for Selective Deacetylation" Chemistry Letters 30:934-35 (2001).
Exhibit 2025, filed Oct. 24, 2013 in connection with IPR2013-00128: U.S. Pat. No. 7,057,026 file history.
Exhibit 2026, filed Dec. 30, 2013 in connection with IPR2013-00266: Prober et al., Science 238:336-341 (1987).
Exhibit 2026, filed Jun. 24, 2013 in connection with IPR2012-00006:Pennisi (2000) DOE Team Sequences Three Chromosomes, Science. 288:417-419.
Exhibit 2026, filed May 5, 2014 in connection with IPR2013-00517: Chapter 3 of Protective Groups in Organic Synthesis (Theodora W. Greene & Peter G. M. Wuts eds., John Wiley & Sons, Inc. 3rd ed. 1999) (1991).
Exhibit 2026, filed Oct. 24, 2013 in connection with IPR2013-00128: Maxam and Gilbert, "A New Method for Sequencing DNA" 74:560-564, PNAS (1977).
Exhibit 2027, filed Dec. 30, 2013 in connection with IPR2013-59800266: CEQ 2000 DNA Analysis System User's Guide, Beckman Coulter (Jun. 2000).
Exhibit 2027, filed Jun. 24, 2013 in connection with IPR2012-00006: Welch and Burgess (1999) Synthesis of Fluorescent, Photolabile 3'- O-Protected nucleoside Triphosphates for the Base Addition Sequencing Scheme, nucleosides & Nucleotides, 18:197-201.
Exhibit 2027, filed May 5, 2014 in connection with IPR2013-00517:Bentley et al., "Accurate whole human genome sequencing using reversible terminator chemistry" Nature 456: 53-59 (2008).
Exhibit 2028, filed Feb. 19, 2014 in connection with IPR2013-00128: Substitute Declaration of Eric Vermaas Accompanying Patent Owner's Motion To Amend.
Exhibit 2028, filed Jun. 24, 2013 in connection with IPR2012-00006: Hyman (1998) A New Method of Sequencing DNA, Analytical Biochemistry 174:423-436.

(56) References Cited

OTHER PUBLICATIONS

Exhibit 2029, filed Feb. 24, 2014 in connection with IPR2013-00128: Supplementary information for Ex. 1032 (Mitra et al., Analytical Biochem. 320, 55-65, 2003).
Exhibit 2029, filed May 5, 2014 in connection with IPR2013-00517: Shendure et al., "Advanced Sequencing Technologies: Methods and Goals" Nature Reviews Genetics, 5:335-44 (2004).
Exhibit 2030, filed Jun. 24, 2013 in connection with IPR2012-00006: Canard and Sarfati (1994) DNA polymerase fluorescent substrates with reversible 3'-tags, Gene. 148:1-6.
Exhibit 2030, filed Mar. 21, 2014 in connection with IPR2013-00266: Mar. 11, 2014 Bruce Branchaud Deposition Transcript.
Exhibit 2031, filed Feb. 24, 2014 in connection with IPR2013-00128: Ju et al., "Four-color DNA 15 Sequencing By Synthesis Using Cleavable 16 Fluorescent Nucleotide Reversible Terminators," PNAS USA, 103:19635-19640 (2006).
Exhibit 2032, filed Feb. 24, 2014 in connection with IPR2013-00128: ScanArray Express Line of Microarray Scanners—Brochure.
Exhibit 2032, filed Jun. 24, 2013 in connection with IPR2012-00006: Sarfati et al. (1987) Synthesis of Fluorescent or Biotinylated Nucleoside Compounds, Tetrahedron Letters. 43:3491-3497.
Exhibit 2032, filed Mar. 21, 2014 in connection with IPR2013-00266: Excerpts from Feb. 11, 2014 Bruce Branchaud Deposition Transcript in related IPR2013-00128.
Exhibit 2033, filed Aug. 30, 2013 in connection with IPR2012-00006: Jun. 25, 2013 Substitute Declaration of Dr. George L. Trainor [redacted].
Exhibit 2033, filed Aug. 30, 2013 in connection with IPR2012-00007: Jun. 25, 2013 Substitute Declaration of Dr. George L. Trainor [redacted].
Exhibit 2033, filed Aug. 30, 2013 in connection with IPR2013-00011: Jun. 25, 2013 Substitute Declaration of Dr. George L. Trainor [redacted].
Exhibit 2034, filed Feb. 24, 2014 in connection with IPR2013-00128: Feb. 11, 2014 Second Deposition Transcript of Bruce Branchaud, Ph.D.
Exhibit 2034, filed Jun. 25, 2013 in connection with IPR2012-00006: Jingyue Ju et al. (2006) Four-color DNA sequencing by synthesis using cleavable fluorescent nucleotide reversible terminators, Proceedings of the National Academy of Sciences. 103: 19635-19640.
Exhibit 2034, filed Mar. 21, 2014 in connection with IPR2013-00266: ScanArray Express Line of Microarray Scanners—Brochure.
Exhibit 2035, filed Jun. 25, 2013 in connection with IPR2012-00006: Batista et al. (2008) PRG-1 and 210-RNAs Interact to Form the piRNA Complex Required for Fertility in C. elegans. Molecular Cell 31:1-12.
Exhibit 2036, filed Jun. 25, 2013 in connection with IPR2012-00006: Form 7 Review Context and Analysis, Biomedical Engineering and Research to Aid Persons with Disabilities Programs Dec. 19-20, 2000 Panel Review, Fluorescence Imaging Chip System for Massive Parallel DNA Sequencing. Proposal No. BES-0097793.
Exhibit 2036, filed Mar. 21, 2014 in connection with IPR2013-00266: Supplementary information for Ex. 1020 (Mitra et al., Analytical Biochem. 320, 55-65, 2003).
Exhibit 2037, filed Feb. 24, 2014 in connection with IPR2013-00128: Mullis et al., "Specific Synthesis of DNA in Vitro via a Polymerase-Catalyzed Chain Reaction," pp. 335-350, in Methods in Enzymology, vol. 155, Recombinant DNA, Part F, ed. Wu, Academic Press, Inc., San Diego (1987).
Exhibit 2037, filed Jun. 25, 2013 in connection with IPR2012-00006; Oct. 1, 2006 Request for opinion on manuscript by J. Ju et. al., Proceedings of National Academy of Sciences, U.S.A.
Exhibit 2038, filed Feb. 24, 2014 in connection with IPR2013-00128: Brown et al., "Modern machine-aided methods of oligodeoxyribonucleotide synthesis," pp. 1-11; and Ruth, "Oligodeoxynucleotides with reporter groups attached to the base," p. 255, in Oligonucleotides and Analogues, A Practical Approach, ed. Eckstein, Oxford Univ. Press, New York (1991).
Exhibit 2038, filed Jun. 25, 2013 in connection with IPR2012-00006: Correspondence between George Rupp, Chancellor, Columbia University and Richard T. Schlossberg, President, The David and Lucile Packard Foundation (2001).
Exhibit 2038, filed Mar. 21, 2014 in connection with IPR2013-00266: Dawson and Herman et al., "Affinity Isolation of Active Murine Erythroleukemia Cell Chromatin: Uniform Distribution of Ubiquitinated Histone H2A Between Active and Inactive Fractions" Journal of Cellular Biochemistry 46:166-173 (1991).
Exhibit 2039, filed Feb. 24, 2014 in connection with IPR2013-00128: Dawson and Herman et al., "Affinity isolation of active murine erythroleukemia cell chromatin: Uniform distribution of ubiquitinated histone H2A between active and inactive fractions", Journal of Cellular Biochemistry 46:166-173 (1991).
Exhibit 2039, filed Jun. 25, 2013 in connection with IPR2012-00006: The David and Lucile Packard Foundation, Packard Fellowships for Science and Engineering, http://www.packard.org/whatwefund/conservation-and-science/packard-fellowships-for-scienceandengineering/ (last visited Jun. 25, 2013).
Exhibit 2039, filed Mar. 21, 2014 in connection with IPR2013-00266: Rigas et al., "Rapid plasmid library screening using RecA-coated biotinylated probes" PNAS USA 83: 9591-9595 (1986).
Exhibit 2039, filed May 5, 2014 in connection with IPR2013-00517: Transcript of Apr. 8, 2014 Deposition of Bruce Branchaud, Ph. D.
Exhibit 2040, filed Feb. 24, 2014 in connection with IPR2013-00128: Rigas et al., "Rapid plasmid library screening using RecA-coated biotinylated probes," PNAS USA 83;9591-9595 (1986).
Exhibit 2040, filed Jun. 25, 2013 in connection with IPR2012-00006: "Chemistry for Next-Generation Sequencing." http://www.illumina.com/technology/sequencing_technology.ilmn.
Exhibit 2041, filed Feb. 24, 2014 in connection with IPR2013-00128: U.S. Pat. No. 4,888,274, dated Dec. 19, 1989 to Radding et al.
Exhibit 2041, filed Jun. 25, 2013 in connection with IPR2012-00006; Chiang et al. (2010) Mammalian microRNAs: experimental evaluation of novel and previously annotated genes, Genes & Dev. 24:992, 993.
Exhibit 2041, filed Mar. 21, 2014 in connection with IPR2013-00266: Westheimer et al., "Why Nature Chose Phosphates" Science 235:1173-1178 (1987).
Exhibit 2042, filed Feb. 24, 2014 in connection with IPR2013-00128: Westheimer et al., "Why nature chose phosphates" Science 235:1173-1178 (1987).
Exhibit 2042, filed Jun. 25, 2013 in connection with IPR2012-00006; Seo et al. (2004) Photocleavable fluorescent nucleotides for DNA sequencing on a chip constructed by site-specific coupling chemistry, Proc. Natl Acad. Sci. 101 (15):5488-5493.
Exhibit 2043, filed Jun. 25, 2013 in connection with IPR2012-00006: Curriculum vitae of Mr. Raymond S. Sims.
Exhibit 2043, filed Mar. 21, 2014 in connection with IPR2013-00266: English translation of Loubinoux et al., "Protection Of Phenols By The Azidomethylene Group Application To The Synthesis Of Unstable Phenols" Tetrahedron, 44:6055-6064 (1988).
Exhibit 2044, filed Jun. 25, 2013 in connection with IPR2012-00006: Prior Testimony of Mr. Raymond S. Sims.
Exhibit 2044, filed Mar. 21, 2014 in connection with IPR2013-00266: Excerpts from Oct. 3, 2013 Bruce Branchaud Deposition Transcript in related Inter Partes Review IPR2013-00128.
Exhibit 2044, filed May 5, 2014 in connection with IPR2013-00517; Excerpts of Transcript of Mar. 20, 2013 Deposition of *Dr. Xiaohai Liu in Columbia* v. *Illumina,* 12-cv-376 (D. Del).
Exhibit 2045, filed Jun. 25, 2013 in connection with IPR2012-00006: Documents reviewed by Mr. Raymond S. Sims in this Proceeding.
Exhibit 2045, filed Mar. 21, 2014 in connection with IPR2013-00266: Welch et al., "Syntheses of Nucleosides Designed for Combinatorial DNA Sequencing" Chem. Eur. J., 5:951-960 (1999).
Exhibit 2046, filed Mar. 21, 2014 in connection with IPR2013-00266: Welch et al., Corrigenda to "Syntheses of Nucleosides Designed for Combinatorial DNA Sequencing" Chem. Eur. J., 11:7145 (2005).

(56) References Cited

OTHER PUBLICATIONS

Exhibit 2047, filed Mar. 21, 2014 in connection with IPR2013-00266: Wu et al., "Termination of DNA synthesis by $N^6$-alkylated, not 3'-0-alkylated, photocleavable 2'-deoxyadenosine triphosphates", Nucleic Acids Research 35:6339-6349 (2007).
Exhibit 2047, filed May 5, 2014 in connection with IPR2013-00517; Ruparel et al., "Design and synthesis of a 3-O-allyl photocleavable fluorescent nucleotide as a reversible terminator for DNA sequencing by synthesis" PNAS 102:5932-5937 (2005).
Exhibit 2048, filed Mar. 21, 2014 in connection with IPR2013-00266: Taylor et al., "Rise per base pair in helices of double-stranded rotavirus RNA determined by electron microscopy" Virus Research, 2:175-182 (1985).
Exhibit 2049, filed Mar. 21, 2014 in connection with IPR2013-00266: Watson et al., Molecular Biology of the Gene, Fifth Edition, Chapter 6 (2004).
Exhibit 2050, filed Mar. 21, 2014 in connection with IPR2013-00266: Shen et al., "RNA structure at high resolution" FASEB J., 9:1023-1033 (1995).
Exhibit 2050, filed May 5, 2014 in connection with IPR2013-00517; Mardis, "A decade's perspective on DNA sequencing technology" Nature 470:198-203 (2011).
Exhibit 2051, filed Mar. 21, 2014 in connection with IPR2013-00266: Holtzman et al., "Electron microscopy of complexes of isolated acetylcholine receptor, biotinyl-toxin, and avidin" Proc. Natl. Acad. Sci. USA, 79:310-314 (1982).
Exhibit 2051, filed May 5, 2014 in connection with IPR2013-00517: Meng et al., "Design and Synthesis of a Photocleavable Fluorescent Nucleotide 3'-O-Allyl-dGTP-PC-Bodipy-FL-510 as a Reversible Terminator for DNA Sequencing by Synthesis" J. Org. Chem 71:3248-52 (2006).
Exhibit 2052, filed Jun. 25, 2013 in connection with IPR2012-00006; Gary Schroth Proof of Chiang Paper.
Exhibit 2052, filed Mar. 21, 2014 in connection with IPR2013-00266: Pugliese et al., "Three-dimensional Structure of the Tetragonal Crystal Form of Egg-white Avidin in its Functional Complex with Biotin at 2.7 Angstrom Resolution" Journal of Molecular Biology, 231:698-710 (1993).
Exhibit 2052, filed May 5, 2014 in connection with IPR2013-00517; Bi et al., "Design and Synthesis of a Chemically Cleavable Fluorescent Nucleotide, 3'-O-Allyl-dGTP-allyl-Bodipy-FL-510, as a Reversible Terminator for DNA Sequencing by Synthesis" J Am Chem Soc, 128:2542-43 (2006).
Exhibit 2053, filed Mar. 21, 2014 in connection with IPR2013-00266: Fersht, "Fidelity of replication of phage φX174 DNA by DNA polymerase III holoenzyme: Spontaneous mutation by misincorporation" Proc. Natl. Acad. Sci. USA, 76:4946-4950 (1979).
Exhibit 2053, filed May 5, 2014 in connection with IPR2013-00517; Meng, "Tandem Aldol-Allylation Reactions Promoted by Strained Silacycles and Design and Synthesis of Modified Fluorescent Nucleotides for DNA Sequencing by Synthesis", Student Thesis (2006).
Exhibit 2054, filed Mar. 21, 2014 in connection with IPR2013-00266: Fersht et al., "DNA polymerase accuracy and spontaneous mutation rates: Frequencies of purine-purine, purine-pyrimidine, and pyrimidine-pyrimidine mismatches during DNA replication" Proc. Natl. Acad. Sci. USA, 78:4251-4255 (1981).
Exhibit 2054, filed May 5, 2014 in connection with IPR2013-00517: Wu et al., "3'-O-modified nucleotides as reversible terminators for pyrosequencing" PNAS, 104:16462-67 (2007).
Exhibit 2055, filed Mar. 21, 2014 in connection with IPR2013-00266: Bebenek et al., "Frameshift errors initiated by nucleotide misincorporation" Proc. Natl. Acad. Sci. USA, 87:4946-4950 (1990).
Exhibit 2055, filed May 5, 2014 in connection with IPR2013-00517: Kim, "Four-Color DNA Sequencing by Synthesis on a Chip Using Cleavable Fluorescent Nucleotide Reversible Terminators", Student Thesis (2008).

Exhibit 2056, filed Mar. 21, 2014 in connection with IPR2013-00266: Bebenek et al., "The Effects of dNTP Pool Imbalances on Frameshift Fidelity during DNA Replication" J. Biol. Chem., 267:3589-3596 (1992).
Exhibit 2056, filed May 5, 2014 in connection with IPR2013-00517; Wu, "Molecular Engineering of Novel Nucleotide Analogues for DNA Sequencing By Synthesis", Student Thesis (2008).
Exhibit 2057, filed Mar. 21, 2014 in connection with IPR2013-00266: Greene and Wuts, Protective Groups in Organic Synthesis, 3rd ed., Chapter 1 (1999).
Exhibit 2057, filed May 5, 2014 in connection with IPR2013-00517: Zhang, "Development of New DNA Sequencing Approaches and Investigation of Vision-related Proteins Using Synthetic Chemistry", Student Thesis (2008).
Exhibit 2058, filed May 5, 2014 in connection with IPR2013-00517: Guo et al., "Four-color DNA sequencing with 3'-O-modified nucleotide reversible terminators and chemically cleavable fluorescent dideoxynucleotides", PNAS 105:9145.
Exhibit 2059, filed May 5, 2014 in connection with IPR2013-00517: Guo, "Molecular Engineering of Novel Nucleotide Analogues for DNA Sequencing and Analysis", Student Thesis (2009).
Exhibit 2060, filed May 22, 2014 in connection with IPR2013-00266: Patentee Demonstratives for May 28, 2014 Oral Hearing.
Exhibit 2060, filed May 5, 2014 in connection with IPR2013-00517; Yu, "Novel Strategies To Increase Read Length And Accuracy For DNA Sequencing By Synthesis", Student Thesis (2010).
Exhibit 2062, filed May 5, 2014 in connection with IPR2013-00517; Qui, "Novel Molecular Engineering Approaches for Genotyping and DNA Sequencing", Student Thesis (2010).
Exhibit 2073, filed May 5, 2014 in connection with IPR2013-00517: Kraevskii et al., "Substrate Inhibitors of DNA Biosynthesis", Molecular Biology 21:25-29 (1987).
Exhibit 2074, filed Jun. 25, 2013 in connection with IPR2012-00006; Information about Dr. Ju's intellectual property sent to Illumina.
Exhibit 2074, filed May 5, 2014 in connection with IPR2013-00517; Dantas et al., "Stannous chloride mediates single strand breaks in plasmid DNA through reactive oxygen species formation", Toxicology Ltrs. 110:129-36 (1999).
Exhibit 2077, filed May 5, 2014 in connection with IPR2013-00517; Burgess et al., "An Approach to Photolabile, Fluorescent Protecting Groups", J. Org. Chem 62: 5165-68 (1997).
Exhibit 2079, filed May 5, 2014 in connection with IPR2013-00517: Welch et al., "Syntheses of Nucleosides Designed for Combinatorial DNA Sequencing", Chem. Eur. J. 5:951-60 (1999).
Exhibit 2090, filed Jun. 26, 2013 in connection with IPR2012-00006; IPR Default Protective Order.
Exhibit 2091, filed Jun. 26, 2013 in connection with IPR2012-00006: Declaration of Raymond S. Sims.
Exhibit 2092, filed Oct. 10, 2013 in connection with IPR2012-00006: Rough Transcript of the Sep. 4, 2013 deposition of Dr. George L. Trainor.
Exhibit 2093, filed Oct. 1, 2013 in connection with IPR2012-00006: Excerpt from Protective Groups in Organic Synthesis, 3rd Ed. (Theodora W. Greene and Peter G.M. Wuts ed., John Wiley & Sons, Inc. 1999).
Exhibit 2094, filed Oct. 1, 2013 in connection with IPR2012-00006: Final transcript of the Sep. 4-6, 2013 deposition of Dr. George L. Trainor.
Exhibit 2095, filed Oct. 1, 2013 in connection with IPR2012-00006: Final transcript of the Sep. 3, 2013 deposition of Raymond S. Sims.
Exhibit 2099, filed Nov. 12, 2013 in connection with IPR2012-00006: Welch, M., et al.(2005) Corrigenda to Syntheses of Nucleosides Designed for Combinatorial DNA Sequencing Chem. Eur.J., 1999, 951-960. Published in Chem. Eur. J, 2005, 11, 7136-7145.
Exhibit 2100, filed Nov. 12, 2013 in connection with IPR2012-00006: Welch, M (1999) "Base Additions Sequencing Scheme (BASS) and Studies Toward New Sequencing Methodologies." PhD. Dissertation, Texas A&M University.
Exhibit 2101, filed Nov. 12, 2013 in connection with IPR2012-100006: Lu and Burgess (2006) "A Diversity Oriented Synthesis of

(56) References Cited

OTHER PUBLICATIONS

3'-O-modified nucleoside triphosphates for DNA 'Sequencing by Synthesis'." Bioorganic & Medicinal Chemistry Letters, 16, 3902-3905.

Exhibit 2102, filed Nov. 12, 2013 in connection with IPR2012-00006: Advanced Sequencing Technology Awards 2004. http://www.genome.gov/12513162 (accessed Oct. 14, 2013).

Exhibit 2103, filed Nov. 12, 2013 in connection with IPR2012-00006: Welch and Burgess (2006) Erratum to Synthesis of Fluorescent, Photolabile 3'-O-Protected Nucleoside Triphosphates for the Base Addition Sequencing Scheme, Nucleosides & Nucleotides, 18:197-201. Published in Nucleosides, Nucleotides and Nucleic Acids, 25:1, 119.

Exhibit 2105, filed Dec. 15, 2013 in connection with IPR2012-00006: Columbia's Demonstratives Under 42.70(b) for Dec. 17, 2013 Oral Hearing in connection with IPR2012-00006, IPR2012-00007, and IPR2013-00011.

Exhibit 2139, filed Sep. 2, 2014 in connection with IPR2013-00517: Metzker, "Sequencing Technologies—The Next Generation" Nature Reviews Genetics, 11:31-46 (2010).

Exhibit 2140, filed Sep. 2, 2014 in connection with IPR2013-00517: Tsai et al., "Versatile and Efficient Synthesis of a New Class of Aza-Based Phosphinic Amide Ligands via Unusual P-C Cleavage" Helvetica Chimica Acta, 89: 3007-3017 (2006).

Exhibit 2141, filed Sep. 2, 2014 in connection with IPR2013-00517: Treinin, General and Theoretical Aspects, Chapter 1 (pp. 1-55) in The Chemistry of the Azido Group (Saul Patai, Ed. ) (1971).

Exhibit 2142, filed Sep. 2, 2014 in connection with IPR2013-00517: Hanlon, "The Importance of London Dispersion Forces in the Maintenance of the Deoxyribonucleic Acid Helix" Biochemical and Biophysical Research Communications, 23:861-867 (1966).

Exhibit 2144, filed Sep. 2, 2014 in connection with IPR2013-00517: "Phenol," in The Merck Index, pp. 1299-1300 (13th Ed., 2001).

Exhibit 2146, filed Sep. 2, 2014 in connection with IPR2013-100517: Metzker, "Emerging technologies in DNA sequencing" Genome Research, 15:1767-1776, (2005).

Exhibit 2147, filed Sep. 2, 2014 in connection with IPR2013-00517: Gardner et al., "Rapid incorporation kinetics and improved fidelity of a novel class of 3'-OH unblocked reversible terminators" Nucleic Acids Research, 40:7404-7415 (2012).

Exhibit 2148, filed Sep. 2, 2014 in connection with IPR2013-695100517: Lander et al., "Initial sequencing and analysis of the human genome" Nature, 409:860-921 (2001).

Exhibit 2149, filed Sep. 2, 2014 in connection with IPR2013-00517: Wu et al., "Termination of DNA synthesis by $N^6$-alkylated, not 3'-O-alkylated, photocleavable 2' -deoxyadenosine triphosphates" Nucleic Acids Research, 35: 6339-6349 (2007).

Exhibit 2150, filed Sep. 2, 2014 in connection with IPR2013-00517: Aldrich, Fine Chemicals catalogue, p. 1337 (1986).

Exhibit 2151, filed Sep. 2, 2014 in connection with IPR2013-00517: Sebastian et al., "Dendrimers with N, N-DisubstitutedHydrazines as End Groups, Useful Precursors for the Synthesis of Water-Soluble Dendrimers Capped with Carbohydrate, Carboxylic or Boronic Acid Derivatives" Tetrahedron, 56:6269-6277 (2000).

Exhibit 2152, filed Sep. 2, 2014 in connection with IPR2013-00517: Reardon et al., "Reduction of 3'-Azido-3'-deoxythymidine (AZT) and AZT Nucleotides by Thiols" The Journal of Biological Chemistry, 269:15999-16008 (1994).

Exhibit 2154, filed Sep. 2, 2014 in connection with IPR2013-70000517: Transcript, Aug. 12, 2014 Deposition of Michael L. Metzker, Ph.D.

Exhibit 2155, filed Sep. 2, 2014 in connection with IPR2013-100517: Transcript, Aug. 26, 2014 Deposition of Bruce P. Branchaud, Ph.D.

Exhibits 1006-1007, filed Aug. 19, 2013 in connection with IPR2013-00517: English translation of Loubinoux et al., Protection of Phenols by the Azidomethylene Group Application to the Synthesis of Unstable Phenols, 44 Tetrahedron 6055 (1988), and Translation Affidavit.

Exhibits 1037 and 1038, filed Jul. 28, 2014 in connection with IPR2013-00517: Knouzi et al., Reductions of Azides by Triphenylphosphine in the presence of water: a General and chemoselective method of access to primary amines, Bull. Soc. Chim. Fr., 1-12 (1985), and translation.

Exhibits 2004, 2005, and 2028, filed Dec. 30, 2013 in connection with IPR2013-00266: Floyd Romesburg Declaration, CV, and List of Documents Considered by Romesburg.

Extended European Search Report dated Jul. 18, 2007 in connection with European Patent Application No. 07004522.4.

Fallahpour, R.A. (2000) "Photochemical and Thermal reactions of Azido-Oligopyridines: Diazepinones, a New Class of Metal-Complex Ligands," Helvetica Chimica Acta. 83:384-393.

Feb. 10, 2014 Record of Dec. 17, 2013 Oral Hearing in connection with IPR2012-00006, IPR2012-00007, and IPR2013-00011.

Feb. 13, 2014 Decision of Institution of Inter Partes Review IPR2013-00517.

Feb. 13, 2014 Decision of Institution of Inter Partes Review IPR2013-00518.

Feb. 19, 2014 Substitute Motion To Amend Under 37 C.F.R. §42.121 in connection with IPR2013-00128.

Feb. 24, 2014 Patent Owner Illumina's Reply To Petitioner's Opposition To Illumina's Motion To Amend.

Feb. 7, 2013 Revised Petition for Inter Partes Review of U.S. Pat. No. 7,057,026.

Fei, Z. et al. (1998) "MALDI-TOF mass spectrometric typing of single nucleotide polymorphisms with mass-tagged ddNTPs," Nucleic Acids Research 26(11):2827-2828.

Finzi, L. et al. (1995) "Measurement of Lactose Repressor-Mediated Loop Formation and Breakdown in Single DNA Molecules." Science, 267:378-380.

Fu, D.J., Tang, K., Braun, A., Reuter, D., Darnhofer-Demar, B., Little, D.P., O'Donnell, M.J., Cantor, C. R., and Koster, H. (1998) "Sequencing exons 5 to 8 of the p53 gene by MALDI-TOF mass spectrometry," Nat. Biotechnol. 16:381-384.

Gibson, K.J. et al. (1987) "Synthesis and Application of Derivatizable Oligonucleotides," Nucleic Acids Research, 15(16):6455-6467.

Godovikova, T.S. et al. (1999) "5-[3- (E)-(4-Azido-2,3,5,6,-(tetrafluorobenzamido)propenyl-1]-2'deoxyuridine-5'-triphosphate Substitutes for Thymidine-5'triphosphate in the Polymerase Chain Reaction, " Bioconjugate Chem., 10: 529-537.

Green, T.W. et al. and Wuts, P.G.M. "Protective Groups in Organic Synthesis" 3rd ed. New York: John Wiley & Sons, Inc. , 1999. 96-99, 190-191, 260-261, 542-543, and 750-751.

Griffin, T.J. et al. (1999) "Direct Genetic Analysis by Matrix-Assisted Laser Desorption/Ionization Mass Spectrometry," Proc. Nat. Acad. Sci. USA 96:6301-6306.

Guibé (1997) "Allylic Protecting Groups and Their Use in a Complex Environment Part I: Allylic Protection of Alcohols," Tetrahedron, 53:13509-13556.

Guibé (1998) "Allylic Protecting Groups and Their Use in a Complex Environment Part II: Allylic Protecting Groups and their Removal through Catalytic Palladium n-Allyl Methodology," Tetrahedron, 54:2967-3042.

Hacia J.G., Edgemon K., Sun B., Stern D., Fodor S. A., and Collins F.S. (1998) "Two Color Hybridization Analysis Using High Density Oligonucleotide Arrays and Energy Transfer Dyes," Nucleic Acids Res. 26:3865-6.

Haff L.A., et al. (1997) "Multiplex Genotyping of PCR Products with Mass Tag-Labeled Primers," Nucleic Acids Res. 25(18):3749-3750.

Hafliger, D. et al. (1997) "Seminested RT-PCR Systems for Small Round Structured Viruses and Detection of Enteric Viruses in Seafood," International Journal of Food Microbiology 37:27-36.

Hanshaw et al. (2004) "An Indicator Displacement System for Fluorescent Detection of Phosphate Oxyanions Under Physiological Conditions," Tetrahedron Letters, vol. 45, pp. 8721-8724.

Hayakawa et al. (1993) "O-Allyl Protection of Guanine and Thymine Residues in Oligodeoxyribonucleotides," J. Org. Chem. , 58:5551-5555.

(56) References Cited

OTHER PUBLICATIONS

Henner, W.D. et al. (1983) "Enzyme Action at 3' Termini of Ionizing Radiation-Induced DNA Strand Breaks," J. Biol. Chem. 258(24):15198-15205.
Hovinen et al. (1994) "Synthesis of 3'-O-(ω-Aminoalkoxymethyl) thymidine 5'-Triphosphates, Terminators of DNA Snythesis that Enable 3'-Labelling," J. Chem. Soc. Perkin Trans., 1:211-217.
Hu et al. (1999) "Optical Mapping of DNA Polymerase I Action and Products," BBRC, 254:466-473.
Huang, B.G. et al. "Synthesis and in vitro Antitumor Activity of Some Amino-deoxy 3-hexofuranosylpyrrolo [2,3-d]pyrimidines." Carbohydrate Research, 1998, 308(3-4):319-328.
Huber et al. (1999) "Monitoring Solid Phase Synthesis By Infrared Spectroscopic Techniques." Analytica Chimica Acta, 393:213.
Hultman et al. (1989) "Direct Solid Phase Sequencing of Genomic and Plasmid DNA Using Magnetic Beads as Solid Support," Nucleic Acids Research 17(3):4937-4946.
Hyman ED, (1988) "A new method of sequencing DNA". Analytical Biochemistry 174:423-436.
Ikeda, K. et al. (1995) "A Non-Radioactive DNA Sequencing Method Using Biotinylated Dideoxynucleoside Triphosphates and Delta TTH DNA Polymerase," DNA Research 2(31):225-227.
International Preliminary Examination Report dated Feb. 25, 2003 in connection with PCT/US01/28967.
International Preliminary Examination Report dated Jun. 13, 2003 in connection with PCT/US01/31243.
International Preliminary Examination Report dated Mar. 17, 2003 in connection with PCT/US02/09752.
International Preliminary Examination Report dated Mar. 18, 2005 in connection with PCT/US03/21818.
International Preliminary Report on Patentability dated Sep. 5, 2006 in connection with PCT/US05/06960.
International Preliminary Report on Patentability, dated Jun. 11, 2009 in connection with International Application No. PCT/US07/24646.
International Search Report issued by the International Searching Authority (ISA/US) dated Aug. 12, 2008 in connection with International Application No. PCT/US07/24646.
International Search Report dated Dec. 15, 2006 in connection with PCT/US05/13883.
International Search Report dated Jan. 23, 2002 in connection with PCT/US01/28967.
International Search Report dated Jun. 8, 2004 in connection with PCT/US03/39354.
International Search Report dated May 13, 2002 in connection with PCT/US01/31243.
International Search Report dated Nov. 4, 2005 in connection with PCT/US05/06960.
International Search Report dated Oct. 29, 2007 in connection with PCT International Application No. PCT/US07/13559.
International Search Report dated Sep. 18, 2002 in connection with PCT/US02/09752.
International Search Report dated Sep. 26, 2003 in connection with PCT/US03/21818.
Ireland, R.E. and Varney, M. D. (1986) "Approach to the total synthesis of chlorothricolide: synthesis of (±)—19.20-dihydro-24-O-methylchlorothricolide, methyl ester, ethyl carbonate," J. Org. Chem. 51:635-648.
Jan. 24, 2014 Intelligent Bio-Systems Opposition to Illumina's Motion to Amend in connection with IPR2013-00128.
Jan. 29, 2013 Petition for Inter Partes Review of U.S. Pat. No. 7,057,026.
Jan. 7, 2013 Preliminary Response under 37 C.F.R. 42.107 in connection with IPR2013-00011.
Jiang-Baucom, P. et al. (1997) "DNA Typing of Human Leukocyte Antigen Sequence Polymorphisms by Peptide Nucleic Acid Probes and MALDI-TOF Mass Spectrometry," Anal. Chem. 69:4894-4896.
Ju J., et al. (1996) "Cassette labeling for facile construction of energy transfer fluorescent primers." Nucleic Acids Res. 24(6):1144-1148.
Ju J., et al. "Four-color DNA sequencing by synthesis using cleavable fluorescent nucleotide reversible terminators." Proc Natl Acad Sci U S A. Dec. 26, 2006;103(52):19635-40, Epub Dec. 14, 2006.
Ju J., Glazer, A.N., and Mathies, R.A. (1996) "Energy transfer primers: A new fluorescence labeling paradigm for DNA sequencing and analysis." Nature Medicine 2: 246-249.
Ju J., Ruan C., Fuller, C.W., Glazer, A.N., and Mathies, R.A. (1995) "Fluorescence energy transfer dye-labeled primers for DNA sequencing and analysis." Proc. Natl. Acad. Sci. USA 92: 4347-4351.
Jul. 16, 2010 Amendment in response to Office Action dated Feb. 18, 2010 in connection with U.S. Appl. No. 12/312,903.
Jul. 25, 2014 Final Written Decision in connection with IPR2013-00128.
Jul. 29, 2013 Decision on Petition for Inter Partes Review in connection with IPR2013-00128.
Jun. 25, 2013 Motion to Amend Under 37 C.F.R. 42.121 in connection with IPR2013-00011.
Jun. 4, 2013 Petition for Inter Partes Review of U.S. Pat. No. 7,057,026.
Jurinke, C., van de Boom, D., Collazo, V., Luchow, A., Jacob, A., and Koster H, (1997) "Recovery of nucleic acids from immobilized biotin-streptavidin complexes using ammonium hydroxide and application in MALDI-TOF mass spectrometry," Anal. Chem, 69:904-910.
Kamal, A., Laxman, E., and Rao, N. V. (1999) "A mild and rapid regeneration of alcohols from their allylic ethers by chlorotrimethylsilane/sodium iodide," Tetrahedron Lett 40:371-372.
Kan, C.W.; Doherty, E. A. S.; Barron, A. E. (2003) "A novel thermogelling matrix for microchannel DNA sequencing based on poly-N-alkoxyalkylacrylamide copolymers." Electrophoresis, 24, pp. 4161-4169.
Kasianowicz, J.J., Brandin, B., Branton, D. and Deamer, D.W. "Characterization of individual polynucleotide molecules using a membrane channel." Proc. Natl. Acad. Sci. USA 1996, 93, 13770-13773.
Kim Sobin et al. (2002) "Solid Phase Capturable Dideoxynucleotides for Multiplex Genotyping Using Mass Spectrometry, " Nucleic Acids Research 30(16):e85.1-e85.6.
Kim, S. et al. (2003) "Multiplex Genotyping of the Human Beta2-adrenergic Receptor Gene Using Solid-phase Capturable Dideoxynucleotides and Mass Spectrometry," Analytical Biochemistry 316:251-258.
Kimzey A.L. et al. (1998) "Specific Regions of Contact Between Human T-cell Leukemia Virus Type I Tax Protein and DNA Identified By Photocross-linking," Journal of Biological Chemistry, 273(22):13768-13775.
Kitamura et al. (2002) "(P(C6H5)3) CpRu+Catalyzed Deprotection of Allyl Carboxylic Esters," J. Org. Chem., 67:4975-4977.
Kloosterman et al. (1985) "The relative stability of allyl ether, allyloxycarbonyl ester and prop-2 enylidene acetal, protective groups toward Iridium, Rhodium and Palladium catalysts," Tetrahedron Letters, 26:5045-5048.
Kokoris, M. et al. (2000) "High-throughput SNP Genotyping With the Masscode System," Molecular Diagnosis 5(4):329-340.
Kolb et al. (2001) "Click Chemistry: Diverse Chemical Function From a Few Good Reactions," Angew. Chem. Int. Ed. 40:2004-2021.
Kraevskii, A.A. et al. (1987) "Substrate Inhibitors of DNA Biosynthesis,"Molecular Biology 21:25-29.
Krečmerová (1990) "Synthesis of 5'-O-Phosphonomethyl Derivatives of Pyrimidine 2'-Deoxynucleosides." Coll. Czech. Chem. Commun., 55:2521-2536.
Kurata et al. (2001) "Fluorescent quenching-based quantitative detection of specific DNA/RNA using BODIPY® FL-labeled probe of primer," Nucleic Acids Research, vol. 29, No. 6, p. e34.
Kvam et al., (1994) "Characterization of singlet oxygen-induced guanine residue damage after photochemical treatment of free nucleosides and DNA," Biochemica et Biophysica Acta., 1217:9-15.
Lee, L.G. et al., (1997) "New energy transfer dyes for DNA sequencing," Nucleic Acids Res. 25:2816-2822.

(56) References Cited

OTHER PUBLICATIONS

Lee, L.G., et al. (1992) "DNA sequencing with dye labeled terminators and T7 DNA polymerase effect of dyes and dNTPs on incorporation of dye terminators and probability analysis of termination fragments," Nucleic Acids Res. 20:2471-2483.
Leroy, E.M. et al. (2000) "Diagnosis of Ebola Haemorrhagic Fever by RT-PCR in an Epidemic Setting," Journal of Medical Virology 60:463-467.
Lewis et al. (2002) "Click Chemistry in Situ: Acetylcholinesterase as a Reaction Vessel for the Selective Assembly of a Femtomolar Inhibitor from an Array of Building Blocks," Angew. Chem. Int. Ed. 41(6):1053-1057.
Li, J. (1999) "Single Oligonucleotide Polymorphism Determination Using Primer Extension and Time-of-Flight Mass Spectrometry," Electrophoresis 20:1258-1265.
Li, Z., Bai, X., Ruparel, H., Kim, S., Turro, N.J. and Ju, J. A "Photocleavable fluorescent nucleotide for DNA sequencing and analysis." Proc. Natl. Acad. Sci. USA 2003, 100, 414-419.
Liu, H. et al. (2000) "Development of Multichannel Devices with an Array of Electrospray Tips for High-Throughput Mass Spectrometry," Anal. Chem, 72:3303-3310.
Loubinoux, B. et al. "Protection Des Phenols Par Le Groupement Azidomethylene Application A La Synthese De Phenols Instables," Tetrahedron, 1998, 44(19): 6055 (English Abstract Only).
Lu, G. and Burgess, K. (2006) W"A diversity oriented synthesis of 3'-O-modified nucleoside triphosphates for DNA 'sequencing by synthesis'." Bioorg. Med. Chem. Lett., 16, pp. 3902-3905.
Lyamichev, V. et al. (1999) "Polymorphism Identification and Quantitative Detection of Genomic DNA by Invasive Cleavage of Oligonucleotide Probes," Nat. Biotech 17:292-296.
Maier et al. (1995) "Synthesis and Properties of New Fluorescein-Labeled Oligonucleotides," Nucleosides and Nucleotides, 14:961-965.
Mar. 11, 2015 Response to Dec. 8, 2014 Office Action issued in connection with German Patent Application No. 11 2007 002 932.3.
Mar. 12, 2013 Decision on Petition for Inter Partes Review in connection with IPR2012-00006.
Mar. 12, 2013 Decision on Petition for Inter Partes Review in connection with IPR2012-00007.
Mar. 12, 2013 Decision on Petition for Inter Partes Review in connection with IPR2013-00011.
Mar. 18, 2014 Patentee's Motion to Exclude Petitioner's Evidence in connection with IPR2013-00128.
Mar. 18, 2014 Petitioner's Motion to Exclude in connection with IPR2013-00128.
Mar. 21, 2014 Patent Owner's Reply to Petitioner's Opposition to Patent Owner's Motion to Amend in connection with IPR2013-00266.
Mar. 26, 2013 Request for Reconsideration in connection with IPR2012-00006.
Mar. 26, 2013 Request for Reconsideration in connection with IPR2012-00007.
Mar. 26, 2013 Request for Reconsideration in connection with IPR2013-00011.
Mar. 26, 2013 Request for Rehearing under 37 C.F.R. 42.71 of Decision to Institute Inter Partes Review in connection with IPR2012-00007.
Mar. 26, 2013 Request for Rehearing under 37 C.F.R. 42.71 of Decision to Institute Inter Partes Review in connection with IPR2013-00011.
Mar. 29, 2011 Response to Sep. 28, 2010 Communication issued in connection with UK Patent Application No. 0909600.9.
Mar. 6, 2014 Final Written Decision in connection with IPR2012-00006.
Mar. 6, 2014 Final Written Decision in connection with IPR2012-00007.
Mar. 6, 2014 Final Written Decision in connection with IPR2013-00011.

Margulies, M.; Egholm, M.; Altman, W. E.; et al. (2005) "Genome sequencing in microfabricated high-density picolitre reactors." Nature, 437, pp. 376-380.
Markiewicz et al. (1997) "A new method of synthesis of fluorescently labeled oligonucleotides and their application in DNA sequencing," Nucleic Acids Research, 25:3672-3690.
Marquez et al. (2003) "Selective Fluorescence Quenching of 2, 3-Diazabicyclo[2.2.2]oct-2-ene by Nucleotides, " Organic Letters, 5:3911-3914.
Mathews C.K. et al. (1985) "Chemical Synthesis of Oligonucleotides," Biochemistry, 2nd Edition, pp. 127-128.
May 1, 2013 Preliminary Response under 37 C. F.R. 42.107 in connection with IPR2013-00128.
May 10, 2013 Decision on Request for Rehearing in connection with IPR2012-00006.
May 10, 2013 Decision on Request for Rehearing in connection with IPR2012-00007.
May 10, 2013 Decision on Request for Rehearing in connection with IPR2013-00011.
May 2, 2014 Patentee Response to Petitioner Motion for Observations on Romesberg Testimony, in connection with IPR2013-00266.
May 22, 2014 Record of Apr. 23, 2014 Oral Hearing in connection with IPR2013-00128.
May 4, 2013 Petition for Inter Partes Review of U.S. Pat. No. 8,158,346, dated Apr. 17, 2012.
May 5, 2014 Patent Owner Response in connection with IPR2013-00517.
May 5, 2014 Patentee Request for Adverse Judgment in IPR2013-00518.
May 6, 2014 Decision of Adverse Judgment in IPR2013-00518.
May 9, 2012 Response to Office Action dated Nov. 9, 2011 in connection with U.S. Appl. No. 13/023,283.
Meng et al., (2006) "Design and Synthesis of a Photocleavable Fluorescent Nucleotide 3'-O-Allyl-dGTP-PC-Biodipy-FL-510 as a Reversible Terminator for DNA Sequencing by Synthesis." J. Org. Chem 71:3248-3252.
Metzker M. L. (2005) "Emerging technologies in DNA sequencing," Genome Res., 15:1767-1776.
Metzker ML, Raghavachari R, Richards S, Jacutin SE, Civitello A, Burgess K, Gibbs RA. (1994) "Termination of DNA synthesis by novel 3' modified deoxyribonucleoside 5' triphosphates." Nucleic Acids Res. 22: 4259-4267.
Mitra, R. D.; Shendure J.; Olejnik, J.; et al. (2003) "Fluorescent in situ sequencing on polymerase colonies." Anal. Biochem., 320:55-65.
Monforte, J.A. and Becker, C.H. (1997) "High-throughput DNA analysis by time-of-flight mass spectrometry," Nat. Med. 3(3):360-362.
Nazarenko et al. (2002) "Effect of primary and secondary structure of oligodeoxyribonucleotides on the fluorescent properties of conjugated dyes," Nucleic Acids Research, 30:2089-2095.
Nickel et al. (1992) "Interactions of Azidothymidine triphosphate with the Cellular DNA polymerases alpha, delta, and episilon and with DNA Primase," J. Biol. Chem. 267(2):848-854.
Nielsen et al. (2004) "Multiplexed Sandwich Assays in Microarray Format," Journal of Immunological Methods, vol. 290, pp. 107-120.
Nishino et al. (1991) "Efficient Deanilidation of Phosphoranilidates by the Use of Nitrites and Acetic Anhydride." Heteroatom Chemistry, vol. 2, pp. 187-196.
Notice of Abandonment dated Apr. 10, 2014 in connection with U.S. Appl. No. 13/665,588.
Notice of Abandonment dated Nov. 14, 2012 in connection with U.S. Appl. No. 13/339,089.
Notice of Allowance dated Apr. 2, 2010 in connection with U.S. Appl. No. 11/810,509.
Notice of Allowance dated Feb. 24, 2009 in connection with U.S. Appl. No. 11/894,690.
Notice of Allowance dated Jun. 6, 2012 in connection with U.S. Appl. No. 13/023,283.
Notice of Allowance dated Mar. 23, 2009 in connection with U.S. Appl. No. 11/894,808.
Notice of Allowance dated Sep. 1, 2011 in connection with U.S. Appl. No. 12/804,284.

(56) References Cited

OTHER PUBLICATIONS

Notice of Allowance dated Sep. 27, 2010 in connection with U.S. Appl. No. 12/312,903.
Notice of Allowance dated Sep. 6, 2007 in connection with U.S. Appl. No. 10/702,203.
Notification Concerning Transmittal of International Preliminary Report on Patentability (Including Written Opinion of the International Searching Authority) dated May 15, 2008 in connection with PCT/US2006/042698.
Notification of Transmittal of International Search Report and the Written Opinion of the International Searching Authority, or the Declaration dated Sep. 9, 2008 in connection with International Application No. PCT/US06/24157.
Notification of Transmittal of International Search Report and Written Opinion, dated Nov. 23, 2007 in connection with International Application No. PCT/US06/42698.
Notification of Transmittal of International Search Report and Written Opinion, dated Feb. 6, 2008 in connection with International Application No. PCT/US06/42739.
Notification of Transmittal of International Search Report and Written Opinion, dated May 22, 2008 in connection with International Application No. PCT/US06/45180.
Nov. 12, 2013 Patent Owner Motion for Observations on the Cross-Examination Testimony of Kevin Burgess, Ph. D. in connection with IPR2012-00006.
Nov. 12, 2013 Patent Owner Motion for Observations on the Cross-Examination Testimony of Kevin Burgess, Ph. D. in connection with IPR2012-00007.
Nov. 12, 2013 Patent Owner Motion for Observations on the Cross-Examination Testimony of Kevin Burgess, Ph.D. in connection with IPR2013-00011.
Nov. 12, 2013 Patent Owner Motion to Exclude Evidence in connection with IPR2012-00006.
Nov. 12, 2013 Patent Owner Motion to Exclude Evidence in connection with IPR2012-00007.
Nov. 12, 2013 Patent Owner Motion to Exclude Evidence in connection with IPR2013-00011.
Nov. 12, 2013 Petitioner Motion to Exclude Evidence in connection with IPR2012-00006.
Nov. 12, 2013 Petitioner Motion to Exclude Evidence in connection with IPR2012-00007.
Nov. 12, 2013 Petitioner Motion to Exclude Evidence in connection with IPR2013-00011.
Nov. 18, 2013 Substitute Patent Owner Reply on Motion to Amend in connection with IPR2012-00006.
Nov. 18, 2013 Substitute Patent Owner Reply on Motion to Amend in connection with IPR2012-00007.
Nov. 18, 2013 Substitute Patent Owner Reply on Motion to Amend in connection with IPR2013-00011.
Nov. 21, 2013 Decision Denying Institution of Inter Partes Review of U.S. Pat. No. 7,057,026 in connection with IPR2013-00324.
Nov. 26, 2013 Patent Owner Opposition to Petitioner's Motion to Exclude in connection with IPR2012-00006.
Nov. 26, 2013 Patent Owner's Opposition to Petitioner's Motion to Exclude in connection with IPR2012-00007.
Nov. 26, 2013 Patent Owner's Opposition to Petitioner's Motion to Exclude in connection with IPR2013-00011.
Nov. 26, 2013 Petitioner Opposition to Motion to Exclude in connection with IPR2012-00006.
Nov. 26, 2013 Petitioner Response to Motion for Observations in connection with IPR2012-00006.
Nov. 26, 2013 Petitioner's Opposition to Motion to Exclude in connection with IPR2012-00007.
Nov. 26, 2013 Petitioner's Opposition to Motion to Exclude in connection with IPR2013-00011.
Nov. 26, 2013 Petitioner's Response to Motion for Observations in connection with IPR2012-00007.
Nov. 26, 2013 Petitioner's Response to Motion for Observations in connection with IPR2013-00011.
October 24, 2013 Patent Owner Motion to Amend the Patent in connection with IPR2013-00128.
Oct. 28, 2013 Decision Instituting Inter Partes Review in connection with IPR2013-00266.
Oct. 28, 2014 Final Written Decision in connection with IPR2013-00266.
Oct. 3, 2012 Motion to Waive Page Limit and Proposed Petition in connection with Petition for Inter Partes Review of U.S. Pat. No. 8,088,575.
Oct. 3, 2012 Petition for Inter Partes Review of U.S. Pat. No. 8,088,575.
Office Action dated Aug. 10, 2007 in connection with U.S. Appl. No. 11/119,231.
Office Action dated Feb. 18, 2010 in connection with U.S. Appl. No. 12/312,903.
Office Action dated Feb. 4, 2011 in connection with U.S. Appl. No. 12/804,284.
Office Action dated Jul. 8, 2008 in connection with U.S. Appl. No. 10/591,520.
Office Action dated Jun. 24, 2008 in connection with U.S. Appl. No. 11/894,690.
Office Action dated Jun. 5, 2009 in connection with U.S. Appl. No. 11/894,690.
Office Action dated Mar. 14, 2003 in connection with U.S. Appl. No. 09/972,364.
Office Action dated May 8, 2012 in connection with U.S. Appl. No. 13/339,089.
Office Action dated Nov. 14, 2007 in connection with U.S. Appl. No. 10/735,081.
Office Action dated Nov. 9, 2011 in connection with U.S. Appl. No. 13/023,283.
Office Action dated Oct. 1, 2013 in connection with U.S. Appl. No. 13/665,588.
Office Action dated Oct. 25, 2002 in connection with U.S. Appl. No. 09/972,364.
Office Action dated Sep. 21, 2007 in connection with U.S. Appl. No. 10/380,256.
Office Action dated Sep. 3, 2008 in connection with U.S. Appl. No. 11/894,808.
Official Action dated Mar. 14, 2008 in connection with European Patent Application No. 07004522.4.
Official Action dated Mar. 3, 2007 in connection with European Application No. 07004522.4.
Official Action dated Mar. 31, 2006 in connection with European Patent Application No. 01968905.8.
Official Action dated May 21, 2007 in connection with European Patent Application No. 01968905.8.
Olejnik, J. et al. (1995) "Photocleavable biotin derivatives: a versatile approach for the isolation of biomolecules," Proc. Natl. Acad. Sci. USA. 92:7590-7594.
Olejnik, J. et al. (1999) "Photocleavable peptide DNA conjugates: synthesis and applications to DNA analysis using MALDI MS," Nucleic Acids Res. 27:4626-4631.
Partial European Search Report dated Apr. 26, 2007 in connection with European Application No. 07004522.4.
Pastinen et al. (1997) "Minisequencing: A Specific Tool for DNA Analysis and Diagnostics on Oligonucleotide Arrays," Genomic Res., 7:606-614.
Patent Owner Motion for Observations on the Cross-Examination Testimony of Bruce Branchaud, Ph.D. and Michael Metzker, Ph.D., filed Sep. 2, 2014 in connection with IPR2013-00517.
Patent Owner Motion to Exclude Evidence, filed Sep. 2, 2014 in connection with IPR2013-00517;.
Patentee Demonstratives for Oral Hearing, filed Oct. 3, 2014 in connection with IPR2013-00517.
Patentee Opposition to Petitioner Motion to Exclude Evidence, filed Sep. 15, 2014 in connection with IPR2013-00517.
Patentee's Reply to Petitioner's Opposition to Patentee Motion toExclude Evidence, filed Sep. 22, 2014 in connection with IPR2013-00517.
Pelletier H, Sawaya MR, Kumar A, Wilson SH, Kraut J. (1994) "Structures of ternary complexes of rat DNA polymerase β, a DNA template-primer, and ddCTP." Science 264: 1891-1903.

(56) References Cited

OTHER PUBLICATIONS

Pending claims in U.S. Appl. No. 11/922,385, filed Jul. 29, 2009 by Ju et al. (published as 2009/0325154 A1, Dec. 31, 2009).

Pending claims in U.S. Appl. No. 12/084,457, filed Apr. 30, 2008 by Ju et al. (published as 2009/0263791 A1, Oct. 22, 2009).

Pending claims in U.S. Appl. No. 12/734, 229, filed Nov. 3, 2010, by Ju et al. (published as U.S. Patent Application Publication No. 2011/0039259 A1, Feb. 17, 2011).

Pending claims in U.S. Appl. No. 13/186, 353, filed Jul. 19, 2011 by Ju et al (published as 2012/0156680 A1, Jun. 21, 2012).

Petitioner Demonstratives for Oral Hearing, filed Oct. 3, 2014 in connection with IPR2013-00517.

Petitioner Motion to Exclude Evidence, filed Sep. 2, 2014 in connection with IPR2013-00517.

Petitioner Opposition to Patentee Motion to Exclude Evidence, filed Sep. 15, 2014 in connection with IPR2013-00517.

Petitioner Reply to Patent Owner Response, filed Jul. 28, 2014 in connection with IPR2013-00517.

Petitioner's Feb. 28, 2014 Opposition to Patentee Motion to Amend in connection with IPR2013-00266.

Petitioner's Reply to Patentee's Opposition to Motion to Amend, filed Sep. 22, 2014 in connection with IPR2013-00517.

Prober JM, Trainor GL, Dam RJ, Hobbs FW, Robertson CW, Zagursky RJ, Cocuzza AJ, Jensen MA, Baumeister K. (1987) "A system for rapid DNA sequencing with fluorescent chain-terminating dideoxynucleotides," Science 238:336-341.

Quaedflieg et al. (1992) "An Alternative Approach Toward the Synthesis of (3'→5') Methylene Acetal Linked Dinucleosides." Tetrahedron Letters, vol. 33, pp. 3081-3084.

Rao et al. (2001) "Four Color FRET Dye Nucleotide Terminators For DNA Sequencing," Nucleosides, Nucleotides and Nucleic Acids, 20: 673-676.

Rasolonjatovo et al. (1998) "6-N-(N-Methylanthranylamido)-4-Oxo-Hexanoic Acid: A New Fluorescent Protecting Group Applicable to a New DNA Sequencing Method," Nucleosides and Nucleotides, 17:2021-2025.

Restriction Requirement dated Oct. 1, 2007 in connection with U.S. Appl. No. 10/521,206.

Ronaghi M, Uhlen M, Nyren P. (1998) "A sequencing Method based on real-time pyrophosphate." Science 281:364-365.

Ronaghi, (1998) "PCR-Introduced Loop Structure As Primer in DNA Sequencing." BioTechniques, 25:876.

Rosenblum, B.B. et al. (1997) "New dye-labeled terminators for improved DNA sequencing patterns," Nucleic Acids Res. 25: 4500-4504.

Roskey, M.T, Juhasz, P., Smirnov, I.P., Takach, E. J., Martin, S.A., and Haff, L.A. (1996) "DNA sequencing by delayed extraction-matrix-assisted laser desorption/ionization time of flight mass spectrometry." Proc. Natl. Acad. Sci. USA. 93:4724-4729.

Ross, P. et al. (1998) High Level Multiplex Genotyping by MALDI-TOF Mass Spectrometry, Nat. Biotech 16:1347-1351.

Ross, P.L. et al. (1997) "Discrimination of Single-Nucleotide Polymorphisms in Human DNA Using Peptide Nucleic Acid Probes Detected by MALDI-TOF Mass Spectrometry," Anal. Chem. 69:4197-4202.

Ruparel et al., (2005) "Design and Synthesis of a 3'-O-Allyl Photocleavable Fluorescent Nucleotide as a Reversible Terminator for DNA Sequencing by Synthesis," PNAS, 102(17):5932-5937.

Sarfati et al., (1995) "Synthesis of fluorescent derivatives of 3'-O-(6-aminohexanoyl)-pyrimidine nucleosides 5'-triphosphates that act as DNA polymerase substrates reversibly tagged at C-3'," JCS Perkin Trans, 1163-1171.

Saxon, E. and Bertozzi, C.R. (2000) "Cell surface engineering by a modified Staudinger reaction," Science 287:2007-2010.

Schena, M., Shalon, D. and Davis, R. Brown P.O. (1995) "Quantitative monitoring of gene expression patterns with a cDNA microarray," Science 270:467-470.

Seeger (1998) "Single Molecule Fluorescence: High-Performance Molecular Diagnosis and Screening," Bioforum, Git Verlag, Darmstadt, DE vol. 21.

Seo et al. (2003) "Click Chemistry to Construct Fluorescent Oligonucleotides for DNA Sequencing," J. Org. Chem. 68:609.

Seo et al., (2005) "Four-Color DNA Sequencing by Synthesis on a Chip Using Photocleavable Fluorescent Nucleotides," PNAS 102(17):5926-5931.

Seo, T. S., Bai, X., Ruparel, H., Li, Z., Turro, N. J. and Ju, J. "Photocleavable fluorescent nucleotides for DNA sequencing on a chip constructed by site-specific coupling chemistry." Proc. Natl. Acad. Sci. USA 2004, 101, 5488-5493.

Sep. 16, 2012 Motion to Waive Page Limit and Proposed Petition in connection with Petition for Inter Partes Review of U.S. Pat. No. 7,713,698, dated May 11, 2010.

Sep. 16, 2012 Petition for Inter Partes Review of U.S. Pat. No. 7,713,698, dated May 11, 2010.

Sep. 16, 2012 Petition for Inter Partes Review of U.S. Pat. No. 7,790,869.

Sep. 17, 2012 Motion to Waive Page Limit and Proposed Petition in connection with Petition for Inter Partes Review of U.S. Pat. No. 7,790,869.

Sep. 27, 2013 Petitioner Opposition to Motion to Amend in connection with IPR2012-00006.

Sep. 27, 2013 Petitioner Opposition to Motion to Amend in connection with IPR2012-00007.

Sep. 27, 2013 Petitioner Opposition to Motion to Amend in connection with IPR2013-00011.

Sep. 27, 2013 Petitioner Reply to Response to Petition in connection with IPR2012-00006.

Sep. 27, 2013 Petitioner Reply to Response to Petition in connection with IPR2012-00007.

Sep. 27, 2013 Petitioner Reply to Response to Petition in connection with IPR2013-00011.

Sep. 28, 2010 Communication issued in connection with UK Patent Application No. 0909600.9.

Shendure, J.; Porreca, G. J.; Reppas, N. B.; et al. (2005) "Accurate Multiplex Polony Sequencing of an Evolved Bacterial Genome." Science, 309:1728-1732.

Smith, L. M.; Sanders, J. Z.; Kaiser, R. J.; et al. "Fluorescence detection in automated DNA sequence analysis, " Nature (1986), 321:674-679.

Speicher, M.R., Ballard, S. G., and Ward, D. C. (1996) "Karyotyping human chromosomes by combinatorial multi-fluor FISH," Nature Genetics 12: 368-375.

Stoerker, J. et al. (2000) "Rapid Genotyping by MALDI-monitored nuclease selection from probe Libraries," Nat. Biotech 18:1213-1216.

Stratagene Catalog, 1988, p. 39.

Supplementary European Search Report dated Feb. 16, 2004 in connection with European Patent Application No. 01977533.

Supplementary European Search Report dated Feb. 9, 2007 in connection with European Patent Application No. 03764568.6.

Supplementary European Search Report dated Jun. 7, 2005 in connection with European Patent Application No. 01968905.

Supplementary European Search Report dated May 25, 2005 in connection with European Patent Application No. 02728606.1.

Supplementary European Search Report dated May 28, 2004 in connection with European Patent Application No. 01977533.7.

Supplementary European Search Report dated Sep. 9, 2008 in connection with PCT International Application No. PCT/US05/06960.

Tang, K., Fu, D.J., Julien, D., Braun, A., Cantor, C.R., and Koster, H. (1999) "Chip-based genotyping by mass spectrometry," Proc. Natl. Acad. Sci. USA. 96:10016-10020.

Tong, X. and Smith, L.M. (1992) "Solid-Phase Method for the Purification of DNA Sequencing Reactions," Anal. Chem. 64:2672-2677.

Torimura et al. (2001) "Fluorescence-Quenching Phenomenon by Photoinduced Electron Transfer between a Fluorescent Dye and Nucleotide Base," Analytical Sciences, 17:155-160.

Transcript of May 28, 2014 Oral Hearing in IPR2013-00266, entered Jul. 8, 2014.

Tuncel et al. (1999) "Catalytically Self-Threading Polyrotaxanes," Chem. Comm. 1509-1510.

(56) References Cited

OTHER PUBLICATIONS

Veeneman et al. (1991) "An Efficient Approach to the Synthesis of Thymidine Derivatives Containing Phosphate-Isoteric Methylene Acetyl Linkages," Tetrahedron, 47: 1547-1562.

Wada et al. (2001) "2-(Azidomethyl) benzoyl as a new protecting group in nucleosides," Tetrahedron Letters, 42:1069-1072.

Weiss (1999) "Fluorescent Spectroscopy of Single Biomolecules." Science, 283:1676.

Welch et al. (1999) "Synthesis of Nucleosides Designed for Combinatorial DNA Sequencing," Chemistry, European Journal, 5:951-960.

Welch MB, Burgess K, (1999) "Synthesis of fluorescent, photolabile 3'-O-protected nucleoside triphosphates for the base addition sequencing scheme." Nucleosides and Nucleotides 18:197-201.

Wendy, Jen. et al. (2000) "New Strategies for Organic Catalysis: The First Enantioselective Organocatalytic 1,3-Dipolar Cycloaddition," J. Am. Chem. Soc. 122:9874-9875.

Woolley, A. T. et al. (1997) "High-Speed DNA Genotyping Using Microfabricated Capillary Array Electrophoresis Chips," Anal. Chem. 169:2181-2186.

Written Opinion dated Jun. 3, 2009 in connection with International Application No. PCT/US07/24646.

Written Opinion of the International Searching Authority dated Dec. 15, 2006 in connection with PCT/US05/13883.

Written Opinion of the International Searching Authority dated Oct. 27, 2005 in connection with PCT/US05/06960.

Yamashita et al. (1987) "Studies on Antitumor Agents VII. Antitumor Activities of O-Alkoxyalkyl Derivatives of 2'-Deoxy-5-trifluoromethyluridine. " Chem Pharm. Bull., vol. 35, pp. 2373-2381.

Zavgorodny et al. (2000) Nucleosides, Nucleotides and Nucleic Acids, 19(10-12):1977-1991.

Zavgorodny, S. et al. (1991) "1-Alkylthioalkylation of Nucleoside Hydroxyl Functions and Its Synthetic Applications: A New Versatile Method in Nucleoside Chemistry," Tetrahedron Letters, 32(51):7593-7596.

Zhang et al. (2002) "Synthesis of Releasable Electrophore Tags for Applications in Mass Spectrometry," Bioconjugate Chem., vol. 13, pp. 1002-1012.

Zhu, Z.; Chao, J.; Yu, H; et al. "Directly labeled DNA probes using fluorescent nucleotides with different length linkers," Nucleic Acids Res. (1994), 22, pp. 3418-3422.

\* cited by examiner

Extension with 3'-O-allyl-dNTP-allyl-Dye on a repeat G template.

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
gttgatgtac acattgtcaa                                               20

<210> SEQ ID NO 2
<211> LENGTH: 100
<212> TYPE: DNA
<213> ORGANISM: Artificial Sequence
<220> FEATURE:
<223> OTHER INFORMATION: template

<400> SEQUENCE: 2
tacccggagg ccaagtacgg cgggtacgtc cttgacaatg tgtacatcaa catcacctac   60
caccatgtca gtctcggttg gatcctctat tgtgtccggg                        100

<210> SEQ ID NO 3
<211> LENGTH: 48
<212> TYPE: DNA
<213> ORGANISM: Artificial Sequence
<220> FEATURE:
<223> OTHER INFORMATION: template

<400> SEQUENCE: 3
tttttgtttt tttttcgat cgacttaagg cgcttgcgcc ttaagtcg                 48

<210> SEQ ID NO 4
<211> LENGTH: 82
<212> TYPE: DNA
<213> ORGANISM: Artificial Sequence
<220> FEATURE:
<223> OTHER INFORMATION: template

<400> SEQUENCE: 4
agtcagtctc tcatctcgac atctacgcta ctcgtcgatc ggaaacagct atgaccatgc   60
ttgcatggtc atagctgttt cc                                            82

<210> SEQ ID NO 5
<211> LENGTH: 18
<212> TYPE: DNA
<213> ORGANISM: Artificial Sequence
<220> FEATURE:
<223> OTHER INFORMATION: primer

<400> SEQUENCE: 5
agaggatcca accgagac                                                 18

<210> SEQ ID NO 6
<211> LENGTH: 60
<212> TYPE: DNA
<213> ORGANISM: Artificial Sequence
<220> FEATURE:
<223> OTHER INFORMATION: template

<400> SEQUENCE: 6
gtgtacatca acatcaccta ccaccatgtc agtctcggtt ggatcctcta ttgtgtccgg   60

FOUR-COLOR DNA SEQUENCING BY SYNTHESIS USING CLEAVABLE FLUORESCENT NUCLEOTIDE REVERSIBLE TERMINATORS

CROSS-REFERENCE TO RELATED APPLICATIONS

This application is a continuation of U.S. application Ser. No. 16/722,702, filed Dec. 20, 2019, now allowed, a continuation of U.S. application Ser. No. 15/988,321, filed May 24, 2018, now abandoned, a continuation of U.S. application Ser. No. 15/354,531, filed Nov. 17, 2016, now U.S. Pat. No. 10,000,801, issued Jun. 19, 2018, a continuation of U.S. application. Ser. No. 14/242,487, filed Apr. 1, 2014, now U.S. Pat. No. 9,523,151, issued Dec. 27, 2016, a continuation of U.S. application Ser. No. 13/665,588, filed Oct. 31, 2012, now abandoned, a continuation of U.S. application Ser. No. 13/023,283, filed Feb. 8, 2011, now U.S. Pat. No. 8,298,792, issued Oct. 30, 2012, a continuation of U.S. application Ser. No. 12/312,903, filed. Jul. 9, 2009, now U.S. Pat. No. 7,833,869, issued Feb. 8, 2011, a § 371 national stage of PCT International Application. No. PCT/US2007/024646, filed Nov. 30, 2007, claiming the benefit of U.S. Provisional Application No. 60/872,240, filed Dec. 1, 2006, the contents of each of which are hereby incorporated by reference in their entireties into this application.

Throughout this application, various publications are referenced in parentheses by number. Full citations for these references may be found at the end of the specification immediately preceding the claims. The disclosures of these publications in their entireties are hereby incorporated by reference into this application to more fully describe the state of the art to which this invention pertains.

This invention was made with government support under grant number P50-HG002806 awarded by the National Institutes of Health. The government has certain rights in the invention.

BACKGROUND OF THE INVENTION

DNA sequencing is driving genomics research and discovery. The completion of the Human Genome Project has set the stage for screening genetic mutations to identify disease genes on a genome-wide scale (1). Accurate high-throughput DNA sequencing methods are needed to explore the complete human genome sequence for applications in clinical medicine and health care. To overcome the limitations of the current electrophoresis-based sequencing technology (2-5), a variety of new DNA-sequencing methods have been investigated. Such approaches include sequencing by hybridization (6), mass spectrometry based sequencing (7-9), sequence-specific detection of single-stranded DNA using engineered nanopores (10) and sequencing by ligation (11). More recently, DNA sequencing by synthesis (SBS) approaches such as pyrosequencing (12), sequencing of single DNA molecules (13) and polymerase colonies (14) have been widely explored.

The concept of DNA sequencing by synthesis (SBS) was revealed in 1988 with an attempt to sequence DNA by detecting the pyrophosphate group that is generated when a nucleotide is incorporated in a DNA polymerase reaction (15). Pyrosequencing which was developed based on this concept and an enzymatic cascade has been explored for genome sequencing (16). However, there are inherent difficulties in this method for determining the number of incorporated nucleotides in homopolymeric regions of the template. Additionally, each of the four nucleotides needs to be added and detected separately, which increases the overall detection time. The accumulation of un-degraded nucleotides and other components could also lower the accuracy of the method when sequencing a long DNA template. It is thus desirable to have a simple method to directly detect a reporter group attached to the nucleotide that is incorporated into a growing DNA strand in the polymerase reaction rather than relying on a complex enzymatic cascade. The SBS scheme based on fluorescence detection coupled with a chip format has the potential to markedly increase the throughput of DNA sequencing projects. Consequently, several groups have investigated such a system with an aim to construct an ultra high-throughput DNA sequencing method (17-18). Thus far, no complete success of using such a system to unambiguously sequence DNA has been published.

Previous work in the literature exploring the SBS method is mostly focused on designing and synthesizing a cleavable chemical moiety that is linked to a fluorescent dye to cap the 3'-OH group of the nucleotides (19-21). The rationale is that after the fluorophore is removed, the 3'-OH would be regenerated to allow subsequent nucleotide addition. However, no success has been reported for the incorporation of such a nucleotide with a cleavable fluorescent dye on the 3' position by DNA polymerase into a growing DNA strand. The reason is that the 3' position on the deoxyribose is very close to the amino acid residues in the active site of the polymerase, and the polymerase is therefore sensitive to modification in this area of the ribose ring, especially with a large fluorophore (22).

SUMMARY OF THE INVENTION

This invention provides a method for determining the sequence of a DNA comprising performing the following steps for each residue of the DNA to be sequenced:
(a) contacting the DNA with a DNA polymerase in the presence of (i) a primer and (ii) four nucleotide analogues under conditions permitting the DNA polymerase to catalyze DNA synthesis, wherein (1) the nucleotide analogues consist of an analogue of dGTP, an analogue of dCTP, an analogue of dTTP or dUTP, and an analogue of dATP, (2) each nucleotide analogue comprises (i) a base selected from the group consisting of adenine, guanine, cytosine, thymine or uracil, and analogues thereof, (ii) a deoxyribose, (iii) a moiety cleavably linked to the 3'-oxygen of the deoxyribose and (iv) a unique label cleavably linked to the base, so that a nucleotide analogue complementary to the residue being sequenced is incorporated into the DNA by the DNA polymerase, and (3) each of the four analogues has a unique label which is different than the unique labels of the other three analogues;
(b) removing unbound nucleotide analogues;
(c) again contacting the DNA with a DNA polymerase in the presence of (i) a primer and (ii) four reversible terminators under conditions permitting the DNA polymerase to catalyze DNA synthesis, wherein (1) the reversible terminators consist of an analogue of dGTP, an analogue of dCTP, an analogue of dTTP or dUTP, and an analogue of dATP, (2) each nucleotide analogue comprises (i) a base selected from the group consisting of adenine, guanine, cytosine, thymine or uracil, and analogues thereof, which base does not have a unique label bound thereto, (ii) a deoxyribose, and (iii) a moiety cleavably linked to the 3'-oxygen of the deoxyribose;

(d) removing unbound reversible terminators;
(e) determining the identity of the nucleotide analogue incorporated in step (a) via determining the identity of the corresponding unique label, with the proviso that step (e) can either precede step (c) or follow step (d); and
(f) following step (e), except with respect to the final DNA residue to be sequenced, cleaving from the incorporated nucleotide analogues the unique label, if applicable, and the moiety linked to the 3'-oxygen atom of the deoxyribose, thereby determining the sequence of the DNA.

This invention also provides a kit for performing the method of claim 1, comprising, in separate compartments,
(a) nucleotide analogues of (i) GTP, (ii) ATP, (iii) CTP and (iv) TTP or UTP, wherein each analogue comprises (i) a base selected from the group consisting of adenine, guanine, cytosine, thymine or uracil, or an analogue thereof, (ii) a deoxyribose, (iii) a cleavable moiety bound to the 3'-oxygen of the deoxyribose and (iv) a unique label bound to the base via a cleavable linker,
(b) reversible terminators comprising a nucleotide analogue of (i) GTP, (ii) ATP, (iii) CTP and (iv) TTP or UTP, wherein each analogue comprises (i) a base selected from the group consisting of adenine, guanine, cytosine, thymine or uracil, or an analogue thereof, which base does not have a unique label bound thereto, (ii) a deoxyribose, and (iii) a cleavable moiety bound to the 3'-oxygen of the deoxyribose;
(c) reagents suitable for use in DNA polymerization; and
(d) instructions for use.

DETAILED DESCRIPTION OF THE INVENTION

Terms

Figure 1:
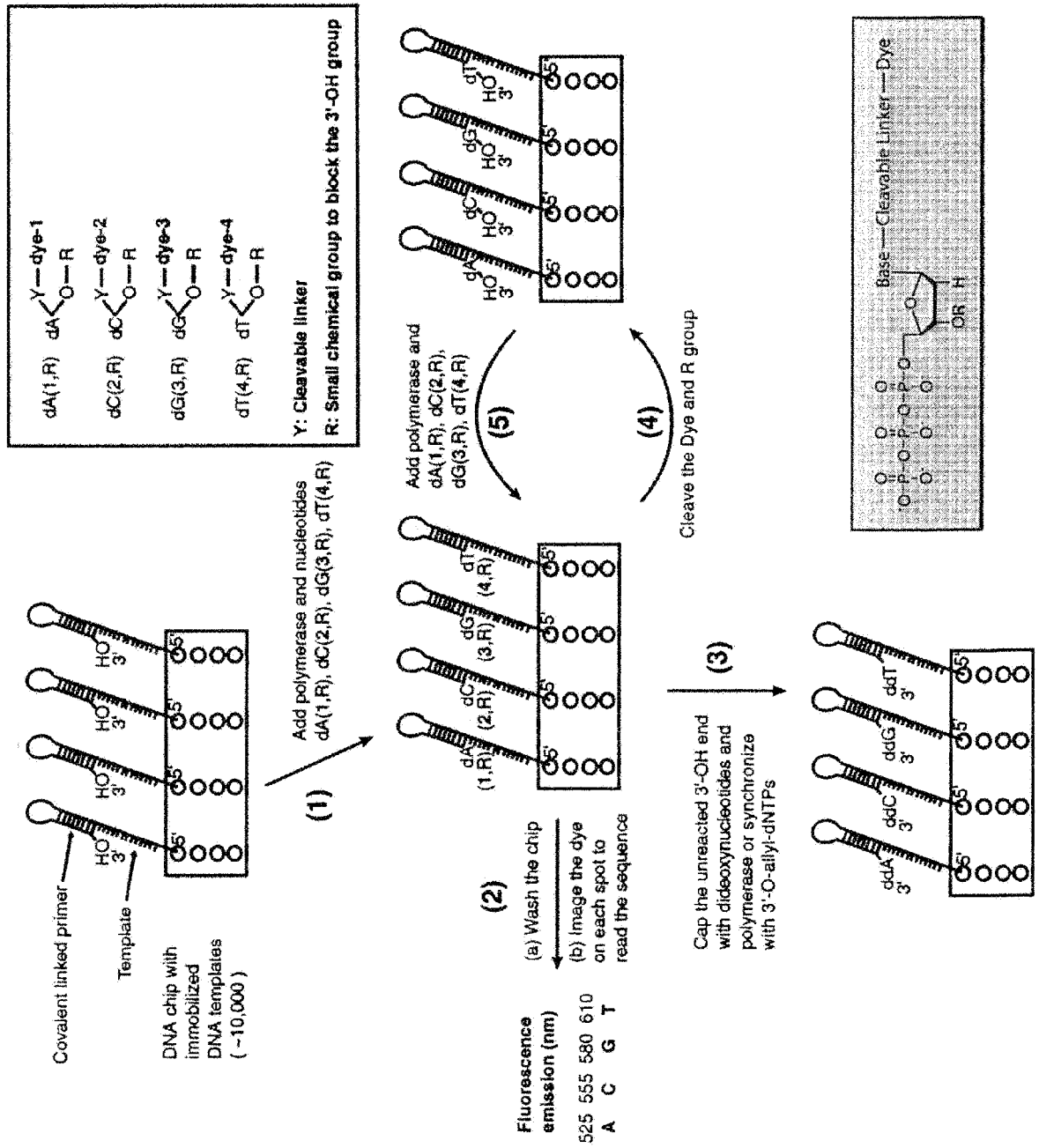
FIG. 1. A chip is constructed with immobilized DNA templates that are able to self-prime for initiating the polymerase reaction. Four nucleotide analogues are designed such that each is labeled with a unique fluorescent dye on the specific location of the base through a cleavable linker, and a small chemically reversible moiety (R) to cap the 3'-OH group. Upon adding the four nucleotide analogues and DNA polymerase, only the nucleotide analogue complementary to the next nucleotide on the template is incorporated by polymerase on each spot of the chip (step 1). A 4 color fluorescence imager is used to image the surface of the chip, and the unique fluorescence emission from the specific dye on the nucleotide analogues on each spot of the chip will yield the identity of the nucleotide (step 2). After imaging, the small amount of unreacted 3'-OH group on the self-primed template moiety is capped by excess ddNTPs and DNA polymerase to avoid interference with the next round of synthesis or by 3'-O-allyl-dNTPs to synchronize the incorporation (step 3). The dye moiety and the R protecting group will be removed to generate a free 3'-OH group with high yield (step 4). The self-primed DNA moiety on the chip at this stage is ready for the next cycle of the reaction to identify the next nucleotide sequence of the template DNA (step 5).

As used herein, and unless stated otherwise, each of the following terms shall have the definition set forth below.

A—Adenine;
C—Cytosine;
DNA—Deoxyribonucleic acid;
G—Guanine;
RNA—Ribonucleic acid;
T—Thymine; and
U—Uracil.

"Nucleic acid" shall mean any nucleic acid molecule, including, without limitation, DNA, RNA and hybrids thereof. The nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996-1997, Roche Molecular Systems, Inc., Branchburg, New Jersey, USA).

"Type" of nucleotide refers to A, G, C, T or U.

"Mass tag" shall mean a molecular entity of a predetermined size which is capable of being attached by a cleavable bond to another entity.

"Solid substrate" shall mean any suitable medium present in the solid phase to which an antibody or an agent may be affixed.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Embodiments of the Invention

This invention provides a method for determining the sequence of a DNA comprising performing the following steps for each residue of the DNA to be sequenced:
(a) contacting the DNA with a DNA polymerase in the presence of (i) a primer and (ii) four nucleotide analogues under conditions permitting the DNA polymerase to catalyze DNA synthesis, wherein (1) the nucleotide analogues consist of an analogue of dGTP, an analogue of dCTP, an analogue of dTTP or dUTP, and an analogue of dATP, (2) each nucleotide analogue comprises (i) a base selected from the group consisting of adenine, guanine, cytosine, thymine or uracil, and analogues thereof, (ii) a deoxyribose, (iii) a moiety cleavably linked to the 3'-oxygen of the deoxyribose and (iv) a unique label cleavably linked to the base, so that a nucleotide analogue complementary to the residue being sequenced is incorporated into the DNA by the DNA polymerase, and (3) each of the four analogues has a unique label which is different than the unique labels of the other three analogues;
(b) removing unbound nucleotide analogues;
(c) again contacting the DNA with a DNA polymerase in the presence of (i) a primer and (ii) four reversible terminators under conditions permitting the DNA polymerase to catalyze DNA synthesis, wherein (1) the reversible terminators consist of an analogue of dGTP, an analogue of dCTP, an analogue of dTTP or dUTP, and an analogue of dATP, (2) each nucleotide analogue comprises (i) a base selected from the group consisting of adenine, guanine, cytosine, thymine or uracil, and analogues thereof, which base does not have a unique label bound thereto, (ii) a deoxyribose, and (iii) a moiety cleavably linked to the 3'-oxygen of the deoxyribose;
(d) removing unbound reversible terminators;
(e) determining the identity of the nucleotide analogue incorporated in step (a) via determining the identity of the corresponding unique label, with the proviso that step (e) can either precede step (c) or follow step (d); and
(f) following step (e), except with respect to the final DNA residue to be sequenced, cleaving from the incorporated nucleotide analogues the unique label, if applicable, and the moiety linked to the 3'-oxygen atom of the deoxyribose,
thereby determining the sequence of the DNA.

This invention also provides the instant method, wherein step (e) is performed before step (c).

This invention also provides the instant method, wherein the moiety cleavably linked to the 3'-oxygen of the deoxyribose is chemically cleavable or photocleavable. This invention also provides the instant method, wherein the moiety cleavably linked to the 3'-oxygen of the deoxyribose in the nucleotide analogs of step (a) is an allyl moiety or a 2-nitrobenzyl moiety.

This invention also provides the instant method, wherein the moiety cleavably linked to the 3'-oxygen of the deoxyribose in the reversible terminators of step (c) is an allyl moiety or a 2-nitrobenzyl moiety.

This invention also provides the instant method, wherein the unique label is bound to the base via a chemically cleavable or photocleavable linker.

This invention also provides the instant method, wherein the unique label bound to the base via a cleavable linker is a dye, a fluorophore, a chromophore, a combinatorial fluorescence energy transfer tag, a mass tag, or an electrophore.

This invention also provides the instant method, wherein the moiety is chemically cleavable with $Na_2PdCl_4$/P$(PhSO_3Na)_3$. This invention also provides the instant method, wherein the linker is chemically cleavable with $Na_2PdCl_4$/P$(PhSO_3Na)_3$.

This invention also provides the instant method, wherein the primer is a self-priming moiety.

This invention also provides the instant method, wherein the DNA is bound to a solid substrate. This invention also provides the instant method, wherein the DNA is bound to the solid substrate via 1,3-dipolar azide-alkyne cycloaddition chemistry. This invention also provides the instant method, wherein the DNA is bound to the solid substrate via a polyethylene glycol molecule. This invention also provides the instant method, wherein the DNA is alkyne-labeled. This invention also provides the instant method, wherein the DNA is bound to the solid substrate via a polyethylene glycol molecule and the solid substrate is azide-functionalized. This invention also provides the instant method, wherein the DNA is immobilized on the solid substrate via an azido linkage, an alkynyl linkage, or biotin-streptavidin interaction.

This invention also provides the instant method, wherein the solid substrate is in the form of a chip, a bead, a well, a capillary tube, a slide, a wafer, a filter, a fiber, a porous media, or a column. This invention also provides the instant method, wherein the solid substrate is gold, quartz, silica, plastic, glass, diamond, silver, metal, or polypropylene. This invention also provides the instant method, wherein the solid substrate is porous.

This invention also provides the instant method, wherein about 1000 or fewer copies of the DNA are bound to the solid substrate. This invention also provides the instant invention wherein $1 \times 10^7$, $1 \times 10'$ or $1 \times 10^4$ or fewer copies of the DNA are bound to the solid substrate.

This invention also provides the instant method, wherein the four nucleotide analogues in step (a) are 3'-O-allyl-dGTP-allyl-Cy5, 3'-O-allyl-dCTP-allyl-Bodipy-FL-510, 3'-O-allyl-dATP-allyl-ROX and 3'-O-allyl-dUTP-allyl-R6G. This invention also provides the instant method, wherein the four nucleotide analogues in step (a) are 3'-O-allyl-dGTP-allyl-Bodipy-FL-510, 3'-O-allyl-dCTP-allyl-Bodipy-650, 3'-O-allyl-dATP-allyl-ROX and 3'-O-allyl-dUTP-allyl-R6G. This invention also provides the instant method, wherein the four nucleotide analogues in step (a) are 3'-O-allyl-dGTP-allyl-Bodipy-650, 3'-O-allyl-dCTP-allyl-Bodipy-FL-510, 3'-O-allyl-dATP-allyl-ROX and 3'-O-allyl-dUTP-allyl-R6G.

It is understood that in other embodiments the nucleotide analogues are photocleavable. For example, 2-nitrobenzyl can replace any of the allyl moieties in the analogues described herein. For example, 3'-O-2-nitrobenzyl-dGTP-allyl-Bodipy-650, 3'-O-2-nitrobenzyl-dGTP-2-nitrobenzyl-Bodipy-650, 3'-O-allly-dGTP-2-nitrobenzyl-Bodipy-650. One of skill in the art would recognize various other chemically cleavable or photochemically cleavable moieties or linkers that can be used in place of the examples described herein. Additionally, the unique labels may also be varied, and the examples set forth herein are non-limiting. In an embodiment UV light is used to photochemically cleave the photochemically cleavable linkers and moieties.

This invention also provides the instant method, wherein the reversible terminators in step (c) are 3'-O-allyl-dGTP, 3'-O-allyl-dCTP, 3'-O-allyl-dATP and 3'-O-allyl-dUTP. This invention also provides the instant method, wherein the reversible terminators in step (c) are 3'-O-2-nitrobenzyl-dGTP, 3'-O-2-nitrobenzyl-dCTP, 3'-O-2-nitrobenzyl-dATP and 3'-O-2-nitrobenzyl-dUTP. In an embodiment the reversible terminator is incorporated into the growing strand of DNA.

This invention also provides the instant method, wherein the DNA polymerase is a 9°N polymerase or a variant thereof. DNA polymerases which can be used in the instant invention include, for example E. Coli DNA polymerase I, Bacteriophage T4 DNA polymerase, Sequenase™, Taq DNA polymerase and 9° N polymerase (exo-) A485L/Y409V.RNA polymerases which can be used in the instant invention include, for example, Bacteriophage SP6, T7 and T3 RNA polymerases.

This invention also provides the instant method, wherein the DNA is bound to the solid substrate via a polyethylene glycol molecule and the solid substrate is azide-functionalized or the DNA is immobilized on the solid substrate via an azido linkage, an alkynyl linkage, or biotin-streptavidin interaction; wherein (i) the four nucleotide analogues in step (a) are 3'-O-allyl-dGTP-allyl-Cy5, 3'-O-allyl-dCTP-allyl-Bodipy-FL-510, 3'-O-allyl-dATP-allyl-ROX and 3'-O-allyl-dUTP-allyl-R6G, (ii) the four nucleotide analogues in step (a) are 3'-O-allyl-dGTP-allyl-Bodipy-FL-510, 3'-O-allyl-dCTP-allyl-Bodipy-650, 3'-O-allyl-dATP-allyl-ROX and 3'-O-allyl-dUTP-allyl-R6G, or (iii) the four nucleotide analogues in step (a) are 3'-O-allyl-dGTP-allyl-Bodipy-650, 3'-O-allyl-dCTP-allyl-Bodipy-FL-510, 3'-O-allyl-dATP-allyl-ROX and 3'-O-allyl-dUTP-allyl-R6G; and wherein the reversible terminators in step (c) are 3'-O-allyl-dGTP, 3'-O-allyl-dCTP, 3'-O-allyl-dATP and 3'-O-allyl-dUTP.

This invention also provides a kit for performing the instant method comprising, in separate compartments, (a) nucleotide analogues of (1) GTP, (ii) ATP, (iii) CTP and (iv) TTP or UTP, wherein each analogue comprises (1) a base selected from the group consisting of adenine, guanine, cytosine, thymine or uracil, or an analogue thereof, (ii) a deoxyribose, (iii) a cleavable moiety bound to the 3'-oxygen of the deoxyribose and (iv) a unique label bound to the base via a cleavable linker, (b) reversible terminators comprising a nucleotide analogue of (i) GTP, (ii) ATP, (iii) CTP and (iv) TTP or UTP, wherein each analogue comprises (i) a base selected from the group consisting of adenine, guanine, cytosine, thymine or uracil, or an analogue thereof, which base does not have a unique label bound thereto, (ii) a deoxyribose, and (iii) a cleavable moiety bound to the 3'-oxygen of the deoxyribose;

(c) reagents suitable for use in DNA polymerization; and (d) instructions for use.

This invention further provides the instant kit, wherein the nucleotide analogues of part (a) are 3'-O-allyl-dGTP-allyl-Cy5, 3'-O-allyl-dCTP-allyl-Bodipy-FL-510, 3'-O-allyl-dATP-allyl-ROX and 3'-O-allyl-dUTP-allyl-R6G. This invention further provides the instant kit, wherein the nucleotide analogues of part (a) are 3'-O-allyl-dGTP-allyl-Bodipy-FL-510, 3'-O-allyl-dCTP-allyl-Bodipy-650, 3'-O-allyl-dATP-allyl-ROX and 3'-O-allyl-dUTP-allyl-R6G. This invention further provides the instant kit, wherein the nucleotide analogues of part (a) are 3'-O-allyl-dGTP-allyl-Bodipy-650, 3'-O-allyl-dCTP-allyl-Bodipy-FL-510, 3'-O-allyl-dATP-allyl-ROX and 3'-O-allyl-dUTP-allyl-R6G. This invention further provides the instant kit, wherein the nucleotide analogues of part (b) are 3'-O-allyl-dGTP, 3'-O-allyl-dCTP, 3'-O-allyl-dATP and 3'-O-allyl-dUTP. This invention further provides the instant kit, the reversible terminators in step (c) are 3'-O-2-nitrobenzyl-dGTP, 3'-O-2-nitrobenzyl-dCTP, 3'-O-2-nitrobenzyl-dATP and 3'-O-2-nitrobenzyl-dUTP.

The methods and kits of this invention may be applied, mutatis mutandis, to the sequencing of RNA, or to determining the identity of a ribonucleotide.

Methods for production of cleavably capped and/or cleavably linked nucleotide analogues are disclosed in U.S. Pat. No. 6,664,079, which is hereby incorporated by reference. Combinatorial fluorescence energy tags and methods for production thereof are disclosed in U.S. Pat. No. 6,627,748, which is hereby incorporated by reference.

In an embodiment, the DNA or nucleic acid is attached/bound to the solid surface by covalent site-specific coupling chemistry compatible with DNA.

This invention will be better understood by reference to the Experimental Details which follow, but those skilled in the art will readily appreciate that the specific experiments detailed are only illustrative of the invention as described more fully in the claims which follow thereafter.

Experimental Details

DNA sequencing by synthesis (SBS) on a solid surface during polymerase reaction offers a new paradigm to decipher DNA sequences. Disclosed here is the construction of such a novel DNA sequencing system using molecular engineering approaches. In this approach, four nucleotides (A, C, G, T) are modified as reversible terminators by attaching a cleavable fluorophore to the base and capping the 3'-OH group with a small chemically reversible moiety so that they are still recognized by DNA polymerase as substrates. It is found that an allyl moiety can be used successfully as a linker to tether a fluorophore to 3'-O-allyl-modified nucleotides, forming chemically cleavable fluorescent nucleotide reversible terminators, 3'-O-allyl-dNTPs-allyl-fluorophore, for application in SBS. The fluorophore and the 3'-O-allyl group on a DNA extension product, which is generated by incorporating 3'-O-allyl-dNTPs-allyl-fluorophore in a polymerase reaction, are removed simultaneously in 30 seconds by Pd-catalyzed deallylation in aqueous buffer solution. This one-step dual-deallylation reaction thus allows the re-initiation of the polymerase reaction and increases the SBS efficiency. DNA templates consisting of homopolymer regions were accurately sequenced by using this new class of fluorescent nucleotide analogues on a DNA chip and a 4-color fluorescent scanner.

It is known that some modified DNA polymerases are highly tolerable for nucleotides with extensive modifications with bulky groups such as energy transfer dyes at the 5-position of the pyrimidines (T and C) and 7-position of purines (G and A) (23, 24). The ternary complexes of a rat DNA polymerase, a DNA template-primer, and dideoxycytidine triphosphate have been determined (22) which supports this fact. It was hypothesizrf that if a unique fluorescent dye is linked to the 5-position of the pyrimidines (T and C) and the 7-position of purines (G and A) via a cleavable linker, and a small chemical moiety is used to cap the 3'-OH group, then the resulting nucleotide analogues may be able to incorporate into the growing DNA strand as terminators. Based on this rationale, SBS approach was conceived using cleavable fluorescent nucleotide analogues as reversible terminators to sequence surface-immobilized DNA in 2000 (FIG. 1) (25). In this approach, the nucleotides are modified at two specific locations so that they are still recognized by DNA polymerase as substrates: (i) a different fluorophore with a distinct fluorescent emission is linked to each of the 4 bases through a cleavable linker and (ii) the 3'-OH group is capped by a small chemically reversible moiety. DNA polymerase incorporates only a single nucleotide analogue complementary to the base on a DNA template covalently linked to a surface. After incorporation, the unique fluorescence emission is detected to identify the incorporated nucleotide and the fluorophore is subsequently removed. The 3'-OH group is then chemically regenerated, which allows the next cycle of the polymerase reaction to proceed. Since the large surface on a DNA chip can have a high density of different DNA templates spotted, each cycle can identify many bases in parallel, allowing the simultaneous sequencing of a large number of DNA molecules. The feasibility of performing SBS on a chip using 4 photocleavable fluorescent nucleotide analogues was previously established (26) and it was discovered that an allyl group can be used as a cleavable linker to bridge a fluorophore to a nucleotide (27). The design and synthesis of two photocleavable fluorescent nucleotides as reversible terminators for polymerase reaction has already been reported (28, 29).

Previous research efforts in the present laboratory have firmly established the molecular level strategy to rationally modify the nucleotides by attaching a cleavable fluorescent dye to the base and capping the 3'-OH with a small chemically reversible moiety for SBS. This approach was recently adopted by Genomics Industry to potentially provide a new platform for DNA sequencing (30). Here the design and synthesis of 4 chemically cleavable fluorescent nucleotide analogues as reversible terminators for SBS is disclosed. Each of the nucleotide analogues contains a 3'-O-allyl group and a unique fluorophore with a distinct fluorescence emission at the base through a cleavable allyl linker.

It was first established that these nucleotide analogues are good substrates for DNA polymerase in a solution-phase DNA extension reaction and that the fluorophore and the 3'-O-allyl group can be removed with high efficiency in aqueous solution. Then SBS was performed using these 4 chemically cleavable fluorescent nucleotide analogues as reversible terminators to identify ~20 continuous bases of a DNA template immobilized on a chip. Accurate DNA sequences were obtained for DNA templates containing homopolymer sequences. The DNA template was immobilized on the surface of the chip that contains a PEG linker with 1,3-dipolar azide-alkyne cycloaddition chemistry. These results indicated that successful cleavable fluorescent nucleotide reversible terminators for 4-color DNA sequencing by synthesis can be designed by attaching a cleavable fluorophore to the base and capping the 3'-OH with a small chemically reversible moiety so that they are still recognized by DNA polymerase as substrates. Further optimization of the approach will lead to even longer sequencing readlengths.

Figure 2:
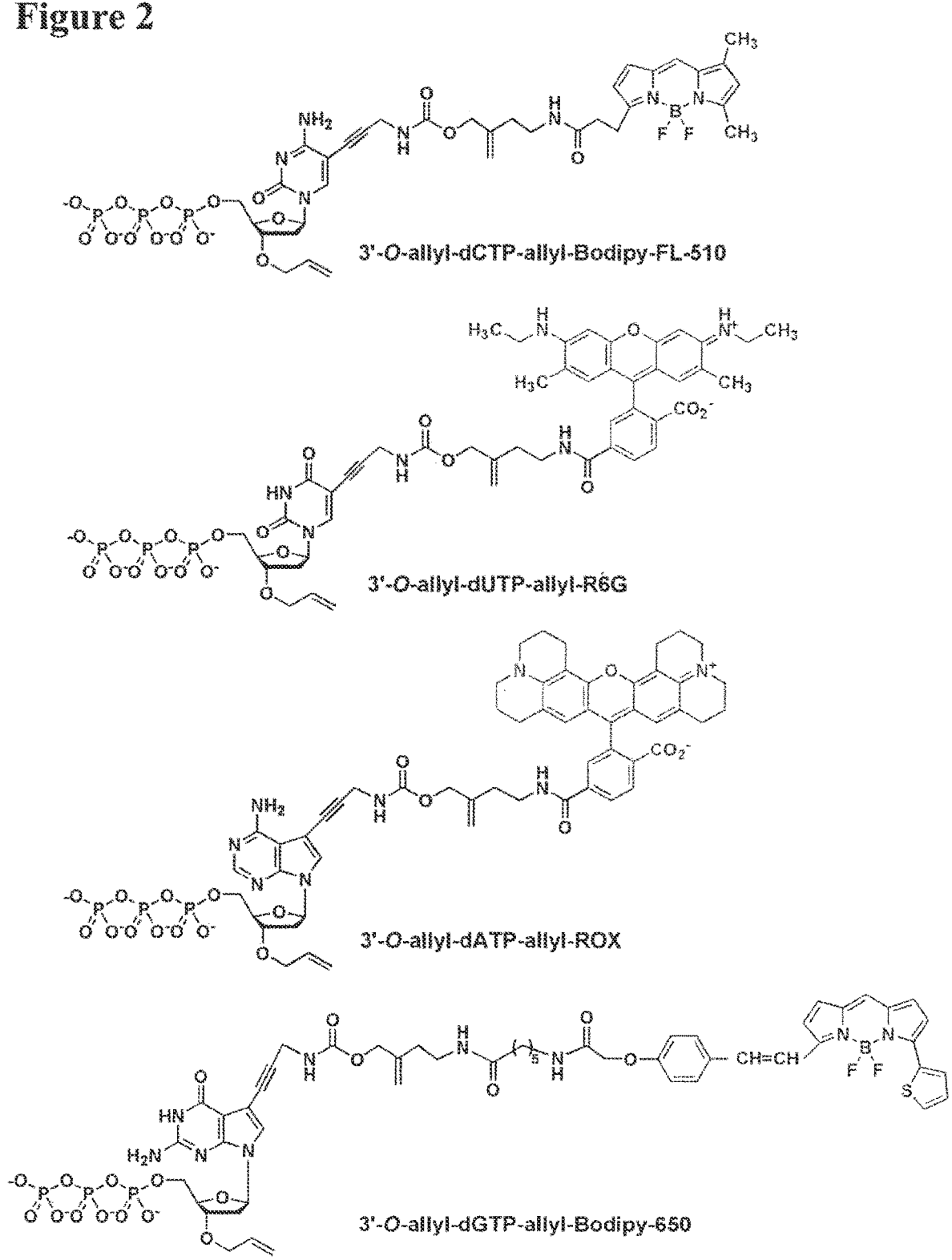
FIG. 2. Structures of 3'-O-allyl-dCTP-allyl-Bodipy-FL-510 ($\lambda_{abs\ (max)}$=502 nm; $\lambda_{em\ (max)}$=510 nm), 3'-O-allyl-dUTP-allyl-R6G ($\lambda_{abs\ (max)}$=525 nm; $\lambda_{em\ (max)}$=550 nm), 3'-O-allyl-dATP-allyl-ROX ($\lambda_{abs\ (max)}$=585 nm; $\lambda_{em\ (max)}$=602 nm), and 3'-O-allyl-dGTP-allyl-Bodipy-650 ($\lambda_{abs\ (max)}$=630 nm; $\lambda_{em\ (max)}$=650 nm).
Figure 3:
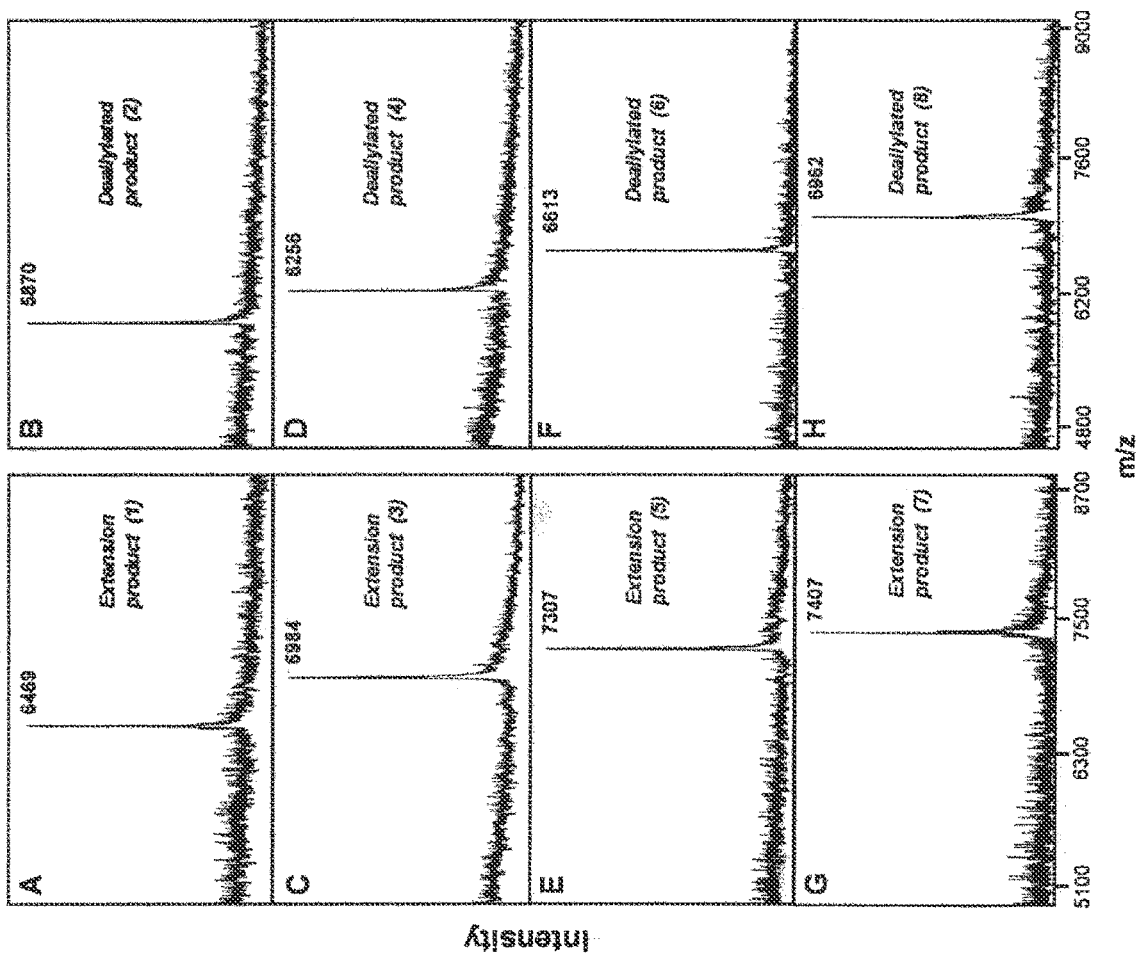
FIG. 3. The polymerase extension scheme (left) and MALDI-TOF MS spectra of the four consecutive extension products and their deallylated products (right). Primer extended with 3'-O-allyl-dUTP-allyl-R6G (1), and its deallylated product 2; Product 2 extended with 3'-O-allyl-dGTP-allyl-Bodipy-650 (3), and its deallylated product 4; Product 4 extended with 3'-O-allyl-dATP-allyl-ROX (5), and its deallylated product 6; Product 6 extended with 3'-O-allyl-dCTP-allyl-Bodipy-FL-510 (7), and its deallylated product 8. After 30 seconds of incubation with the palladium/TPPTS cocktail at 70° C., deallylation is complete with both the fluorophores and the 3'-O-allyl groups cleaved from the extended DNA products.
Figure 4:
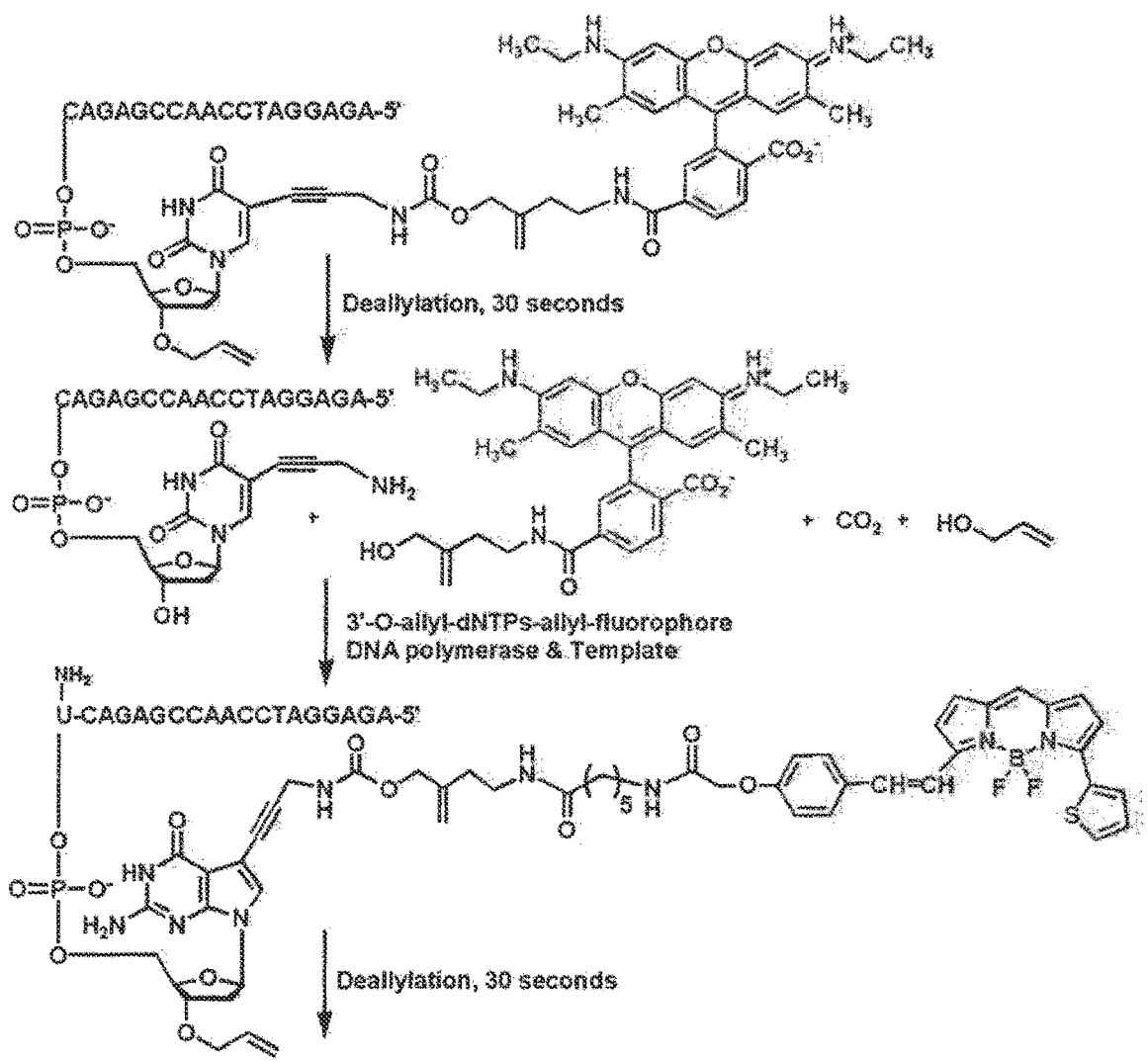
FIG. 4. DNA extension reaction performed in solution phase to characterize the four different chemically cleavable fluorescent nucleotide analogues (3'-O-allyl-dUTP-allyl-R6G, 3'-O-allyl-dGTP-allyl-Bodipy-650, 3'-O-allyl-dATP-allyl-ROX and 3'-O-allyl-dCTP-allyl-Bodipy-FL-510). After each extension reaction, the DNA extension product is purified by HPLC for MALDI-TOF MS measurement to verify that it is the correct extension product. Pd-catalyzed deallylation reaction is performed to produce a DNA product that is used as a primer for the next DNA extension reaction.
Figure 4:
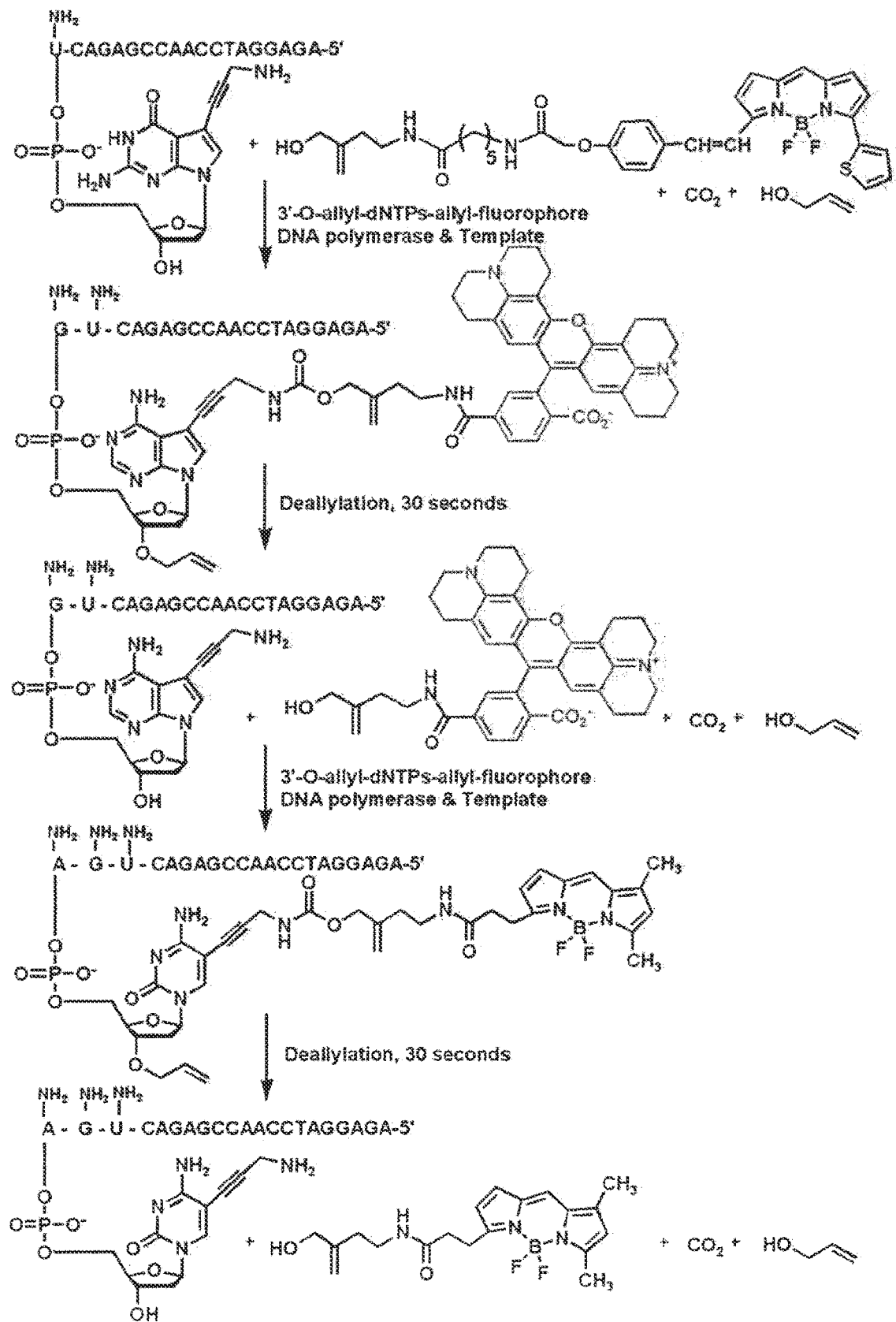

Design and Synthesis of Chemically Cleavable Fluorescent Nucleotide Analogues as Reversible Terminators for SBS To demonstrate the feasibility of carrying out de novo DNA sequencing by synthesis on a chip, four chemically cleavable fluorescent nucleotide analogues (3'-O-allyl-dCTP-allyl-Bodipy-FL-510, 3'-O-allyl-dUTP-allyl-R6G, 3'-O-allyl-dATP-allyl-ROX and 3'-O-allyl-dGTP-allyl-Bodipy-650/Cy5) (FIG. 2) were designed and synthesized as reversible terminators for DNA polymerase reaction. Modified DNA polymerases have been shown to be highly tolerant to nucleotide modifications with bulky groups at the 5-position of pyrimidines (C and U) and the 7-position of purines (A and G). Thus, each unique fluorophore was attached to the 5 position of C/U and the 7 position of A/G through an allyl carbamate linker. However, due to the close proximity of the 3' position on the sugar ring of a nucleotide to the amino acid residues of the active site of the DNA polymerase, a relatively small allyl moiety was chosen as the 3'-OH reversible capping group. It was found that the fluorophore and the 3'-O-allyl group on a DNA extension product, which is generated by incorporation of the chemically cleavable fluorescent nucleotide analogues, are removed simultaneously in 30 seconds by Pd-catalyzed deallylation in aqueous solution. This one-step dual-deallylation reaction thus allows the re-initiation of the polymerase reaction. The detailed synthesis procedure and characterization of the 4 novel nucleotide analogues in FIG. 2 are described in Materials and Methods In order to verify that these fluorescent nucleotide analogues are incorporated accurately in a base-specific manner in a polymerase reaction, four continuous steps of DNA extension and deallylation were carried out in solution. This allows the isolation of the DNA product at each step for detailed molecular structure characterization by MALDI-TOF mass spectrometry (MS) as shown in FIG. 3. The first extension product 5'-U(allyl-R6G)-3'-O-allyl (1) was purified by HPLC and analyzed using MALDI-TOF MS [FIG. 3(A)]. This product was then deallylated using a Pd-catalyzed deallylation cocktail [1× Thermopol I reaction buffer/$Na_2PdCl_4$/$P(PhSO_3Na)_3$]. The active Pd catalyst is generated from $Na_2PdCl_4$ and a ligand $P(PhSO_3Na)_3$ (TPPTS) to mediate the deallylation reaction in DNA compatible aqueous condition to simultaneously cleave both the fluorophore and the 3'-O-allyl group (28). The deallylated product (2) was also analyzed using MALDI-TOF MS [FIG. 3(B)]. As can be seen from FIG. 3(A), the MALDI-TOF MS spectrum consists of a distinct peak at m/z 6469 corresponding to the DNA extension product 5'-U(allyl-R6G)-3'-O-allyl (1), which confirms that the nucleotide analogue can be incorporated base specifically among pool of all four (A, C, G, T) by DNA polymerase into a growing DNA strand. FIG. 3(B) shows the deallylation result of the above DNA product. The peak at m/z 6469 has completely disappeared while the peak corresponding to the dual deallylated product 5'-U (2) appears as the sole dominant peak at m/z 5870, which establishes that the Pd-catalyzed deallylation reaction completely cleaves both the fluorophore and the 3'-O-allyl group with high efficiency without damaging the DNA. The next extension reaction was carried out using this deallylated DNA product with a free 3'-OH group regenerated as a primer along with four allyl modified fluorescent nucleotide mixture to yield an extension product 5'-UG(allyl-Bodipy-650)-3'-O-allyl (3). As described above, the extension product 3 was analyzed by MALDI-TOF MS producing a dominant peak at m/z 6984 [FIG. 3(C)], and then deallylated for further MS analysis yielding a single peak at m/z 6256 (product 4) [FIG. 3(D)]. The third extension reaction yielding 5'-UGA(allyl-ROX)-3'-O-allyl (5), the fourth extension reaction yielding 5'-UGAC(allyl-Bodipy-FL-510)-3'-O-allyl (7) and their deallylation reactions to yield products 6 and 8 were similarly carried out and analyzed by MALDI-TOF MS as shown in FIGS. 3(E), 3(F), 3(G) and 3(H). The chemical structures of the extension and cleavage products for each step are shown in FIG. 4. These results demonstrate that the above-synthesized 4 chemically cleavable fluorescent nucleotide analogues are successfully incorporated with high fidelity into the growing DNA strand in a polymerase reaction, and furthermore, both the fluorophore and the 3'-O-allyl group are efficiently removed by using a Pd-catalyzed deallylation reaction, which makes it feasible to use them for SBS on a chip.

Figure 5:
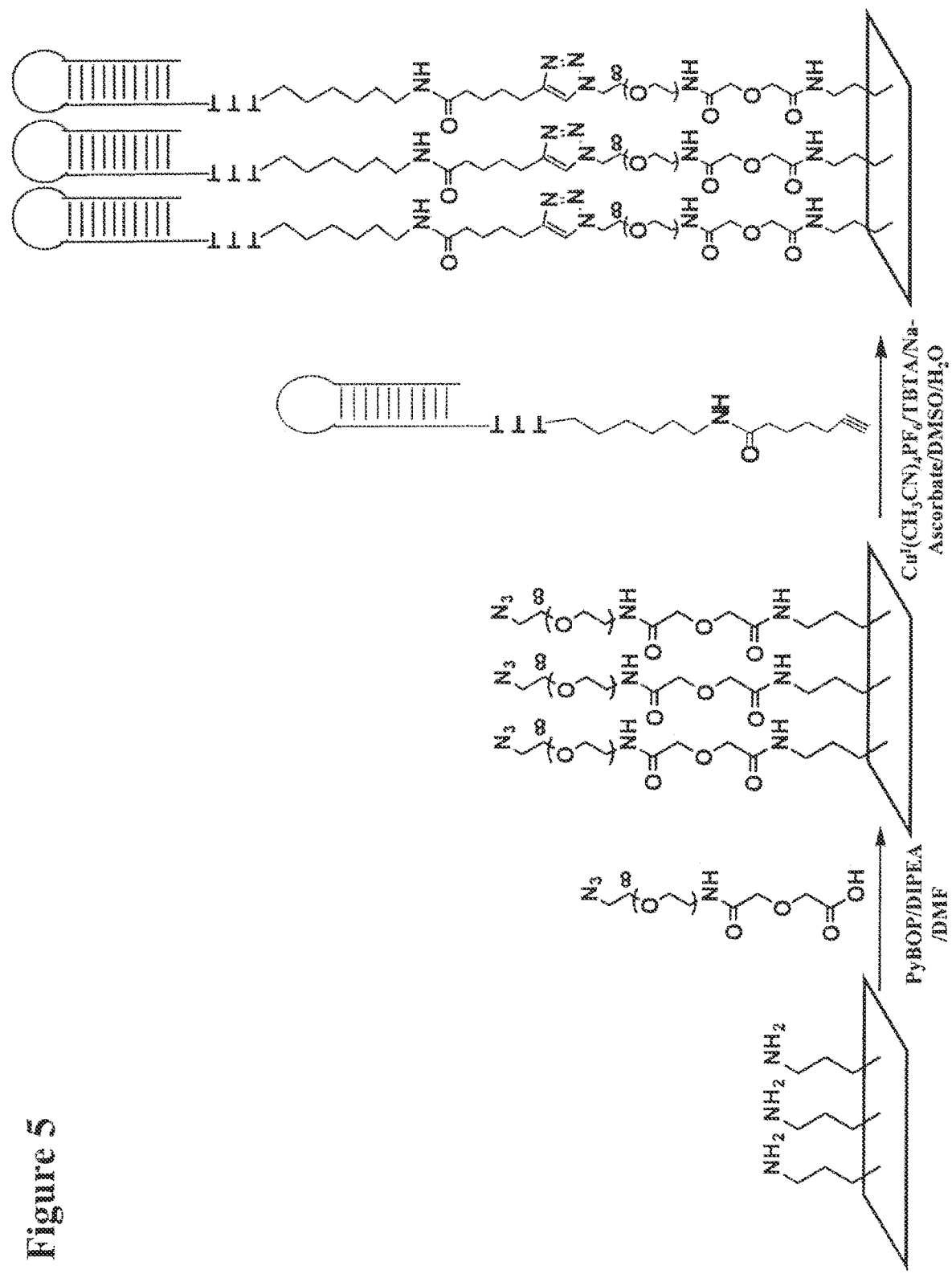
FIG. 5. Preparation of azide-functionalized glass chip through a PEG linker for the immobilization of alkyne labeled self-priming DNA template for SBS.

4-Color DNA Sequencing with Chemically Cleavable Fluorescent Nucleotide Analogues as Reversible Terminators on a DNA Chip The chemically cleavable fluorescent nucleotide analogues were then used in an SBS reaction to identify the sequence of the DNA template immobilized on a solid surface. A site-specific 1,3-dipolar cycloaddition coupling chemistry was used to covalently immobilize the alkyne-labeled self-priming DNA template on the azido-functionalized surface in the presence of a Cu(I) catalyst. The principal advantage offered by the use of a self-priming moiety as compared to using separate primers and templates is that the covalent linkage of the primer to the template in the self-priming moiety prevents any possible dissociation of the primer from the template during the process of SBS. To prevent non-specific absorption of the unincorporated fluorescent nucleotides on the surface of the chip, a PEG linker is introduced between the DNA templates and the chip surface (FIG. 5). This approach was shown to produce very low background fluorescence after cleavage to remove the fluorophore as demonstrated by the DNA sequencing data described below.

Figure 6:
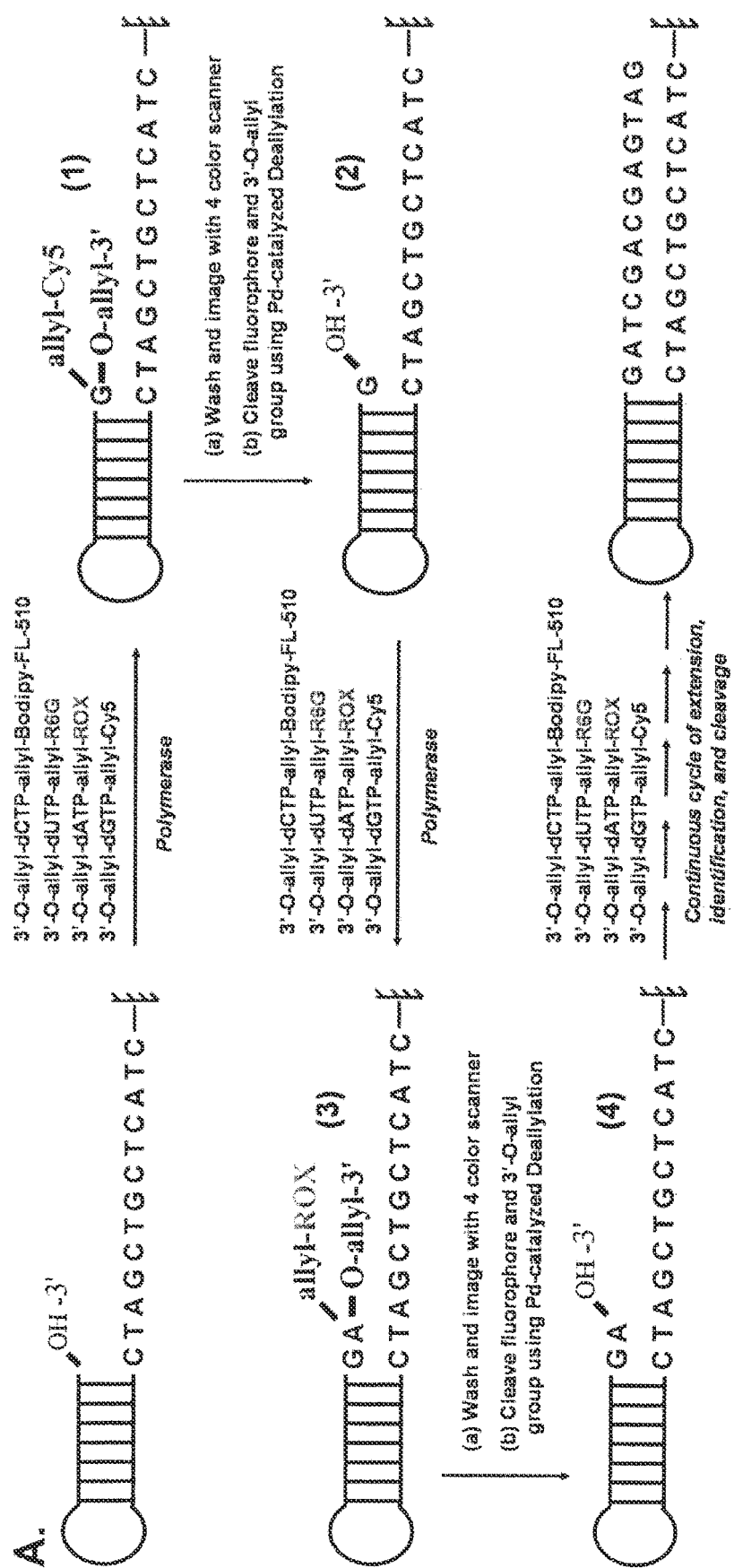
FIG. 6. (A) Reaction scheme of SBS on a chip using four chemically cleavable fluorescent nucleotides. (B) The scanned 4-color fluorescence images for each step of SBS on a chip: (1) incorporation of 3'-O-allyl-dGTP-allyl-Cy5; (2) cleavage of allyl-Cy5 and 3'-allyl group; (3) incorporation of 3'-O-allyl-dATP-allyl-ROX; (4) cleavage of allyl-ROX and 3'-allyl group; (5) incorporation of 3'-O-allyl-dUTP-allyl-R6G; (6) cleavage of allyl-R6G and 3'-allyl group; (7) incorporation of 3'-O-allyl-dCTP-allyl-Bodipy-FL-510; (8) cleavage of allyl-Bodipy-FL-510 and 3'-allyl group; images (9) to (25) are similarly produced. (C) A plot (4-color sequencing data) of raw fluorescence emission intensity at the four designated emission wavelength of the four chemically cleavable fluorescent nucleotides.
Figure 6:
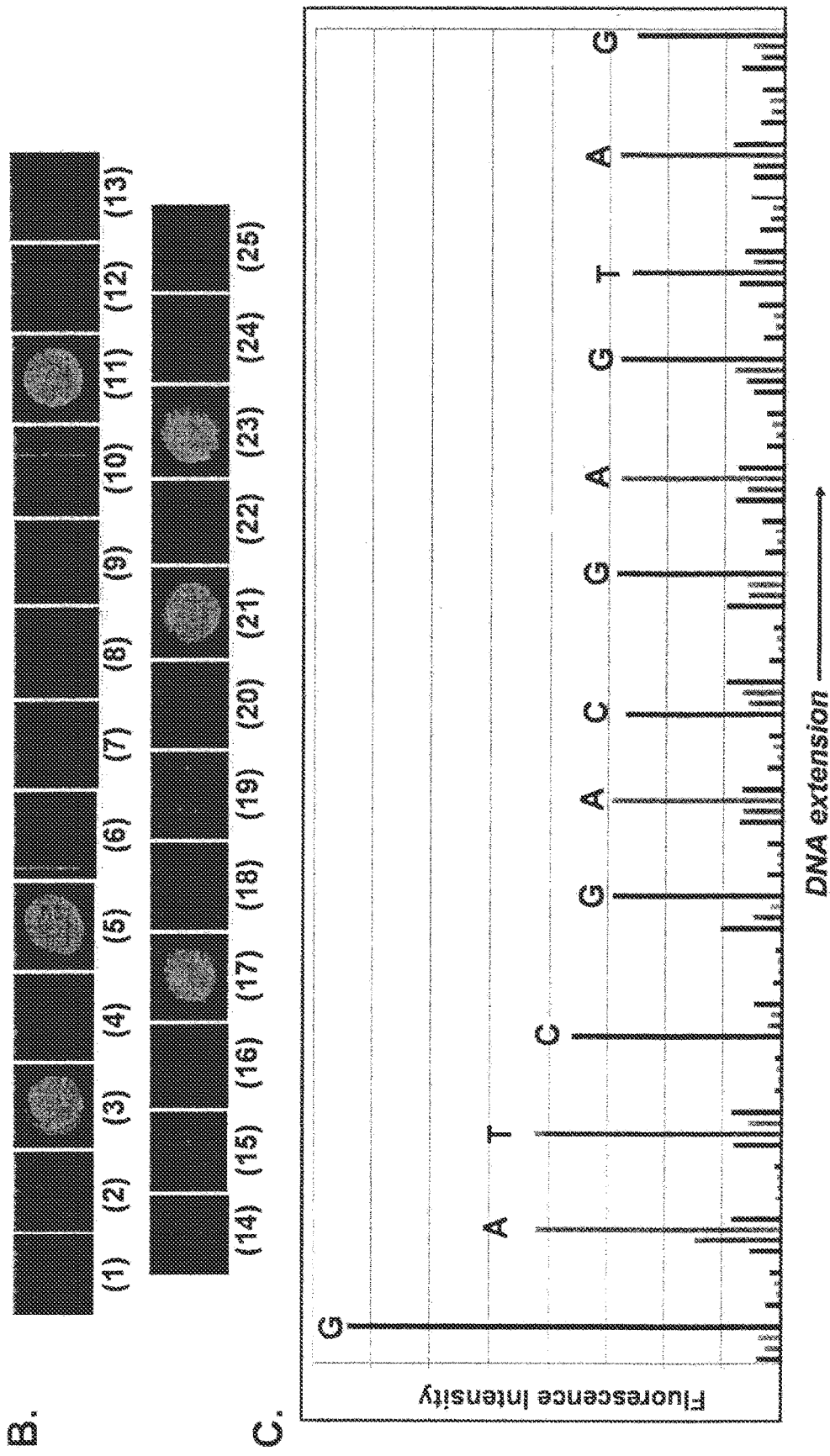
Figure 7:
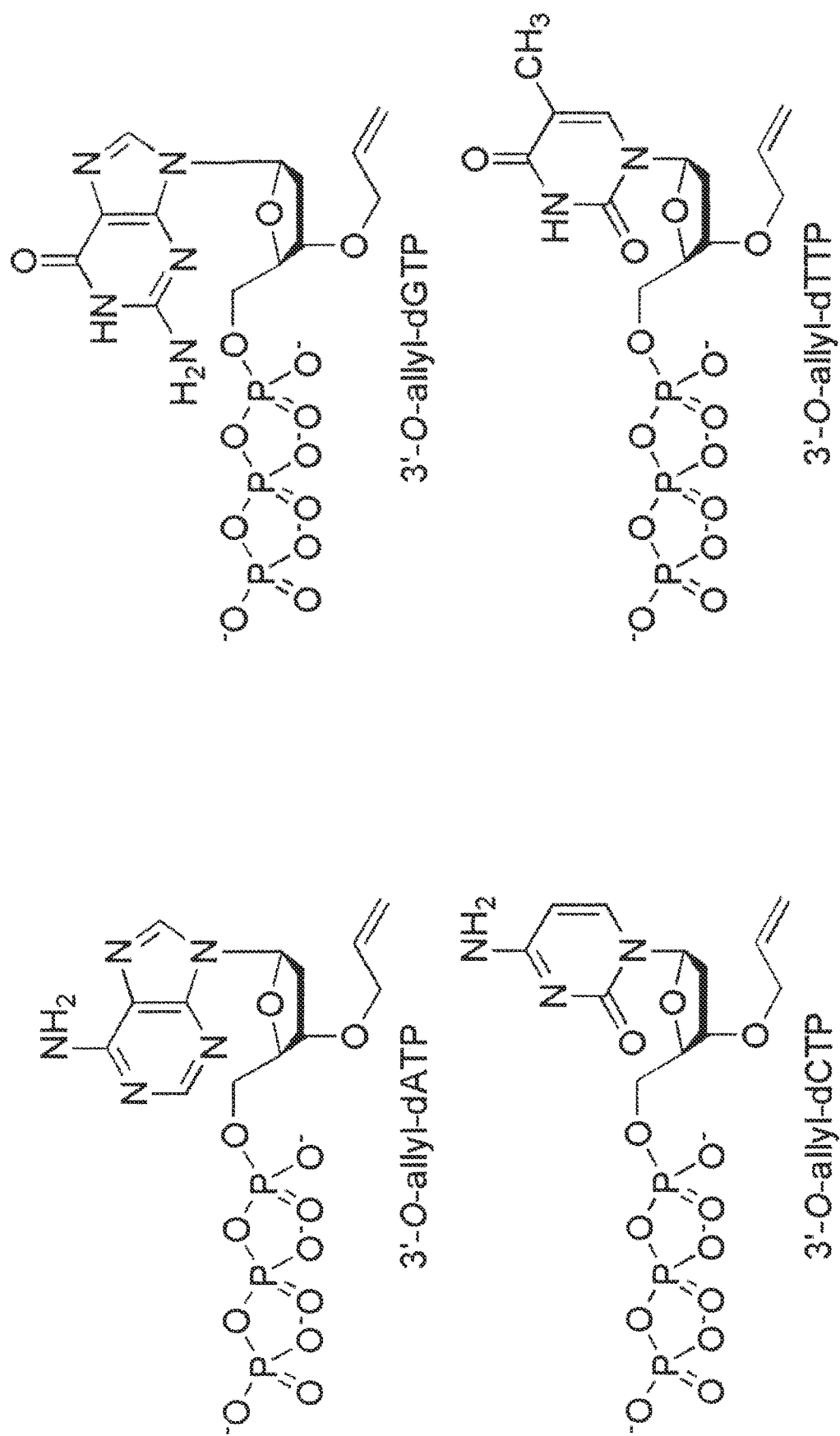
FIG. 7. Structures of 3'-O-allyl-dATP, 3'-O-allyl-dCTP, 3'-O-allyl-dGTP, and 3'-O-allyl-dTTP.

SBS was first performed on a chip-immobilized DNA template that has no homopolymer sequences using the four chemically cleavable fluorescent nucleotide reversible terminators (3'-O-allyl-dCTP-allyl-Bodipy-FL-510, 3'-O-allyl-dUTP-allyl-R6G, 3'-O-allyl-dATP-allyl-ROX and 3'-O-allyl-dGTP-allyl-Cy5) and the results are shown in FIG. 6. The structure of the self-priming DNA moiety is shown schematically in FIG. 6A, with the first 13 nucleotide sequences immediately after the priming site. The de novo sequencing reaction on the chip was initiated by extending the self-priming DNA using a solution containing all four 3'-O-allyl-dNTPs-allyl-fluorophore, and a 9° N mutant DNA polymerase. In order to negate any lagging fluorescence signal that is caused by previously unextended priming strand, a synchronization step was added to reduce the amount of unextended priming strands after the extension with the fluorescent nucleotides. A synchronization reaction mixture consisting of all four 3'-O-allyl-dNTPs (FIG. 7), which have a higher polymerase incorporation efficiency due to the lack of a fluorophore compared to the bulkier 3'-O-allyl-dNTPs-allyl-fluorophore, was used along with the 9° N mutant DNA polymerase to extend any remaining priming strand that has a free 3'-OH group to synchronize the incorporation. The extension by 3'-O-allyl-dNTPs also enhances the enzymatic incorporation of the next nucleotide analogue, because after cleavage to remove the 3'-O-allyl group, the DNA product extended by 3'-O-allyl-dNTPs carry no modification groups. After washing, the extension of the primer by only the complementary fluorescent nucleotide was confirmed by observing a red signal (the emission from Cy5) in a 4-color fluorescent scanner [FIG. 6B (1)]. After detection of the fluorescent signal, the chip surface was immersed in a deallylation cocktail [1× Thermolpol I reaction buffer/$Na_2PdCl_4$/P($PhSO_3Na$)$_3$] and incubated for 5 min at 60° C. to cleave both the fluorophore and 3'-O-allyl group simultaneously. The chip was then immediately immersed in a 3 M Tris-HCl buffer (pH 8.5) and incubated for 5 min at 60° C. to remove the Pd complex. The surface was then washed, and a negligible residual fluorescent signal was detected to confirm cleavage of the fluorophore. This was followed by another extension reaction using 3'-O-allyl-dNTPs-allyl-fluorophore mixture to incorporate the next fluorescent nucleotide complementary to the subsequent base on the template. The entire process of incorporation, synchronization, detection and cleavage was performed multiple times using the four chemically cleavable fluorescent nucleotide reversible terminators to identify 13 successive bases in the DNA template. The fluorescence image of the chip for each nucleotide addition is shown in FIG. 6B, while a plot of the fluorescence intensity vs. the progress of sequencing extension (raw 4-color sequencing data) is shown in FIG. 6C. The DNA sequences are unambiguously identified from the 4-color raw fluorescence data without any processing.

Comparison of 4-Color SBS with Pyrosequencing.

Figure 8:
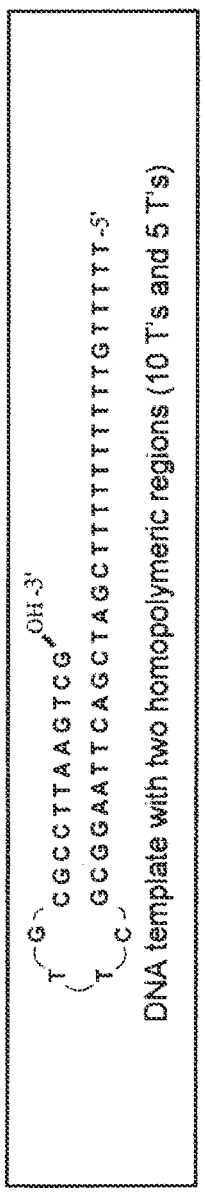
FIG. 8. (A) 4-color DNA sequencing raw data with our sequencing by synthesis chemistry using a template containing two homopolymeric regions. The individual base (A, T, C, G), the 10 repeated A's and the 5 repeated A's are clearly identified. The small groups of peaks between the identified bases are fluorescent background from the DNA chip, which does not build up as the cycle continues. (B) The pyrosequencing data of the same DNA template containing the homopolymeric regions (10 T's and 5 T's). The first 4 individual bases are clearly identified. The two homopolymeric regions (10 A's) and (5 A's) produce two large peaks, making it very difficult to determine the exact sequence from the data.
Figure 8:
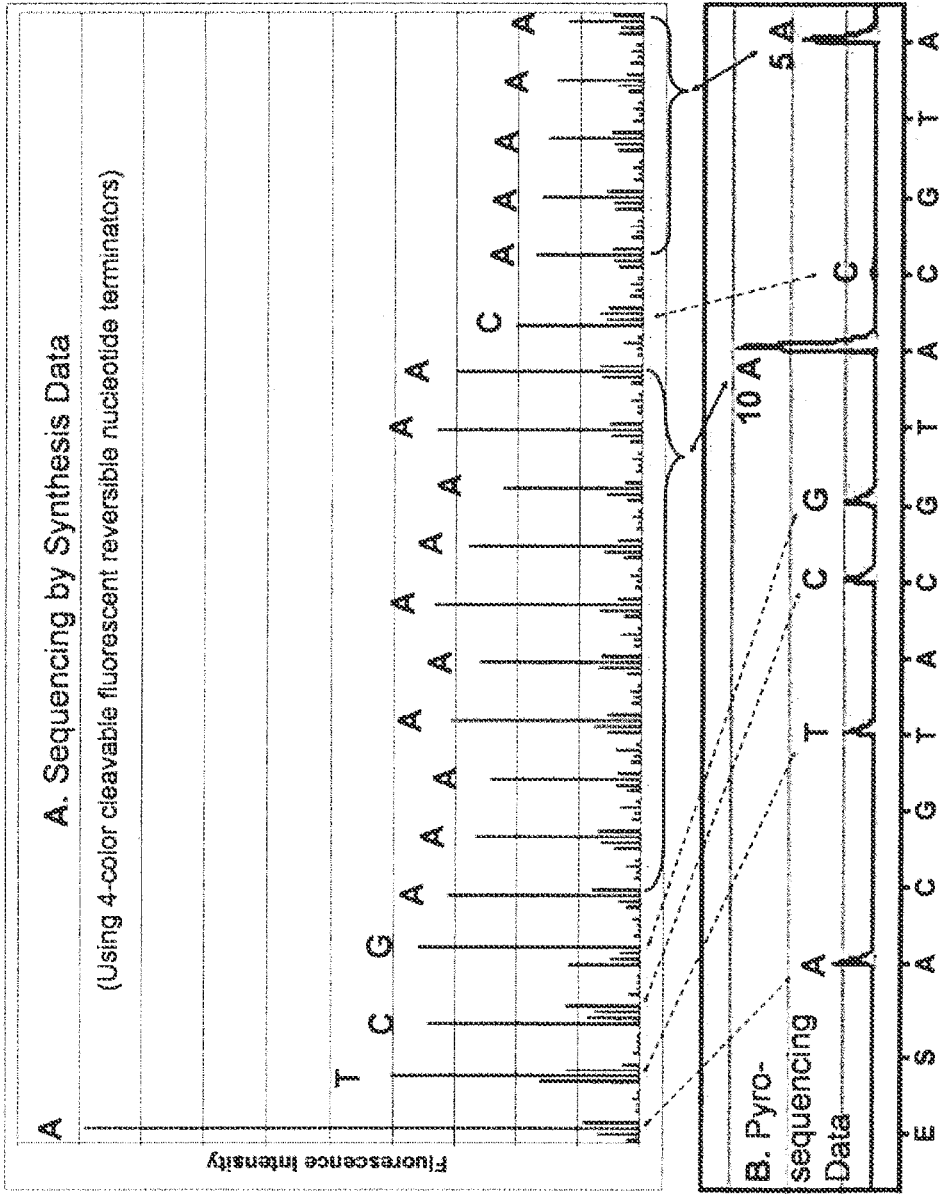

To further verify the advantage of SBS method using the four chemically cleavable fluorescent nucleotide reversible terminators, we carried out similar sequencing reaction as described above on a DNA template which contained two separate homopolymeric regions (stretch of 10 T's and 5 T's) as shown in FIG. 8 (panel A). These sequencing raw data were produced by adding all 4 fluorescent nucleotide reversible terminators together to the DNA template immobilized on the chip followed by synchronization reaction with four 3'-O-allyl-dNTPs, detecting the unique fluorescence emission for sequence determination, then cleaving the fluorophore and the 3'-O-allyl group in one step to continue the sequencing cycles. All 20 bases including the individual base (A, T, C, G), the 10 repeated A's and the 5 repeated A's are clearly identified. The small groups of peaks between the identified bases are fluorescent background from the DNA chip, which does not build up as the cycle continues. Panel B in FIG. 8 shows the pyrosequencing data of the same DNA template containing the homopolymeric sequences. The first 4 individual bases are clearly identified. The two homopolymeric regions (10 A's)

and (5 A's) produce two large peaks, but it is very difficult to identify the exact sequence from the data.

CONCLUSION

Four novel chemically cleavable fluorescent nucleotide analogues have been synthesized and characterized and have been used to produce a 4-color de novo DNA sequencing data on a chip. In doing so, two critical requirements for using SBS method to sequence DNA have been achieved unambiguously. First, a strategy to use a chemically reversible moiety to cap the 3'-OH group of the nucleotide has been successfully implemented so that the nucleotide terminates the polymerase reaction to allow the identification of the incorporated nucleotide. In addition these reversible terminators allow for the addition of all four nucleotides simultaneously in performing SBS. This ultimately reduces the number of cycles needed to complete the sequencing cycle, increases sequencing accuracy due to competition of the 4 nucleotides in the polymerase reaction, and enables accurate determination of homopolymeric regions of DNA template. Second, efficient removal of both the fluorophore and the 3'-OH capping group after the fluorescence signal detection have successfully been carried out which increases the overall efficiency of SBS.

The key factor governing the sequencing readlength of our 4-color SBS approach is the stepwise yield that are determined by the nucleotide incorporation efficiency and the yield of the cleavage of the fluorophore and the 3'-OH capping group from the DNA extension products. This stepwise yield here is ~ 99% based on measurement of the DNA products in solution phase. The yield on the surface is difficult to measure precisely due to fluctuations in the fluorescence imaging using the current manual fluorescent scanner. The strong fluorescence signal even for the 20$^{th}$ base shown in FIG. 8 indicates that we should be able to extend the readlength even further. In terms of readlength, Sanger sequencing is still the gold standard with readlength of over 800 bp but limited in throughput and cost. The readlength of pyrosequencing is ~100 bp but with high error rate due to difficulty in accurately determining the sequences of homopolymers. The 4-color SBS readlength on a manual fluorescent scanner is currently at ~20 bp with high accuracy. This readlength will increase with automation of the extension, cleavage and washing steps. The DNA polymerases and fluorescent labeling used in the automated 4-color Sanger sequencing method have undergone almost two decades of consistent incremental improvements after the basic fluorescent Sanger methods were established (2, 3). Following the same route, it is expected that the basic principle and strategy outlined in our 4-color SBS method will stimulate further improvement of the sequencing by synthesis methodology with engineering of high performance polymerases tailored for the cleavable fluorescent nucleotide terminators and testing alternative linkers and 3'-OH reversible capping moiety. It has been well established that using emulsion PCR on microbeads, millions of different DNA templates are immobilized on a surface of a chip (11, 16). This high density DNA templates coupled with our 4-color SBS approach will generate a high-throughput (>20 millions bases/chip) and high-accurate platform for a variety of sequencing and digital gene expression analysis projects.

Materials and Methods $^{1}$H NMR spectra were recorded on a Bruker DPX-400 (400 MHz) spectrometer and reported in ppm from a CD$_3$OD or DMSO-d$_6$ internal standard (3.31 or 2.50 ppm respectively). Data were reported as follows: (s=singlet, d=doublet, t=triplet, q=quartet, m=multiplet, dd=doublet of doublets, ddd=doublet of doublets of doublets; coupling constant(s) in Hz; integration; assignment). Proton decoupled $^{13}$C NMR spectra were recorded on a Bruker DPX-400 (100 MHz)

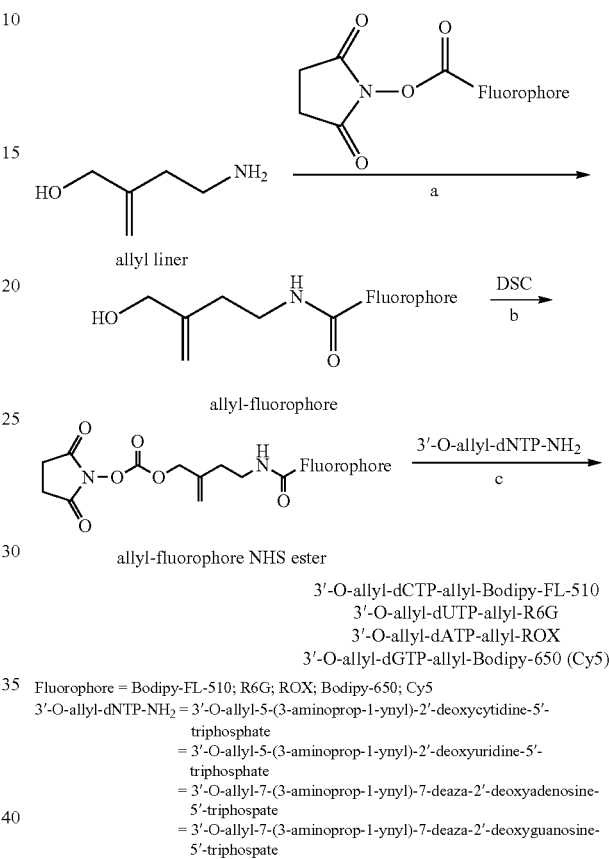

3'-O-allyl-dCTP-allyl-Bodipy-FL-510
3'-O-allyl-dUTP-allyl-R6G
3'-O-allyl-dATP-allyl-ROX
3'-O-allyl-dGTP-allyl-Bodipy-650 (Cy5)

Fluorophore = Bodipy-FL-510; R6G; ROX; Bodipy-650; Cy5
3'-O-allyl-dNTP-NH$_2$ = 3'-O-allyl-5-(3-aminoprop-1-ynyl)-2'-deoxycytidine-5'-triphosphate
= 3'-O-allyl-5-(3-aminoprop-1-ynyl)-2'-deoxyuridine-5'-triphosphate
= 3'-O-allyl-7-(3-aminoprop-1-ynyl)-7-deaza-2'-deoxyadenosine-5'-triphospate
= 3'-O-allyl-7-(3-aminoprop-1-ynyl)-7-deaza-2'-deoxyguanosine-5'-triphospate Synthetic scheme to prepare the chemically cleavable fluorescent nucleotides a, DMF/1 M NaHCO$_3$ solution; b, N, N'-disuccinimidyl carbonate (DSC), triethylamine; c, 0.1 M NaHCO$_3$/Na$_2$CO$_3$ aqueous buffer (pH 8.7) spectrometer and reported in ppm from a CD$_3$OD, DMSO-de or CDCl$_3$ internal standard (49.0, 39.5 or 77.0 ppm respectively). Proton decoupled $^{31}$P NMR spectra were recorded on a Bruker DPX-300 (121.4 MHz) spectrometer and reported in ppm from an 85% H$_3$PO$_4$ external standard. High Resolution Mass Spectra (HRMS) were obtained on a JEOL JMS HX 110A mass spectrometer. Compounds 30 and 32 were purchased from Berry & Associates. All Dye NHS esters were purchased from Molecular Probes and GE Healthcare. All other chemicals were purchased from Sigma-Aldrich.

I. Synthesis of 3'-O-allyl-dNTPs-allyl-Fluorophore

Chemically cleavable fluorescent nucleotides 3'-O-allyl-dCTP-allyl-Bodipy-FL-510, 3'-O-allyl-dUTP-allyl-R6G, 3'-O-allyl-dATP-allyl-ROX, 3'-O-allyl-dGTP-allyl-Bodipy-650 and 3'-O-allyl-dGTP-allyl-Cy5 were synthesized according to the above Scheme. A chemically cleavable linker 4-amino-2-methylene-1-butanol (allyl-linker) was reacted with the N-hydroxysuccinimide (NHS) ester of the corresponding fluorescent dye to produce an intermediate allyl-fluorophore, which was converted to an allyl-fluorophore NHS ester by reacting with N,N'-disuccinimidyl carbonate. The coupling reaction between the different allyl-fluorophore NHS esters and 3'-O-allyl-dNTPs-NH$_2$ produced the four chemically cleavable fluorescent nucleotides.

1. Synthesis of Allyl-Linker

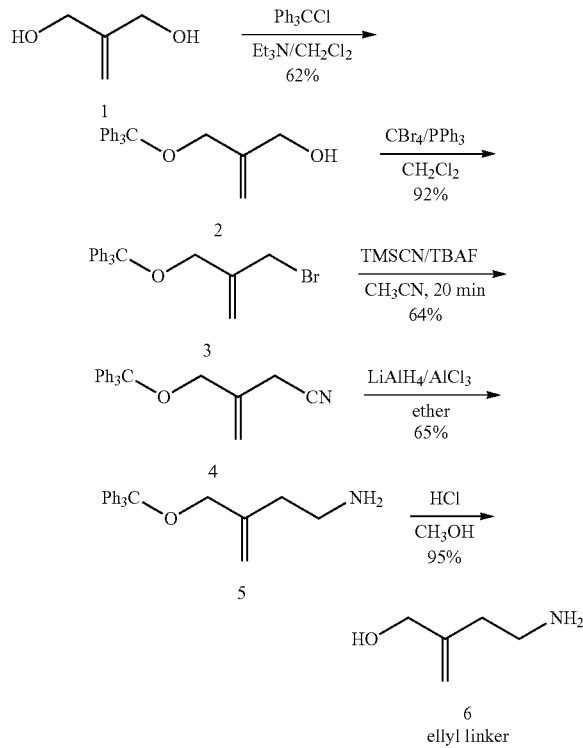

ellyl linker

2-Triphenylmethoxymethyl-2-propen-1-ol (2). To a stirred solution of trityl chloride (4.05 g; 14.3 mmol) and 2-methylenepropane-1,3-diol 1 (1.20 mL; 14.3 mmol) in dry CH$_2$Cl$_2$ (20 mL), triethylamine (4.0 mL; 28.5 mmol) was added slowly at room temperature. The mixture was stirred at room temperature for 1 h, and then ethyl acetate (100 mL) and saturated aqueous NaHCO$_3$ (30 mL) were added. The organic phase was washed with saturated aqueous NaHCO$_3$, NaCl, and dried over anhydrous Na$_2$SO$_4$. After evaporation, the residue was purified by flash column chromatography using ethyl acetate-hexane (1:10~5) as the eluent to afford 2 as a white solid (2.89 g; 62% yield): $^1$H NMR (400 MHz, CDCl$_3$) δ 7.42-7.48 (m, 6H, six of ArH), 7.27-7.33 (m, 6H, six of ArH), 7.20-7.27 (m, 3H, three of ArH), 5.26 (s, 1H, one of C=CH$_2$), 5.17 (s, 1H, one of C=CH$_2$), 4.13 (d, J=6.1 Hz, 2H, CH$_2$OH), 3.70 (s, 2H, Ph$_3$COCH$_2$), 1.72 (t, J=6.1 Hz, 1H, CH$_2$OH); $^{13}$C NMR (100 MHz, CDCl$_3$) δ 145.4, 143.6, 128.3, 127.6, 126.8, 111.6, 87.0, 65.3, 64.5.

1-Bromo-2-triphenylmethoxymethyl-2-propene (3). To a stirred solution of 2 (2.56 g; 7.74 mmol) in CH$_2$Cl$_2$ (75 mL), CBr$_4$ (3.63 g; 10.83 mmol) and triphenylphosphine (2.47 g; 9.31 mmol) were added respectively at 0° C. The mixture was stirred at room temperature for 40 min. Ethyl acetate (100 mL) and saturated aqueous NaHCO$_3$ (30 mL) were added at 0° C. The organic phase was washed with saturated aqueous NaCl, and dried over anhydrous Na$_2$SO$_4$. After evaporation, the residue was purified by flash column chromatography using CH$_2$Cl$_2$-hexane (1:5) as the eluent to afford 3 as white solid (3.02 g; 92% yield): $^1$H NMR (400 MHz, CDCl$_3$) δ 7.42-7.48 (m, 6H, six of ArH), 7.27-7.33 (m, 6H, six of ArH), 7.20-7.27 (m, 3H, three of ArH), 5.37 (s, 1H, one of C=CH$_2$), 5.31 (s, 1H, one of C=CH$_2$), 4.01 (s, 2H, CH$_2$Br), 3.75 (s, 2H, Ph$_3$COCH$_2$); $^{13}$C NMR (100 MHz, CDCl$_3$) δ 143.6, 142.6, 128.4, 127.6, 126.9, 115.8, 86.9, 64.2, 33.5.

3-Triphenylmethoxymethyl-3-butenonitrile (4). To a stirred solution of 3 (1.45 g; 3.69 mmol) and in dry CH$_3$CN (37 mL), trimethylsilyl cyanide (0.49 mL; 3.69 mmol) was added. Then, 1 M tetrabutylammonium fluoride (TBAF) in THF solution (3.69 mL, 3.69 mmol) was added into the above reaction mixture slowly at room temperature. The mixture was stirred for 20 min. After evaporation, the residue was diluted with ethyl acetate (100 mL) and saturated aqueous NaHCO$_3$ (30 mL). The organic phase was washed with saturated aqueous NaCl and dried over anhydrous Na$_2$SO$_4$. After evaporation, the residue was purified by flash column chromatography using acetate-hexane (1:10) as the eluent to afford 4 as white solid (1.01 g; 64% yield): $^1$H NMR (400 MHz, CDCl$_3$) δ 7.39-7.45 (m, 6H, six of ArH), 7.21-7.34 (m, 9H, nine of ArH), 5.31 (s, 2H, C=CH$_2$), 3.64 (s, 2H, Ph$_3$COCH$_2$), 3.11 (s, 2H, CH$_2$CN); $^{13}$C NMR (100 MHz, CDCl$_3$) δ 143.3, 135.5, 128.2, 127.7, 126.9, 116.8, 114.7, 87.0, 65.7, 21.9.

3-Triphenylmethoxymethyl-3-buten-1-amine (5). To a stirred solution of LiAlH$_4$ (119 mg; 2.98 mmol) in dry ether (5 mL), AlCl$_3$ (400 mg; 2.94 mmol) was added slowly at 0° C. and the mixture was stirred for 15 min. The mixture of 4 (829 mg; 2.44 mmol) in dry ether (9 mL) was added and then continued to stir at 0° C. for another 3 h. Afterwards, 10% aqueous NaOH (10 mL) was added to quench the reaction. The organic phase was washed with saturated aqueous NaHCO$_3$, NaCl, and dried over anhydrous K$_2$CO$_3$. After evaporation, the residue was further purified by flash column chromatography using CH$_3$OH—CH$_2$Cl$_2$ (1:20~5) as the eluent to afford 5 as colorless oil (545 mg; 65% yield): $^1$H NMR (400 MHz, CDCl$_3$) δ 7.41-7.48 (m, 6H, six of ArH), 7.26-7.33 (m, 6H, six of ArH), 7.19-7.26 (m, 3H, three of ArH), 5.33 (s, 1H, one of C=CH$_2$), 4.96 (s, 1H, one of C=CH$_2$), 3.53 (s, 2H, Ph$_3$COCH$_2$), 2.70 (m, 2H, CH$_2$CH$_2$NH$_2$), 2.18 (t, J=6.7 Hz, 2H, CH$_2$CH$_2$NH$_2$), 2.06 (br s, 2H, NH$_2$); $^{13}$C NMR (100 MHz, CDCl$_3$) δ 143.6, 143.4, 128.1, 127.4, 126.5, 111.3, 86.5, 66.1, 39.8, 37.4; HRMS (FAB+) calcd for C$_{24}$H$_{26}$ON (M+H$^+$): 344.2014, found: 344.2017.

4-Amino-2-methylene-1-butanol (6). To a stirred solution of 5 (540 mg; 1.57 mmol) in CH$_3$OH (11 mL), HCl (2M solution in ether; 5.5 mL) was added at room temperature and the mixture was stirred for 1 h. Then 7M ammonia in CH$_3$OH solution (2.7 mL) was added into the above mixture at room temperature and continued to stir for another 10 min. After filtration, the solid was washed with CH$_3$OH and combined with the filtrate. After evaporation, the crude product was further purified by flash column chromatography using CH$_3$OH—CH$_2$Cl$_2$ (1:4) as the eluent to afford 6 as colorless oil (151 mg; 95% yield): $^1$H NMR (400 MHz, CD$_3$OD) δ5.19 (s, 1H, one of C=CH$_2$), 5.01 (s, 1H, one of C=CH$_2$), 4.06 (s, 2H, CH$_2$OH), 3.10 (t, J=7.5 Hz, 2H, CH$_2$CH$_2$NH$_2$), 2.46 (t, J=7.5 Hz, 2H, CH$_2$CH$_2$NH$_2$); $^{13}$C NMR (100 MHz, CD$_3$OD) δ 145.3, 113.7, 65.5, 39.5, 32.0; MS (FAB+) calcd for C$_5$H$_{12}$ON (M+H$^+$): 102.09, found: 102.12.

2. Synthesis of Allyl-Fluorophore

A general procedure for the synthesis of Allyl-Fluorophore is as follows. To a stirred solution of 6 (3.5 mg; 34.6 μmol) in DMF (450 μL), aqueous NaHCO$_3$ (1M solution; 100 μL) was added at room temperature. The mixture was stirred for 5 min. Dye NHS (N-hydroxysuccinimide) ester (5 mg) in DMF (450 μL) was added and then the mixture was stirred at room temperature for 6 h. The crude product was further purified by a preparative TLC plate using CH$_3$OH—CH$_2$Cl$_2$ as the eluent to afford Allyl-Fluorophore.

Allyl-Bodipy-FL-510 (7). $^1$H NMR (400 MHz, CD$_3$OD) δ 7.42 (s, 1H), 7.00 (d, J=4.0 Hz, 1H), 6.32 (d, J=4.0 Hz, 1H), 6.21 (s, 1H), 5.06 (s, 1H, one of C=CH$_2$), 4.87 (s, 1H, one of C=CH$_2$, partly superimposed by solvent signal), 4.01 (s, 2H, CH$_2$OH), 3.33 (t, J=7.5 Hz, 2H, partly superimposed by solvent signal), 3.21 (t, J=7.7 Hz, 2H), 2.59 (t, J=7.7 Hz, 2H), 2.51 (s, 3H, one of ArCH$_3$), 2.28 (s, 3H), 2.26 (t, J=7.1 Hz, 2H); HRMS (FAB+) calcd for C$_{19}$H$_{24}$O$_2$N$_3$F$_2$B (M): 375.1933, found: 375.1957.

Allyl-R6G (8). $^1$H NMR (400 MHz, CD$_3$OD) δ 8.12 (d, J=8.1 Hz, 1H), 8.05 (dd, J=1.8, 8.1 Hz, 1H), 7.66 (d, J=1.6 Hz, 1H), 7.02 (s, 2H), 6.88 (s, 2H), 5.08 (s, 1H, one of C=CH$_2$), 4.92 (s, 1H, one of C=CH$_2$), 4.06 (s, 2H, CH$_2$OH), 3.48-3.56 (m, 6H), 2.40 (t, J=7.2 Hz, 2H), 2.13 (s, 6H), 1.36 (t, J=7.2 Hz, 6H); HRMS (FAB+) calcd for C$_{32}$H$_{36}$O$_5$N$_3$ (M+H$^+$): 542.2655, found: 542.2648.

Allyl-ROX (9). $^1$H NMR (400 MHz, CD$_3$OD) δ 8.03 (d, J=8.1 Hz, 1H), 7.98 (dd, J=1.6, 8.1 Hz, 1H), 7.60 (d, J=1.4 Hz, 1H), 6.75 (s, 2H), 5.08 (s, 1H, one of C=CH$_2$), 4.91 (s, 1H, one of C=CH$_2$), 4.05 (s, 2H, CH$_2$OH), 3.45-3.57 (m, 10H), 3.03-3.10 (m, 4H), 2.64-2.73 (m, 4H), 2.38 (t, J=7.1 Hz, 2H), 2.04-2.15 (m, 4H), 1.89-1.99 (m, 4H); HRMS (FAB+) calcd for C$_{38}$H$_{40}$O$_5$N$_3$ (M+H$^+$): 618.2968, found: 618.2961.

Allyl-Bodipy-650 (10). $^1$H NMR (400 MHz, CD$_3$OD) δ 8.12 (dd, J=0.9, 3.8 Hz, 1H), 7.63 (m, 3H), 7.54 (d, J=6.4 Hz, 2H), 7.35 (s, 1H), 7.18-7.22 (m, 2H), 7.12 (m, 2H), 7.06 (d, J=8.8 Hz, 2H), 6.85 (d, J=4.2 Hz, 1H), 5.06 (s, 1H, one of C=CH$_2$), 4.86 (s, 1H, one of C=CH$_2$), 4.56 (s, 2H), 4.00 (s, 2H, CH$_2$OH), 3.28 (m, 4H), 2.23 (t, J=7.1 Hz, 2H), 2.14 (t, J=7.5 Hz, 2H), 1.49-1.62 (m, 4H), 1.25-1.34 (m, 2H); HRMS (FAB+) calcd for C$_{34}$H$_{37}$O$_4$N$_4$F$_2$SB (M$^+$): 646.2603, found: 646.2620.

Allyl-Cy5 (11). $^1$H NMR (400 MHz, CD$_3$OD) δ 7.75-7.86 (m, 2H), 7.43-7.62 (m, 3H), 6.65 (m, 1H), 6.25-6.53 (m, 5H), 5.06 (s, 1H, one of C=CH$_2$), 4.86 (s, 1H, one of C=CH$_2$), 4.56 (s, 2H), 4.00 (s, 2H, CH$_2$OH), 3.28 (m, 6H), 2.03-2.40 (m, 4H), 1.55 (t, J=7.2 Hz, 3H), 1.31 (s, 6H), 1.26 (s, 6H), 1.25-1.64 (m, 6H); HRMS (FAB+) calcd for C$_{38}$H$_{48}$O$_8$N$_3$S$_2$ (M$^+$): 738.2888, found: 738.2867.

3. Synthesis of Allyl-Fluorophore NHS Ester

A general procedure for the synthesis of Allyl-Dye NHS ester is as follows. To a stirred solution of Allyl-Fluorophore (4 mg) in dry DMF (350 μL), DSC (8.0 mg; 31.2 μmol) and triethylamine (5.0 μL; 35.4 μmol) were added respectively. The reaction mixture was stirred at room temperature for 10 h. After evaporation, the crude product was further purified by flash column chromatography using CH$_3$OH—CH$_2$Cl$_2$ as the eluent to afford Allyl-Fluorophore NHS ester, which was used directly for the next step.

4. Synthesis of 3'-O-allyl-dCTP-allyl-Bodipy-FL-510 (23)

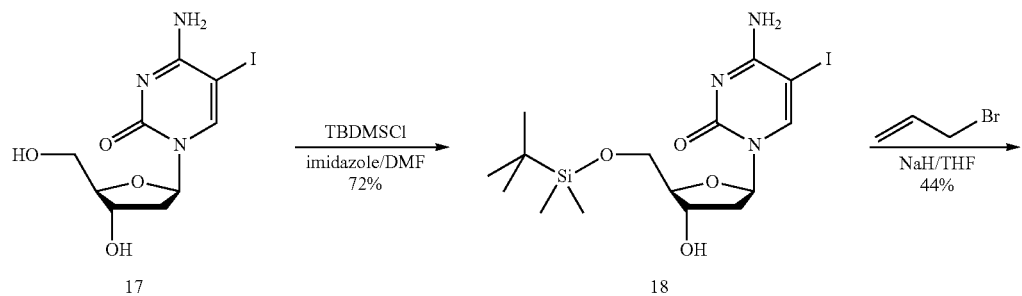

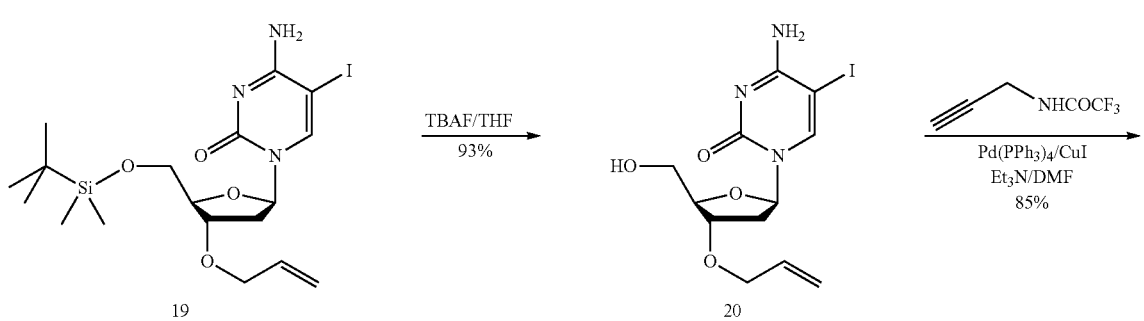

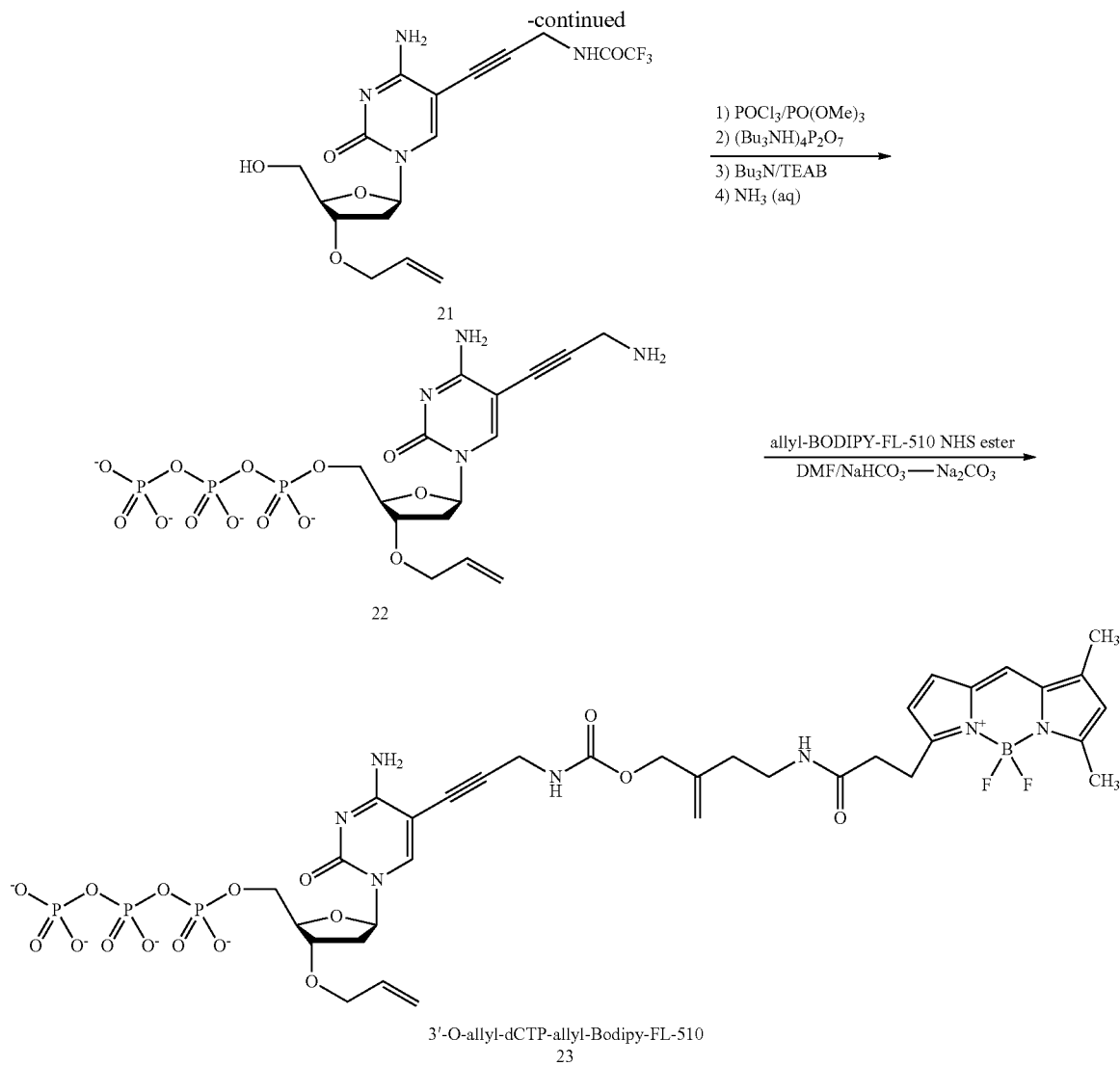

3'-O-allyl-dCTP-allyl-Bodipy-FL-510
23

5'-O-(tert-Butyldimethylsilyl)-5-iodo-2'-deoxycytidine (18). To a stirred mixture of 17 (1.00 g; 2.83 mmol) and imidazole (462 mg; 6.79 mmol) in anhydrous DMF (14.0 mL), tert-butyldimethylsilyl chloride (TBDMSCl) (510 mg; 3.28 mmol) was added. The reaction mixture was stirred at room temperature for 20 h. After evaporation, the residue was purified by flash column chromatography using $CH_3OH$—$CH_2Cl_2$ (1:20) as the eluent to afford 18 as white solid (1.18 g; 89% yield): $^1$H NMR (400 MHz, $CD_3OD$) δ 8.18 (s, 1H, 6-H), 6.17 (dd, J=5.8, 7.5 Hz, 1H, 1'-H), 4.34 (m, 1H, 3'-H), 4.04 (m, 1H, 4'-H), 3.93 (dd, J=2.5, 11.6 Hz, 1H, one of 5'-H), 3.84 (dd, J=2.9, 11.6 Hz, 1H, one of 5'-H), 2.41-2.48 (ddd, J=2.5, 5.8, 13.5 Hz, 1H, one of 2'-H), 2.01-2.08 (ddd, J=5.9, 7.6, 13.5 Hz, 1H, one of 2'-H), 0.95 (s, 9H, $C(CH_3)_3$), 0.17 (s, 3H, one of $SiCH_3$), 0.16 (s, 3H, one of $SiCH_3$); $^{13}$C NMR (100 MHz, $CD_3OD$) δ 165.5, 156.8, 147.8, 89.4, 88.3, 72.8, 64.6, 57.1, 43.1, 26.7, 19.4, −4.8, −4.9; HRMS (FAB+) calcd for $C_{15}H_{27}O_4N_3SiI$ (M+H$^+$): 468.0816, found: 468.0835.

3'-O-Allyl-5'-O-(tert-butyldimethylsilyl)-5-iodo-2'-deoxycytidine (19). To a stirred solution of 18 (1.18 g; 2.52 mmol) in anhydrous THF (43 mL), 95% NaH powder (128 mg; 5.07 mmol) was added. The suspension mixture was stirred at room temperature for 45 min. Allyl bromide (240 μL, 2.79 mmol) was then added at 0° C. and the reaction was stirred at room temperature for another 14 h with exclusion of moisture. Saturated aqueous $NaHCO_3$ (10 mL) was added at 0° C. and the reaction mixture was stirred for 10 min. After evaporation, the residue was dissolved in ethyl acetate (150 mL). The solution was then washed with saturated aqueous $NaHCO_3$ and NaCl, and dried over anhydrous $Na_2SO_4$. After evaporation, the residue was purified by flash column chromatography using ethyl acetate as the eluent to afford 19 as white solid (601 mg; 47% yield): $^1$H NMR (400 MHz, $CD_3OD$) δ 8.15 (s, 1H, 6-H), 6.12 (dd, J=5.6, 8.0 Hz, 1H, 1'-H), 4.17 (m, 1H, 4'-H), 4.14 (m, 1H, 3'-H), 3.98-4.10 (m, 2H, $CH_2CH=CH_2$), 3.93 (dd, J=2.8, 11.5 Hz, 1H, one of 5'-H), 3.83 (dd, J=2.8, 11.5 Hz, 1H, one of 5'-H), 2.53-2.60 (ddd, J=1.7, 5.6, 13.6 Hz, 1H, one of 2'-H), 1.94-2.02 (ddd, J=5.9, 8.0, 13.6 Hz, 1H, one of 2'-H), 0.94 (s, 9H, $C(CH_3)_3$), 0.17 (s, 3H, one of $SiCH_3$), 0.16 (s, 3H, one of $SiCH_3$); $^{13}$C NMR (100 MHz, $CD_3OD$) δ 165.4, 156.7, 147.7, 135.5, 117.2, 88.2, 87.0, 80.4, 70.9, 64.8, 57.3, 40.1, 26.7, 19.4, −4.7, −4.9; HRMS (FAB+) calcd for $C_{18}H_{31}O_4N_3SiI$ (M+H$^+$): 508.1129, found: 508.1123.

3'-O-Allyl-5-iodo-2'-deoxycytidine (20). To a stirred solution of 19 (601 mg; 1.18 mmol) in anhydrous THF (28 mL), 1 M TBAF in THF solution (1.31 mL; 1.31 mmol) was added and the reaction mixture was stirred at room temperature for 1 h. After evaporation, the residue was dissolved in ethyl acetate (100 mL). The solution was then washed with saturated aqueous NaCl and dried over anhydrous Na$_2$SO$_4$. After evaporation, the residue was purified by flash column chromatography using CH$_3$OH—CH$_2$Cl$_2$ (1:10) as the eluent to afford 20 as white crystals (329 mg; 71% yield): $^1$H NMR (400 MHz, CD$_3$OD) δ 8.47 (s, 1H, 6-H), 6.15 (dd, J=6.2, 6.7 Hz, 1H, 1'-H), 5.87-5.98 (m, 1H, CH$_2$CH=CH$_2$), 5.26-5.33 (dm, J=17.2 Hz, 1H, one of CH$_2$CH=CH$_2$), 5.14-5.19 (dm, J=10.5 Hz, 1H, one of CH$_2$CH=CH$_2$), 4.18 (m, 1H, 3'-H), 4.08 (m, 1H, 4'-H), 3.98-4.10 (m, 2H, CH$_2$CH=CH$_2$), 3.82 (dd, J=3.2, 13.0 Hz, 1H, one of 5'-H), 3.72 (dd, J=3.3, 13.0 Hz, 1H, one of 5'-H), 2.44-2.51 (ddd, J=3.2, 6.0, 13.6 Hz, 1H, one of 2'-H), 2.07-2.15 (m, 1H, one of 2'-H); $^{13}$C NMR (100 MHz, CD$_3$OD) δ 165.4, 156.9, 148.8, 135.6, 117.0, 87.9, 86.9, 79.6, 71.2, 62.7, 57.2, 39.7; HRMS (FAB+) calcd for C$_{12}$H$_{17}$O$_4$N$_3$I (M+H$^+$): 394.0264, found: 394.0274.

3'-O-Allyl-5-{3-[(trifluoroacetyl)amino]prop-1-ynyl}-2'-deoxycytidine (21). To a stirred solution of 20 (329 mg; 0.84 mmol) in anhydrous DMF (3.7 mL), tetrakis(triphenylphosphine)palladium(0) (97 mg; 0.084 mmol) and CuI (35 mg; 0.18 mmol) were added. The reaction mixture was stirred at room temperature for 10 min. Then N-propargyltrifluoroacetamide (379 mg; 2.51 mmol) and Et$_3$N (233 μL; 1.68 mmol) were added into the above reaction mixture. The reaction was stirred at room temperature for 1.5 h with exclusion of air and light. After evaporation, the residue was dissolved in ethyl acetate (100 mL). The mixture was washed with saturated aqueous NaHCO$_3$, NaCl, and dried over anhydrous Na$_2$SO$_4$. After evaporation, the residue was purified by flash column chromatography using CH$_3$OH—CH$_2$Cl$_2$ (0~1:10) as the eluent to afford 21 as yellow crystals (290 mg; 83% yield): $^1$H NMR (400 MHz, CD$_3$OD) δ 8.31 (s, 1H, 6-H), 6.17 (dd, J=6.0, 7.3 Hz, 1H, 1'-H), 5.87-5.97 (m, 1H, CH$_2$CH=CH$_2$), 5.26-5.33 (dm, J=17.3 Hz, 1H, one of CH$_2$CH=CH$_2$), 5.15-5.19 (dm, J=10.4 Hz, 1H, one of CH$_2$CH=CH$_2$), 4.31 (s, 2H, C≡CCH$_2$), 4.17 (m, 1H, 3'-H), 4.09 (m, 1H, 4'-H), 3.98-4.10 (m, 2H, CH$_2$CH=CH$_2$), 3.80 (dd, J=3.4, 12.0 Hz, 1H, one of 5'-H), 3.72 (dd, J=3.6, 12.0 Hz, 1H, one of 5'-H), 2.46-2.53 (ddd, J=2.9, 5.3, 13.6 Hz, 1H, one of 2'-H), 2.04-2.12 (m, 1H, one of 2'-H); $^{13}$C NMR (100 MHz, CD$_3$OD) δ 166.0, 158.4 (q, J=38 Hz, COCF$_3$), 156.3, 145.8, 135.6, 117.1 (q, J=284 Hz, COCF$_3$), 117.0, 91.9, 90.7, 88.0, 87.0, 79.8, 75.5, 71.2, 62.8, 39.6, 31.0; HRMS (FAB+) calcd for C$_{17}$H$_{20}$O$_5$N$_4$F$_3$ (M+H$^+$): 417.1386, found: 417.1377.

3'-O-Allyl-5-(3-aminoprop-1-ynyl)-2'-deoxycytidine-5'-triphosphate (22). 21 (133 mg; 0.319 mmol) and proton sponge (83.6 mg; 0.386 mmol) were dried in a vacuum desiccator over P$_2$O$_5$ overnight before dissolving in trimethylphosphate (0.60 mL). Freshly distilled POCl$_3$ (36 μL; 0.383 mmol) was added dropwise at 0° C. and the mixture was stirred for 3 h. Then the solution of tributylammonium pyrophosphate (607 mg) and tributylamine (0.61 mL; 2.56 mmol) in anhydrous DMF (2.56 mL) was well vortexed and added in one portion at room temperature and the reaction mixture was stirred for 30 min. After that triethylammonium bicarbonate solution (TEAB) (0.1 M; 16 mL) was added and the mixture was stirred for 1 h. Then aqueous ammonia (28%; 16 mL) was added and the reaction mixture was stirred for 12 h. After most liquid was removed under vacuum, the residue was redissolved in water (2 mL) and filtered. The aqueous solution was purified by DEAE Sephadex A25 ion exchange column using gradient aqueous TEAB solution (from 0.1 M to 1.0 M) as eluent to afford 22 as colorless syrup after evaporation: $^1$H NMR (300 MHz, D$_2$O) δ 8.43 (s, 1H, 6-H), 6.21 (t, J=6.7 Hz, 1H, 1'-H), 5.85-6.00 (m, 1H, CH$_2$CH=CH$_2$), 5.28-5.38 (dm, J=17.3 Hz, 1H, one of CH$_2$CH=CH$_2$), 5.19-5.27 (dm, J=10.4 Hz, 1H, one of CH$_2$CH=CH$_2$), 4.22-4.41 (m, 3H, 3'-H and C≡CCH$_2$), 4.05-4.18 (m, 3H, 4'-H and CH$_2$CH=CH$_2$), 3.94-4.01 (m, 2H, 5'-H), 2.47-2.59 (m, 1H, one of 2'-H), 2.20-2.32 (m, 1H, one of 2'-H); $^{31}$P NMR (121.4 MHz, D$_2$O) δ −7.1 (d, J=19.8 Hz, 1P, γ-P), −11.1 (d, J=19.1 Hz, 1P, α-P), −21.9 (t, J=19.5 Hz, 1P, β-P).

3'-O-Allyl-dCTP-allyl-Bodipy-FL-510 (23). To a stirred solution of allyl-Bodipy-FL-510 NHS ester 12 in DMF (300 μL), 3'-O-allyl-dCTP-NH$_2$ 22 in 1M NaHCO$_3$—Na$_2$CO$_3$ buffer (300 μL; pH 8.7) was added. The reaction mixture was stirred at room temperature for 7 h and the crude product was purified by a preparative TLC plate using CH$_3$OH—CH$_2$Cl$_2$ (1:1) as the eluent. The crude product was further purified by reverse-phase HPLC using a 150×4.6 mm C18 column to afford compound 23 (retention time=35 min). Mobile phase: A, 4.4 mM Et$_3$N/98.3 mM 1,1,1,3,3,3-hexafluoro-2-propanol in water (pH=8.1); B, methanol. Elution was performed from 100% A isocratic over 10 min followed by a linear gradient of 0-50% B for 20 min and then 50% B isocratic over 20 min. The product was characterized by the following single base extension reaction to generate DNA extension product 24 and characterized by MALDI-TOF MS.

A general procedure of primer extension using 3'-O-allyl-dNTPs-allyl-Fluorophore. The polymerase extension reaction mixture consisted of 50 pmol of primer (5'-GTT-GATGTACACATTGTCAA-3', SEQ ID NO:1), 80 pmol of 100-mer template (5'-TACCCGGAGGC-CAAGTACGGCGGGTACGTCCTTGACAATGTGTA-CATCAACATC ACCTACCAC-CATGTCAGTCTCGGTTGGATCCTCTATTGTGTCCGG G-3', SEQ ID NO:2), 120 pmol of 3'-O-allyl-dNTP-allyl-Fluorophore, 1× Thermopol II reaction buffer [20 mM Tris-HCl/10 mM (NH$_4$)$_2$SO$_4$/10 mM KCl/2 mM MnCl$_2$/0.1% Triton X-100, pH 8.8, New England Biolabs], and 6 units of 9° N Polymerase (exo-)A485L/Y409V in a total volume of 20 μL. The reaction consisted of 20 cycles at 94° C. for 20 sec, 46° C. for 40 sec, and 60° C. for 90 sec. After the reaction, a small portion of the DNA extension product was desalted using a ZipTip and analyzed by MALDI-TOF MS, which showed a dominant peak at m/z 5935 corresponding to the DNA extension product generated by incorporating 23. The rest of the product was subjected to the following deallylation.

General one-pot dual-deallylation procedure of DNA extension products. The DNA product from above (20 pmol) was added to a mixture of degassed 1× Thermopol I reaction buffer (20 mM Tris-HCl/10 mM (NH$_4$)$_2$SO$_4$/10 mM KCl/2 mM MgSO$_4$/0.1% Triton X-100, pH 8.8, 1 μL), Na$_2$PdCl$_4$ in degassed H$_2$O (7 μL, 23 nmol) and P(PhSO$_3$Na)$_3$ in degassed H$_2$O (10 μL, 176 nmol) to perform an one-pot dual-deallylation reaction. The reaction mixture was then placed in a heating block and incubated at 70° C. for 30 seconds to yield quantitatively deallylated DNA product and characterized by MALDI-TOF MS as a single peak.

Figure 9:
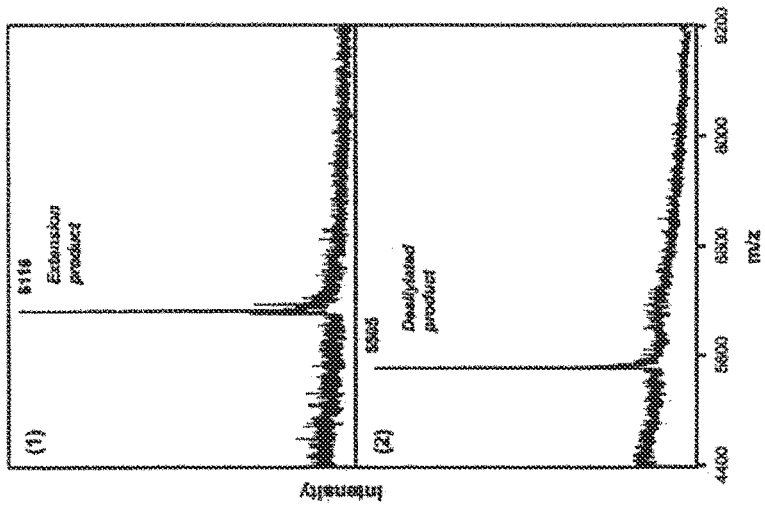
FIG. 9. Single base extension reaction and MALDI-TOF MS of 3'-O-Allyl-dUTP-allyl-R6G.
Figure 9:
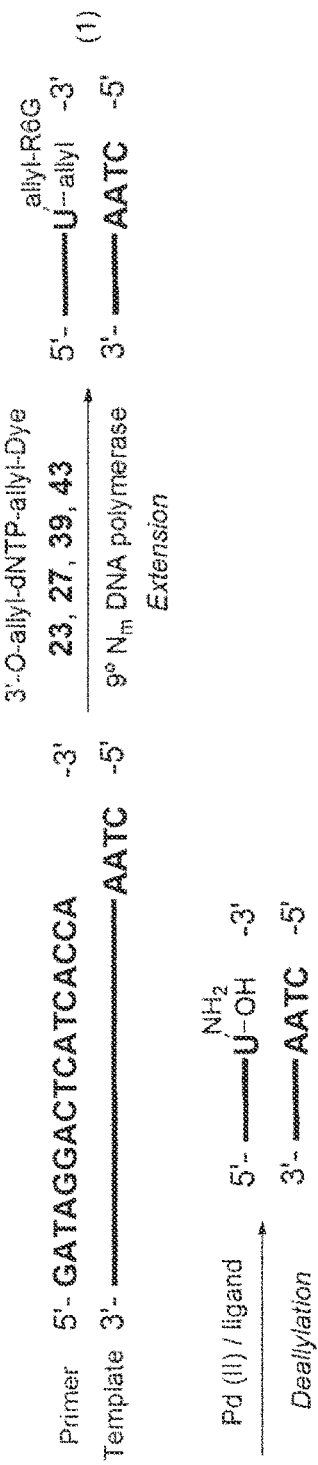
Figure 9:
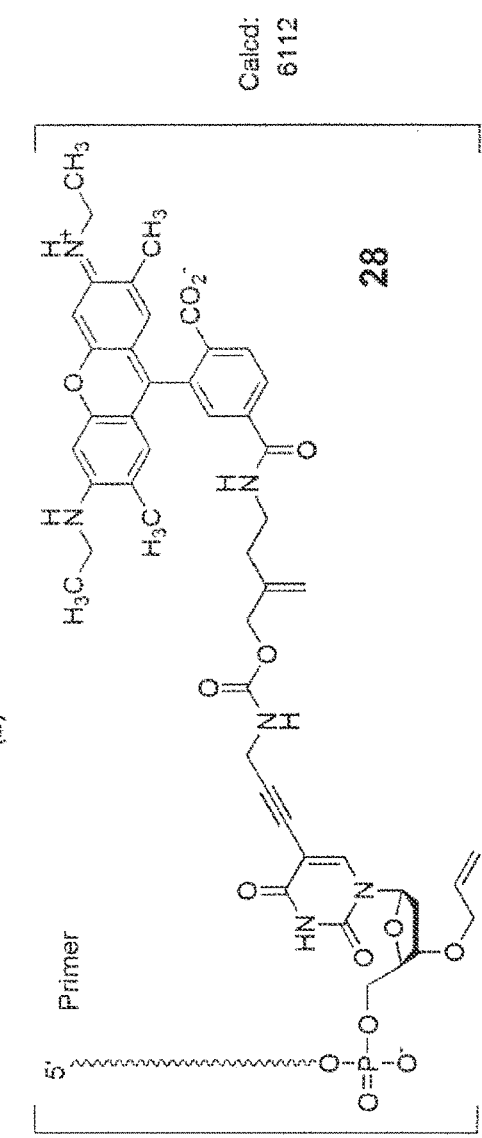
Figure 9:
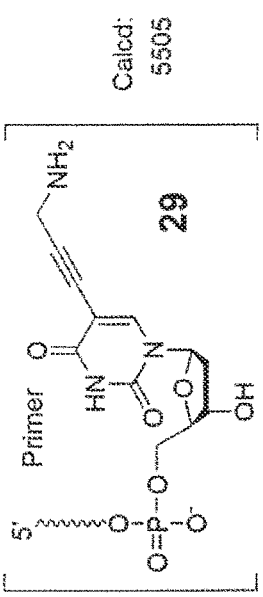

5. Synthesis of 3'-O-allyl-dUTP-allyl-R6G (27)
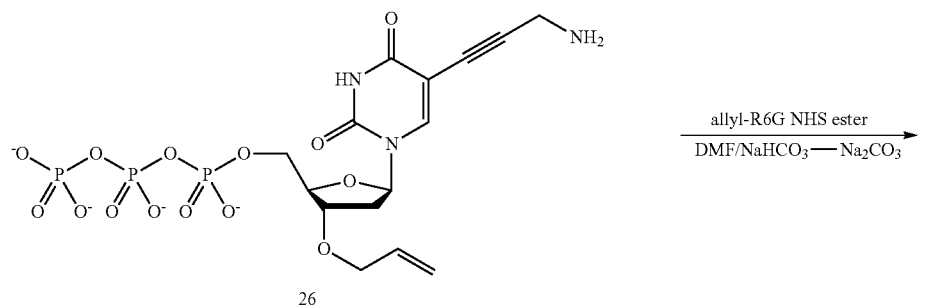
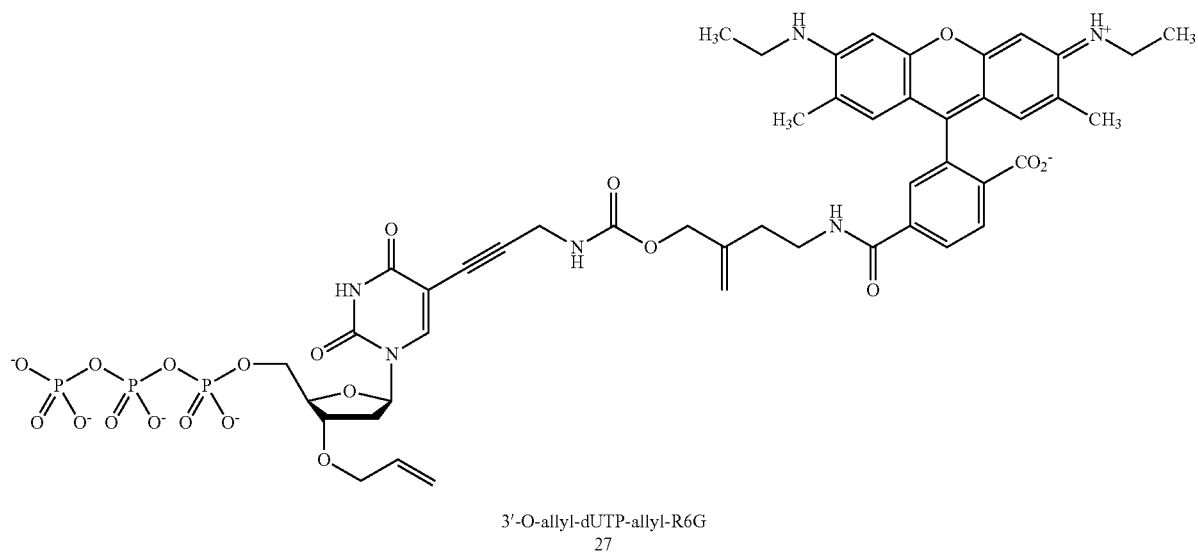
3'-O-allyl-dUTP-allyl-R6G
27
Synthesis of 3'-O-allyl-dUTP-$NH_2$ 26 was performed according to the procedures in reference (28).
3'-O-Allyl-dUTP-allyl-R6G (27). The procedure was similar to the synthesis of 23. The product was characterized by the single base extension reaction and MALDI-TOF MS in FIG. 9.
6. Synthesis of 3'-O-allyl-dATP-allyl-ROX (39)
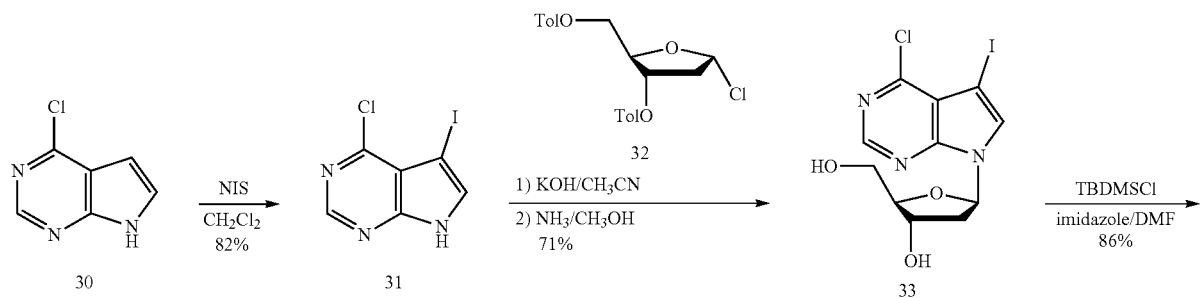

-continued
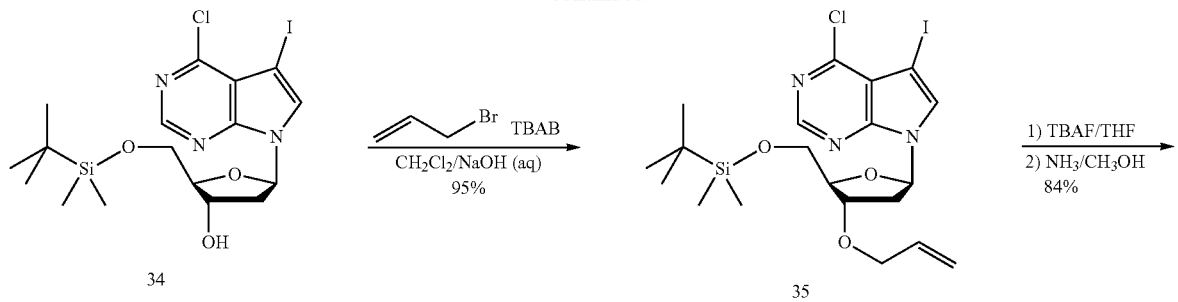
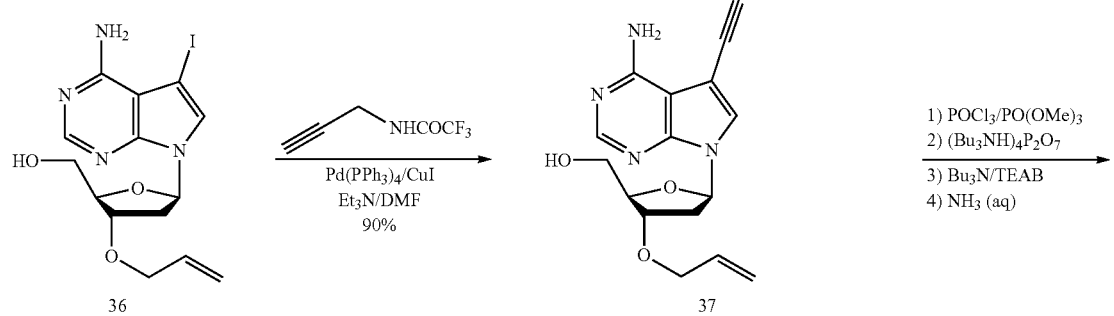
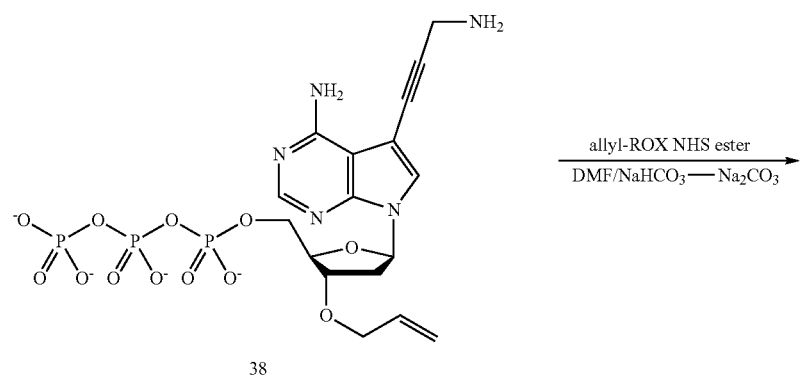
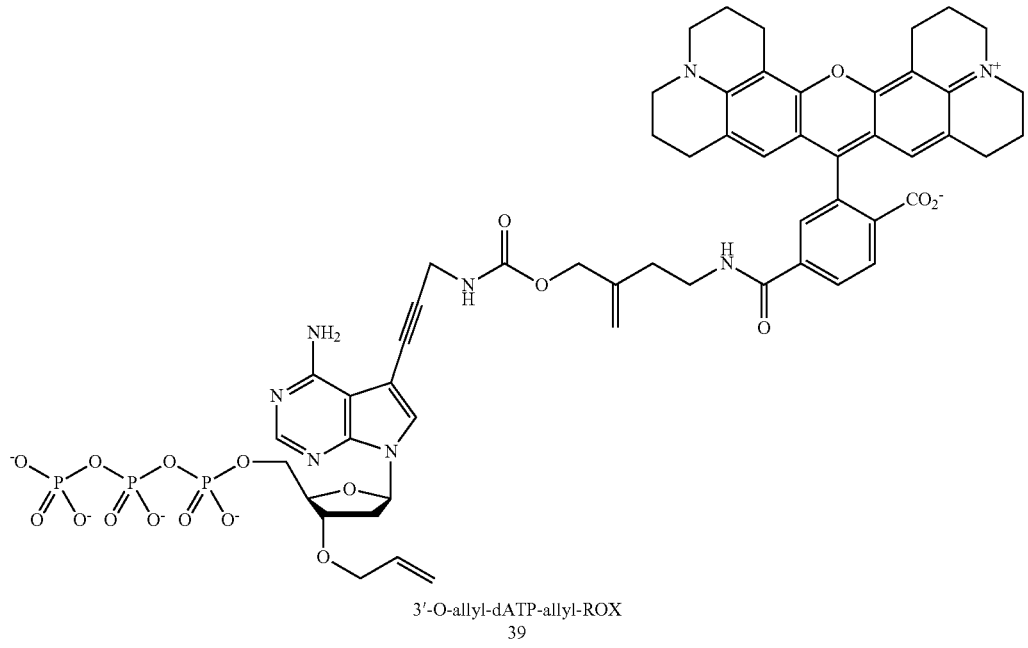
3'-O-allyl-dATP-allyl-ROX
39

6-Chloro-7-iodo-7-deazapurine (31). To a vigorously stirred solution of 30 (1.0 g; 6.51 mmol) in $CH_2Cl_2$ (55 mL), N-iodosuccimide (1.70 g; 7.18 mmol) was added. The suspension mixture was stirred at room temperature for 1 h, during which more precipitate was observed. The precipitate was filtered and then recrystallized in hot methanol to afford 31 (1.49 g; 82% yield): $^1$H NMR (400 MHz, DMSO-d6) δ 12.96 (br s, 1H, NH), 8.59 (s, 1H, 2-H), 7.94 (s, 1H, 8-H); $^{13}$C NMR (100 MHz, DMSO-d6) δ 151.2, 150.4, 150.2, 133.6, 115.5, 51.7; HRMS (FAB+) calcd for $C_6H_4N_3ClI$ (M+H$^+$): 279.9139, found: 279.9141.

6-Chloro-9-(β-D-2'-deoxyribofuranosyl)-7-iodo-7-deazapurine (33). To a stirred solution of 31 (707 mg; 2.53 mmol) in $CH_3CN$ (43 mL), KOH powder (355 mg; 6.34 mmol) and tris [2-(2-methoxyethoxy)ethyl]amine (TDA-1) (52 μL, 0.165 mmol) were added. The mixture was stirred at room temperature for 10 min and then 3,5-di-O-(p-toluyl)-2-deoxy-D-ribofuranosyl chloride 32 (1.18 g; 2.73 mmol) was added. The reaction mixture was stirred vigorously at room temperature for 1 h, and the insoluble portion was filtered and washed with hot acetone. The combined solution was evaporated and dissolved in 7M ammonia in methanol solution (86 mL). The mixture was stirred at room temperature for 24 h. After evaporation, the crude product was purified by flash column chromatography using $CH_3OH$—$CH_2Cl_2$ (0~1:20) as the eluent to afford 33 as white solid (711 mg; 71% yield): $^1$H NMR (400 MHz, $CD_3OD$) δ 8.57 (s, 1H, 2-H), 8.08 (s, 1H, 8-H), 6.72 (dd, J=6.3, 7.5 Hz, 1H, 1'-H), 4.53 (m, 1H, 3'-H), 4.00 (m, 1H, 4'-H), 3.80 (dd, J=3.6, 12.0 Hz, 1H, one of 5'-H), 3.74 (dd, J=3.6, 12.0 Hz, 1H, one of 5'-H), 2.56-2.64 (ddd, J=6.1, 7.5, 13.5 Hz, 1H, one of 2'-H), 2.36-2.43 (ddd, J=3.3, 6.2, 13.5 Hz, 1H, one of 2'-H); $^{13}$C NMR (100 MHz, $CD_3OD$) δ 152.9, 151.7, 151.3, 134.7, 118.5, 89.0, 85.7, 72.6, 63.2, 52.6, 41.7; HRMS (FAB+) calcd for $C_{11}H_{12}O_3N_3ClI$ (M+H$^+$): 395.9612, found: 395.9607.

9-[β-D-5'-O-(tert-But yldimethylsilyl)-2'-deoxyribofuranosyl]-6-chloro-7-iodo7-deazapurine (34).

The procedure was similar to the synthesis of 18, and the crude product was purified by flash column chromatography using ethyl acetate-hexane (1:3-2) as the eluent to afford 34 as white solid (597 mg; 65% yield) and 33 (213 mg; 30% yield). The above procedure was repeated with the recovered 33 to achieve a 86% overall yield of 34: $^1$H NMR (400 MHz, $CD_3OD$) δ 8.56 (s, 1H, 2-H), 7.99 (s, 1H, 8-H), 6.73 ('t', J=6.7 Hz, 1H, 1'-H), 4.52 (m, 1H, 3'-H), 4.02 (m, 1H, 4'-H), 3.92 (dd, J=3.0, 11.4 Hz, 1H, one of 5'-H), 3.86 (dd, J=3.1, 11.4 Hz, 1H, one of 5'-H), 2.47-2.55 (ddd, J=5.8, 7.1, 13.4 Hz, 1H, one of 2'-H), 2.40-2.47 (ddd, J=3.6, 6.3, 13.4 Hz, 1H, one of 2'-H), 0.94 (s, 9H, C(CH$_3$)$_3$), 0.14 (s, 3H, one of SiCH$_3$), 0.13 (s, 3H, one of SiCH$_3$); $^{13}$C NMR (100 MHz, $CD_3OD$) δ 152.8, 151.5, 151.3, 133.8, 118.2, 88.9, 85.4, 72.5, 64.6, 52.6, 42.4, 26.7, 19.5, -4.9, -5.0; HRMS (FAB+) calcd for $C_{17}H_{26}O_3N_3ClSiI$ (M+H$^+$): 510.0477, found: 510.0487.

9-[β-D-3'-O-Allyl-5'-O-(tert-butyldimethylsilyl)-2'-deoxyribofuranosyl]-6-chloro-7-iodo-7-deazapurine (35). To a stirred solution of 34 (789 mg; 1.55 mmol) in $CH_2Cl_2$ (48 mL), tetrabutylammonium bromide (TBAB) (255 mg; 0.77 mmol), allyl bromide (0.69 mL, 7.74 mmol) and 40% aqueous NaOH solution (24 mL) were added respectively. The reaction mixture was stirred at room temperature for 1 h. Ethyl acetate (150 mL) was added and the organic layer was separated. The aqueous layer was extracted with ethyl acetate (2×50 mL). The combined organic layer was washed with saturated aqueous $NaHCO_3$, NaCl, and dried over anhydrous $Na_2SO_4$. After evaporation, the residue was purified by flash column chromatography using ethyl acetate-hexane (1:6) as the eluent to afford 35 as yellow oil (809 mg; 95% yield): $^1$H NMR (400 MHz, $CD_3OD$) δ 8.52 (s, 1H, 2-H), 7.94 (s, 1H, 8-H), 6.64 (dd, J=6.1, 7.6 Hz, 1H, 1'-H), 5.88-5.99 (m, 1H, $CH_2CH=CH_2$), 5.28-5.34 (dm, J=17.3 Hz, 1H, one of $CH_2CH=CH_2$), 5.16-5.21 (dm, J=10.4 Hz, 1H, one of $CH_2CH=CH_2$), 4.28 (m, 1H, 3'-H), 4.13 (m, 1H, 4'-H), 4.01-4.11 (m, 2H, $CH_2CH=CH_2$), 3.88 (dd, J=3.6, 11.2 Hz, 1H, one of 5'-H), 3.80 (dd, J=3.1, 11.3 Hz, 1H, one of 5'-H), 2.51-2.57 (ddd, J=2.7, 6.0, 13.5 Hz, 1H, one of 2'-H), 2.42-2.50 (ddd, J=5.7, 7.7, 13.5 Hz, 1H, one of 2'-H), 0.93 (s, 9H, C(CH$_3$)$_3$), 0.13 (s, 3H, one of SiCH$_3$), 0.12 (s, 3H, one of SiCH$_3$); $^{13}$C NMR (100 MHz, $CD_3OD$) δ 152.8, 151.4, 151.3, 135.5, 133.6, 118.2, 117.2, 86.5, 85.6, 80.2, 71.0, 64.8, 52.8, 39.7, 26.7, 19.4, -4.8, -5.0; HRMS (FAB+) calcd for $C_{20}H_{30}O_3N_3ClSiI$ (M+H$^+$): 550.0790, found: 550.0773.

3'-O-Allyl-7-deaza-7-iodo-2'-deoxyadenosine (36). To a stirred solution of 35 (809 mg; 1.47 mmol) in anhydrous THF (34 mL), 1 M TBAF in THF solution (1.62 mL; 1.62 mmol) was added and the reaction was stirred at room temperature for 1 h. After evaporation, the residue was dissolved in 7M ammonia in methanol solution (24 mL). The solution was stirred in an autoclave at 115-120° C. for 15 h. After evaporation, the residue was purified by flash column chromatography using $CH_3OH$—$CH_2Cl_2$ (1:20) as the eluent to afford 36 as white solid (514 mg; 84% yield): $^1$H NMR (400 MHz, $CD_3OD$) δ 8.08 (s, 1H, 2-H), 7.56 (s, 1H, 8-H), 6.45 (dd, J=5.8, 8.6 Hz, 1H, 1'-H), 5.90-6.00 (m, 1H, $CH_2CH=CH_2$), 5.29-5.35 (dm, J=17.2 Hz, 1H, one of $CH_2CH=CH_2$), 5.16-5.21 (dm, J=10.5 Hz, 1H, one of $CH_2CH=CH_2$), 4.28 (m, 1H, 3'-H), 4.12 (m, 1H, 4'-H), 4.02-4.12 (m, 2H, $CH_2CH=CH_2$), 3.78 (dd, J=3.7, 12.1 Hz, 1H, one of 5'-H), 3.70 (dd, J=3.6, 12.1 Hz, 1H, one of 5'-H), 2.53-2.61 (ddd, J=5.8, 8.6, 13.6 Hz, 1H, one of 2'-H), 2.41-2.47 (ddd, J=2.0, 5.8, 13.5 Hz, 1H, one of 2'-H); $^{13}$C NMR (100 MHz, $CD_3OD$) δ 158.5, 152.3, 150.3, 135.7, 128.8, 117.0, 105.3, 86.8, 86.4, 80.7, 71.0, 63.7, 51.3, 38.8; HRMS (FAB+) calcd for $C_{14}H_{18}O_3N_4I$ (M+H$^+$): 417.0424, found: 417.0438.

3'-O-Allyl-7-deaza-7-(3-[(trifluoroacetyl)amino]prop-1-ynyl)-2'-deoxyadenosine (37). The procedure was similar to the synthesis of 21, and the crude product was purified by flash column chromatography using ethyl acetate-hexane (1:1~0) as the eluent to afford 37 as yellow solid (486 mg; 90% yield): $^1$H NMR (400 MHz, $CD_3OD$) δ 8.08 (s, 1H, 2-H), 7.60 (s, 1H, 8-H), 6.41 (dd, J=5.8, 8.6 Hz, 1H, 1'-H), 5.89-6.00 (m, 1H, $CH_2CH=CH_2$), 5.29-5.35 (dm, J=17.3 Hz, 1H, one of $CH_2CH=CH_2$), 5.16-5.21 (dm, J=10.4 Hz, 1H, one of $CH_2CH=CH_2$), 4.31 (s, 2H, C≡CCH$_2$), 4.29 (m, 1H, 3'-H), 4.13 (m, 1H, 4'-H), 4.01-4.11 (m, 2H, $CH_2CH=CH_2$), 3.79 (dd, J=3.6, 12.1 Hz, 1H, one of 5'-H), 3.71 (dd, J=3.5, 12.1 Hz, 1H, one of 5'-H), 2.54-2.62 (ddd, J=5.8, 8.6, 13.6 Hz, 1H, one of 2'-H), 2.42-2.48 (ddd, J=1.9, 5.8, 13.6 Hz, 1H, one of 2'-H); $^{13}$C NMR (100 MHz, $CD_3OD$) δ 158.8, 158.6 (q, J=38 Hz, COCF$_3$), 152.9, 149.6, 135.6, 128.1, 117.1 (q, J=284 Hz, COCF$_3$), 117.0, 104.5, 96.3, 87.3, 86.9, 86.8, 80.7, 77.0, 71.0, 63.8, 38.7, 31.1; HRMS (FAB+) calcd for $C_{19}H_{21}O_4N_5F_3$ (M+H$^+$): 440.1546, found: 440.1544.

3'-O-Allyl-7-(3-aminoprop-1-ynyl)-7-deaza-2'-deoxyadenosine-5'-triphosphate (38). The procedure was similar to the synthesis of 22 to yield 38 as colorless syrup: $^1$H NMR (300 MHz, $D_2O$) δ 8.02 (s, 1H, 2-H), 7.89 (s, 1H, 8-H), 6.54 (t, J=6.6 Hz, 1H, 1'-H), 5.89-6.02 (m, 1H, $CH_2CH=CH_2$), 5.30-5.39 (dm, J=17.3 Hz, 1H, one of CH$_2$CH=CH$_2$), 5.20-5.27 (dm, J=10.4 Hz, 1H, one of CH$_2$CH=CH$_2$), 4.48 (s, 2H, C≡CCH$_2$), 4.35 (m, 1H, 3'-H), 4.05-4.17 (m, 4H, CH$_2$CH=CH$_2$ and 5'-H), 3.99 (m, 1H, 4'-H), 2.50-2.59 (m, 2H, 2'-H); $^{31}$P NMR (121.4 MHz, D$_2$O) δ −6.1 (d, J=21.1 Hz, 1P, γ-P), −10.8 (d, J=18.8 Hz, 1P, α-P), −21.9 (t, J=19.9 Hz, 1P, β-P).

Figure 10:
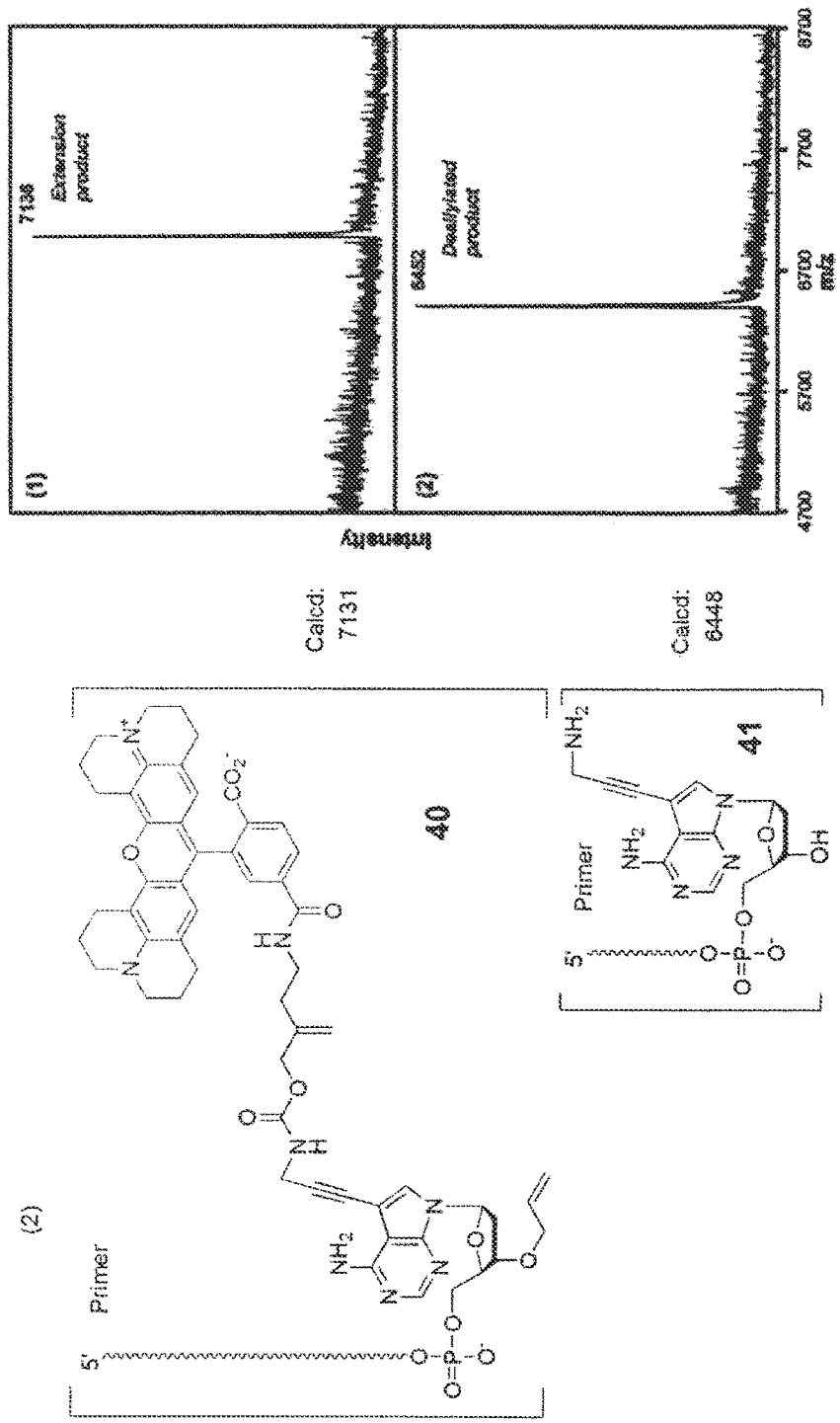
FIG. 10. Single base extension reaction and MALDI-TOF MS of 3'-O-Allyl-dATP-allyl-ROX (39).

3'-O-Allyl-dATP-allyl-ROX (39). The procedure was similar to the synthesis of 23. The product was characterized by single base extension reaction and MALDI-TOF MS. See FIG. 10.

7. Synthesis of 3'-O-allyl-dGTP-allyl-Bodipy-650 (43) and 3'-O-allyl-dGTP-allyl-Cy5 (44)

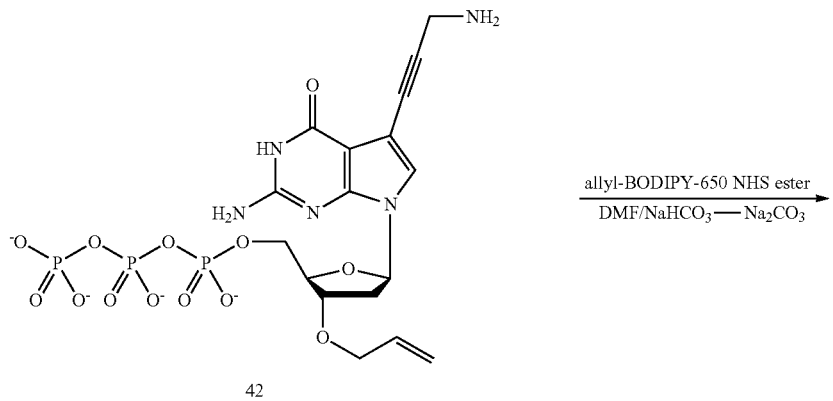

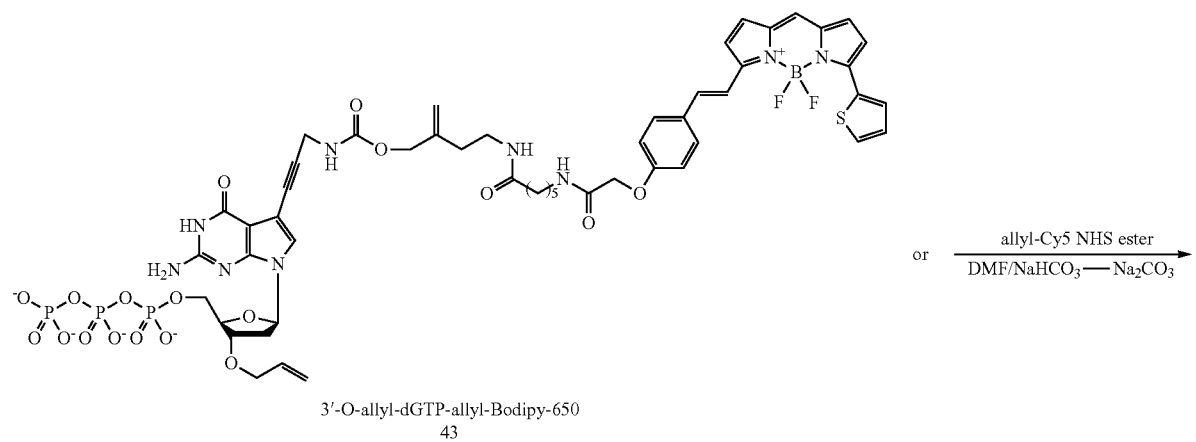

3'-O-allyl-dGTP-allyl-Bodipy-650
43

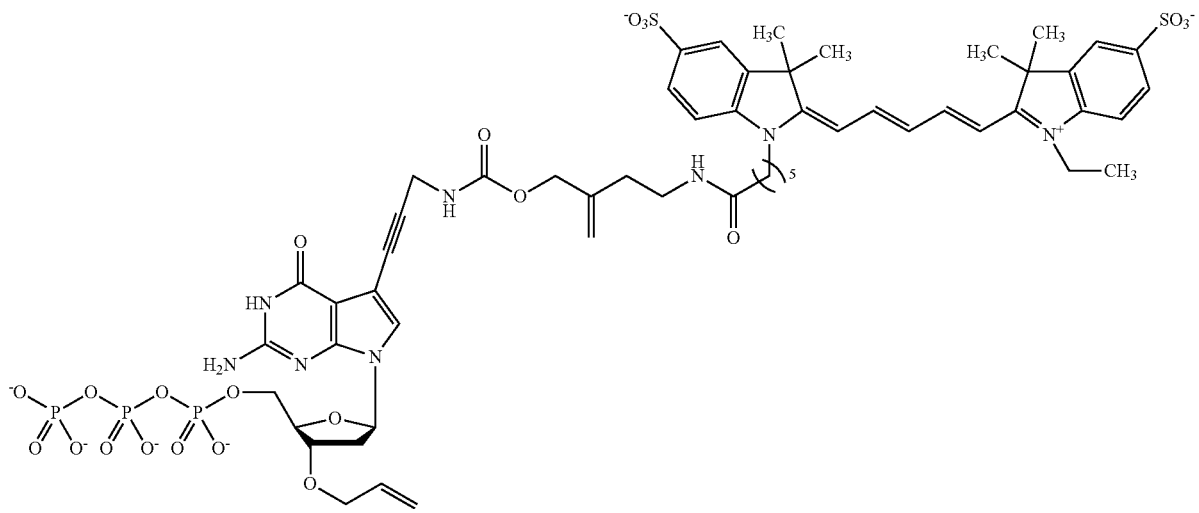

3'-O-allyl-dGTP-allyl-Cy5
44

Synthesis of 3'-O-allyl-dGTP-NH$_2$ 42 was performed according to the procedures in reference (29).

Figure 11:
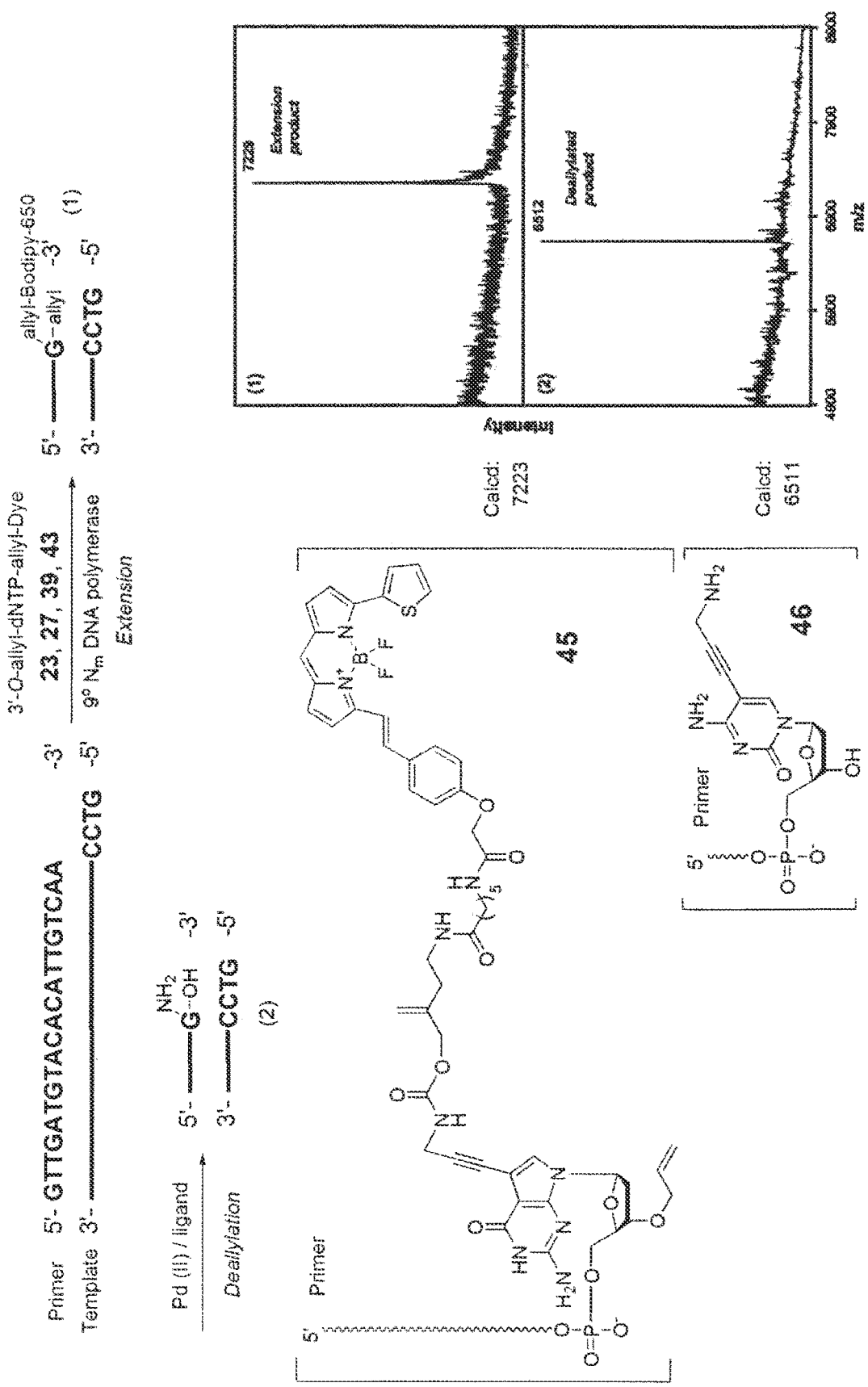
FIG. 11. Single base extension reaction and MALDI-TOF MS of 3'-O-Allyl-dGTP-allyl-Bodipy-650 (43) and 3'-O-allyl-dGTP-allyl-Cy5 (44).
Figure 12:
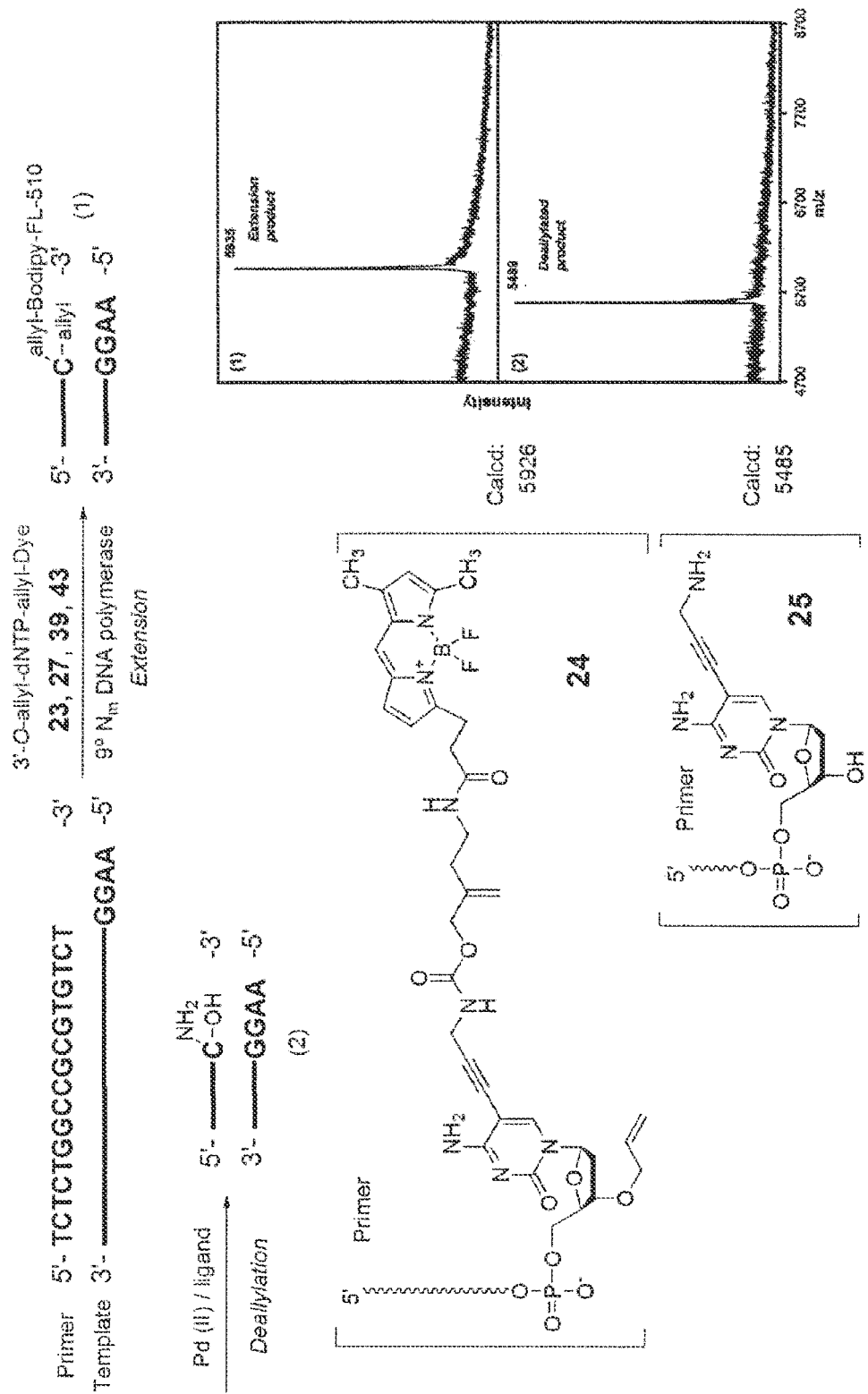
FIG. 12. Single base extension reaction and MALDI-TOF MS of 3'-O-Allyl-dCTP-allyl-Bodipy-FL-510 (23).

3'-O-Allyl-dGTP-allyl-Bodipy-650 (43) and 3'-O-allyl-dGTP-allyl-Cy5 (44). The procedures were similar to the synthesis of 23. The product was characterized by single base extension reaction and MALDI-TOF MS. See FIG. 11.

II. Synthesis of 3'-O-allyl-dNTPs

1. Synthesis of 3'-O-allyl dCTP (51)

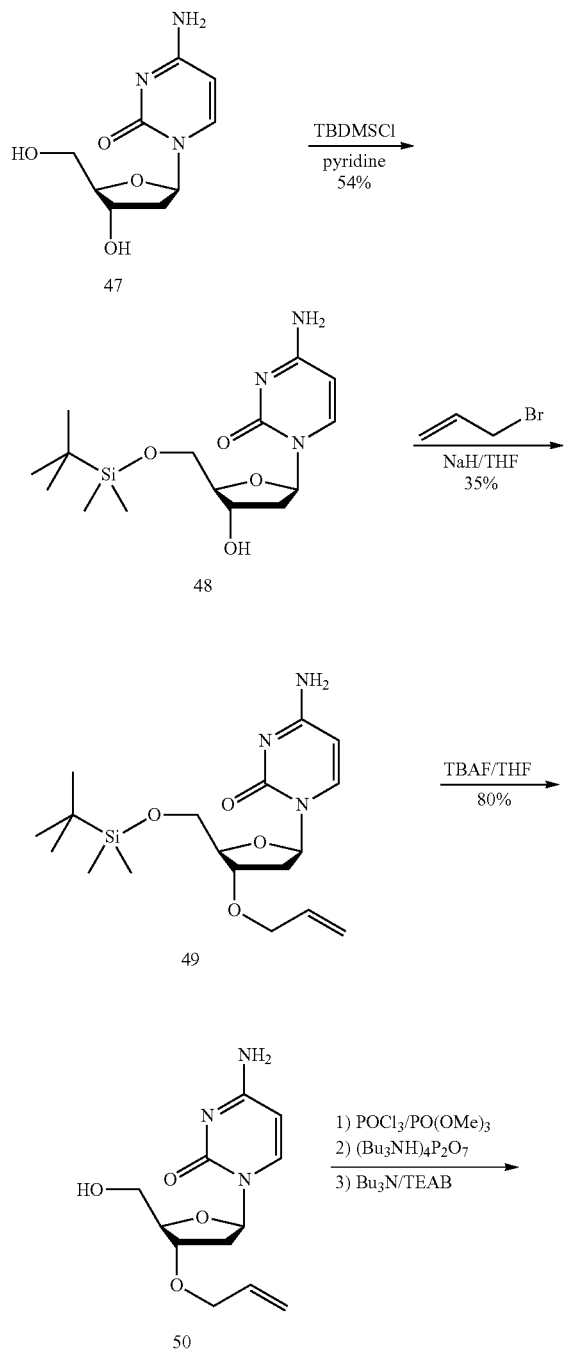

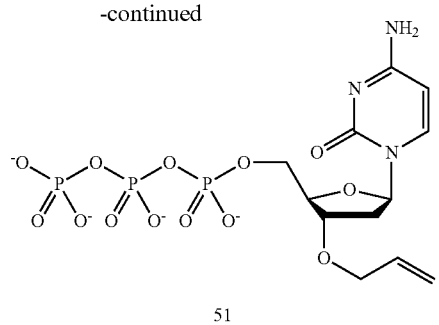

51

5'-O-(tert-Butyldimethylsilyl)-2'-deoxycytidine (48). To a stirred solution of 2'-deoxycytidine 47 (1.00 g; 4.40 mmol) in dry pyridine (37 mL), TBDMSCl (814 mg; 5.39 mmol) was added. The mixture was stirred at room temperature for 20 h. After evaporation, the residue was purified by flash column chromatography using CH$_3$OH—CH$_2$Cl$_2$ (1:10) as the eluent to afford 48 as white solid (1.26 g; 84% yield): $^1$H NMR (400 MHz, CD$_3$OD) δ 8.03 (d, J=7.5 Hz, 1H, 6-H), 6.23 (t, J=6.3 Hz, 1H, 1'-H), 5.86 (d, J=7.5 Hz, 1H, 5-H), 4.35 (in, 1H, 3'-H), 3.91-3.98 (m, 2H, 4'-H and one of 5'-H), 3.85 (dd, J=2.5, 11.3 Hz, 1H, one of 5'-H), 2.36-2.43 (ddd, J=4.1, 6.1, 13.5 Hz, 1H, one of 2'-H), 2.05-2.13 (m, 1H, one of 2'-H), 0.94 (s, 9H, C(CH$_3$)$_3$), 0.14 (s, 3H, one of SiCH$_2$), 0.13 (s, 3H, one of SiCH$_3$); $^{13}$C NMR (100 MHz, CD$_3$OD) δ 167.1, 157.6, 142.1, 95.6, 88.7, 87.4, 71.7, 64.1, 42.7, 26.5, 19.3, −5.2, −5.3; HRMS (FAB+) calcd for C$_{15}$H$_{28}$O$_4$N$_3$Si (M+H$^+$): 342.1849, found: 342.1844.

3'-O-Allyl-5'-O-(tert-butyldimethylsilyl)-2'-deoxycytidine (49). The procedure was similar to the synthesis of 19 and the crude product was purified by flash column chromatography using CH$_3$OH—CH$_2$Cl$_2$ (1:20) as the eluent to afford 49 as yellow solid (480 mg; 35% yield): $^1$H NMR (400 MHz, CD$_3$OD) δ 7.97 (d, J=7.5 Hz, 1H, 6-H), 6.21 (t, J=6.5 Hz, 1H, 1'-H), 5.87 (d, J=7.5 Hz, 1H, 5-H), 5.87-5.97 (m, 1H, CH$_2$CH═CH$_2$), 5.26-5.33 (dm, J=17.2 Hz, 1H, one of CH$_2$CH═CH$_2$), 5.15-5.20 (dm, J=10.5 Hz, 1H, one of CH$_2$CH═CH$_2$), 4.16 (m, 1H, 3'-H), 4.11 (m, 1H, 4'-H), 3.97-4.11 (m, 2H, CH$_2$CH═CH$_2$), 3.92 (dd, J=3.2, 11.4 Hz, 1H, one of 5'-H), 3.84 (dd, J=2.8, 11.4 Hz, 1H, one of 5'-H), 2.46-2.51 (ddd, J=3.1, 5.9, 13.6 Hz, 1H, one of 2'-H), 2.00-2.08 (m, 1H, one of 2'-H), 0.94 (s, 9H, C(CH$_3$)$_3$), 0.13 (s, 6H, Si(CH$_3$)$_2$); $^{13}$C NMR (100 MHz, CD$_3$OD) δ 167.2, 157.7, 141.9, 135.6, 117.1, 95.7, 87.5, 86.6, 79.7, 71.1, 64.4, 39.8, 26.5, 19.3, −5.1, −5.2; HRMS (FAB+) calcd for C$_{15}$H$_{28}$O$_4$N$_3$Si (M+H$^+$): 342.1849, found: 342.1844.

3'-O-Allyl-2'-deoxycytidine (50). The procedure was similar to the synthesis of 20 and the crude product was purified by flash column chromatography using CH$_3$OH-THF (1:12) and CH$_3$OH-ethyl acetate (1:4) as the eluent to afford 50 as white foam (269 mg; 80% yield): $^1$H NMR (400 MHz, CD$_3$OD) δ 7.96 (d, J=7.5 Hz, 1H, 6-H), 6.21 (dd, J=5.9, 7.6 Hz, 1H, 1'-H), 5.89 (d, J=7.5 Hz, 1H, 5-H), 5.87-5.98 (m, 1H, CH$_2$CH═CH$_2$), 5.27-5.33 (dm, J=17.3 Hz, 1H, one of CH$_2$CH═CH$_2$), 5.15-5.19 (dm, J=10.4 Hz, 1H, one of CH$_2$CH═CH$_2$), 4.17 (m, 1H, 3'-H), 3.98-4.10 (m, 3H, 4'-H and CH$_2$CH═CH$_2$), 3.77 (dd, J=3.6, 12.0 Hz, 1H, one of 5'-H), 3.71 (dd, J=3.7, 12.0 Hz, 1H, one of 5'-H), 2.43-2.50 (ddd, J=2.7, 5.9, 13.6 Hz, 1H, one of 2'-H), 2.03-2.11 (ddd, J=6.2, 7.7, 13.6 Hz, 1H, one of 2'-H); $^{13}$C NMR (100 MHz, CD$_3$OD) δ 167.1, 157.7, 142.2, 135.5, 117.0, 96.0, 87.5, 86.6, 80.0, 71.0, 63.0, 39.1; HRMS (FAB+) calcd for C$_{12}$H$_{18}$O$_4$N$_3$ (M+H$^+$): 268.1297, found: 268.1307.

3'-O-Allyl-2'-deoxycytidine-5'-triphosphate (51). 50 (86 mg; 0.32 mmol) and proton sponge (84 mg; 0.39 mmol) were dried in a vacuum desiccator over $P_2O_5$ overnight before dissolving in trimethylphosphate (0.60 mL).

Freshly distilled $POCl_3$ (35.8 μL; 0.383 mmol) was added dropwise at 0° C. and the mixture was stirred for 3 h. Then the solution of tributylammonium pyrophosphate (607 mg) and tributylamine (0.61 mL; 2.56 mmol) in anhydrous DMF (2.6 mL) was well vortexed and added in one portion at room temperature and the reaction was stirred for 30 min. After that triethylammonium bicarbonate solution (TEAB) (0.1 M; 16 mL) was added and the mixture was stirred for 2 h. After most liquid was removed under vacuum, the residue was redissolved in water (2 mL) and filtered. The aqueous solution was purified by DEAE Sephadex A25 ion exchange column using gradient aqueous TEAB solution (from 0.1 M to 1.0 M) as eluent to afford 51 as colorless syrup after evaporation: $^1$H NMR (300 MHz, $D_2O$) δ 7.90 (d, J=7.4 Hz, 1H, 6-H), 6.20 (dd, J=5.9, 7.6 Hz, 1H, 1'-H), 5.92 (d, J=7.4 Hz, 1H, 5-H), 5.85-5.97 (m, 1H, $CH_2CH\!=\!CH_2$), 5.25-5.34 (m, 1H, one of $CH_2CH\!=\!CH_2$), 5.15-5.20 (m, 1H, one of $CH_2CH\!=\!CH_2$), 4.15 (m, 1H, 3'-H), 3.96-4.10 (m, 3H, 4'-H and $CH_2CH\!=\!CH_2$), 3.70-3.80 (m, 2H, 5'-H), 2.43-2.52 (m, 1H, one of 2'-H), 2.05-2.14 (m, 1H, one of 2'-H); $^{31}$P NMR (121.4 MHz, $D_2O$) δ −8.8 (d, J=19.0 Hz, 1P, γ-P), −11.3 (d, J=19.6 Hz, 1P, α-P), −22.9 (t, J=19.5 Hz, 1P, β-P).

2. Synthesis of 3'-O-allyl-dTTP (53)

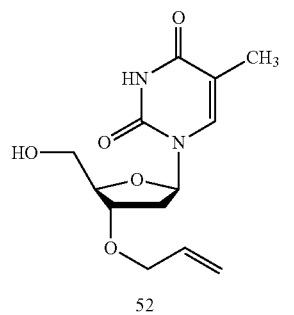

52

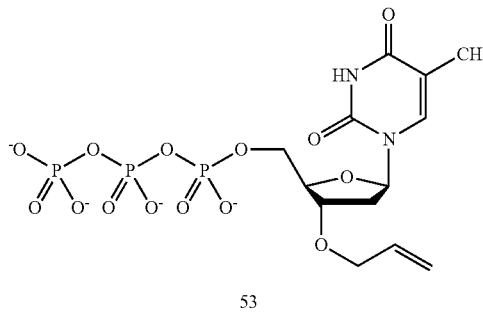

53

Synthesis of 3'-O-allylthymidine 52 was performed according to the procedures in reference (28).

3'-O-Allylthymidine-5'-triphosphate (53). The procedure was similar to the synthesis of 51 to yield 53 as colorless syrup: $^1$H NMR (300 MHz, $D_2O$) δ 7.80 (m, 1H, 6-H), 6.23 (dd, J=6.2, 8.1 Hz, 1H, 1'-H), 5.85-5.97 (m, 1H, $CH_2CH\!=\!CH_2$), 5.25-5.32 (m, 1H, one of $CH_2CH\!=\!CH_2$), 5.15-5.21 (m, 1H, one of $CH_2CH\!=\!CH_2$), 4.17 (m, 1H, 3'-H), 3.97-4.11 (m, 3H, 4'-H and $CH_2CH\!=\!CH_2$), 3.70-3.80 (m, 2H, 5'-H), 2.30-2.41 (m, 1H, one of 2'-H), 2.11-2.23 (m, 1H, one of 2'-H), 1.86 (d, J=1.2 Hz, 3H, $CH_3$); $^{31}$P NMR (121.4 MHz, $D_2O$) δ −7.1 (d, J=20.1 Hz, 1P, γ-P), −10.8 (d, J=19.5 Hz, 1P, α-P), −21.8 (t, J=19.5 Hz, 1P, β-P).

3. Synthesis of 3'-O-allyl-dATP (59)

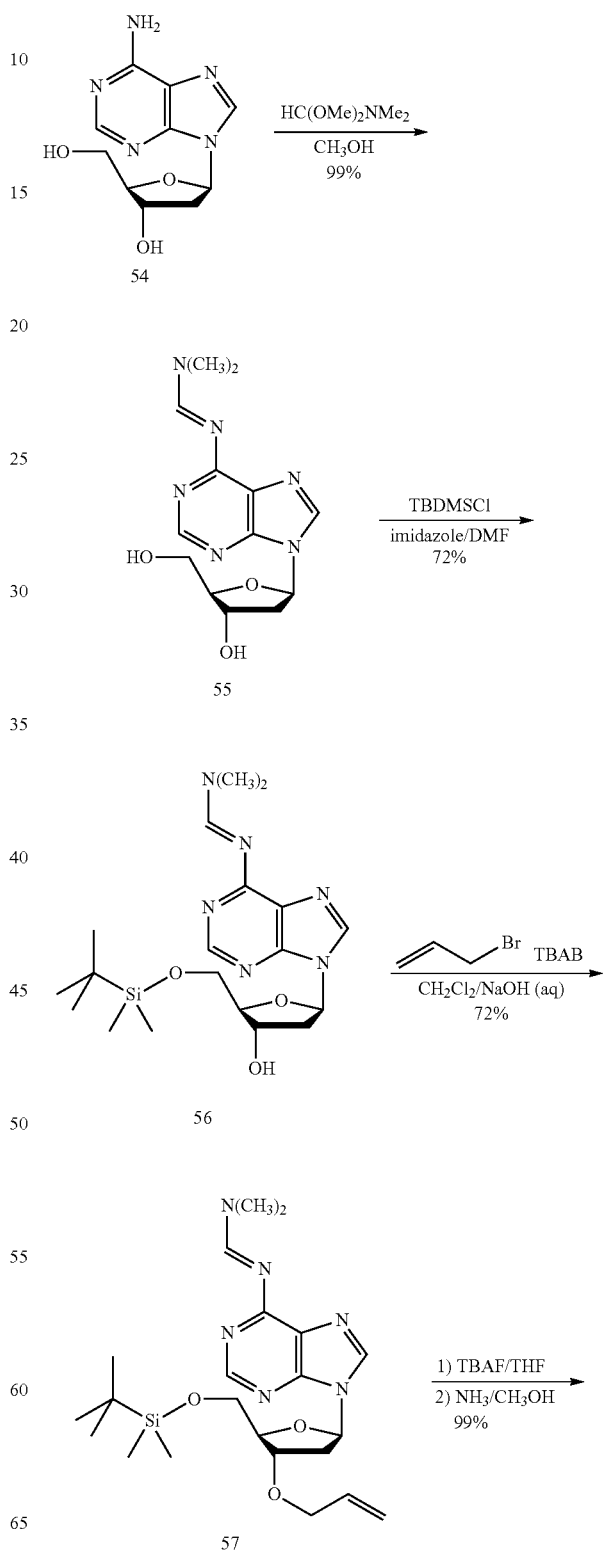

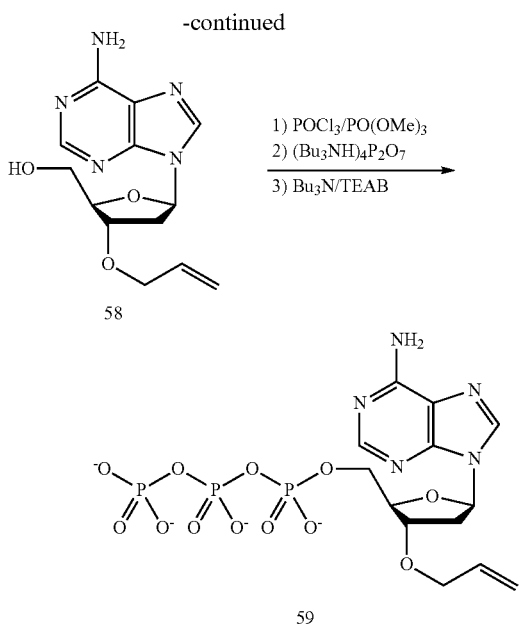

N6-[(Dimethylamino)methylene]-2'-deoxyadenosine (55).

To a stirred solution of 2'-deoxyadenosine monohydrate 54 (1.00 g; 3.71 mmol) in methanol (43 mL), N,N-dimethylformamide dimethyl acetal (2.48 mL; 18.6 mmol) was added. The reaction was stirred at 50° C. for 16 h. After evaporation, $CH_2Cl_2$-hexane (1:1) was added. The white solid formed was then filtered, collected and washed by hexane to afford 55 as white solid (1.13 g; 99% yield): $^1$H NMR (400 MHz, $CD_3OD$) δ 8.92 (s, 1H, $CHN(CH_3)_2$), 8.44 (s, 1H, 2-H), 8.43 (s, 1H, 8-H), 6.48 (dd, J=6.2, 7.8 Hz, 1H, 1'-H), 4.59 (m, 1H, 3'-H), 4.07 (m, 1H, 4'-H), 3.86 (dd, J=3.1, 12.2 Hz, 1H, one of 5'-H), 3.76 (dd, J=3.5, 12.2 Hz, 1H, one of 5'-H), 3.25 (s, 3H, one of $NCH_3$), 3.24 (s, 3H, one of $NCH_3$), 2.80-2.88 (ddd, J=5.9, 7.8, 13.5 Hz, 1H, one of 2'-H), 2.40-2.47 (ddd, J=2.8, 6.1, 13.4 Hz, 1H, one of 2'-H); $^{13}$C NMR (100 MHz, $CD_3OD$) δ 161.0, 159.9, 152.8, 151.1, 142.8, 127.0, 89.7, 86.9, 72.9, 63.5, 41.5 ($N(CH_3)_2$), 35.3; HRMS (FAB+) calcd for $C_{13}H_{19}O_3N_6$ (M+H+): 307.1519, found: 307.1511.

5'-O-(tert-Butyldimethylsilyl)-N6-[(dimethylamino)methylene]-2'-deoxyadenosine (56). The procedure was similar to the synthesis of 18, and the crude product was purified by flash column chromatography using $CH_3OH$—$CH_2Cl_2$ (1:20) as the eluent to afford 56 as white foam (1.11 g; 72% yield): $^1$H NMR (400 MHz, $CD_3OD$) δ 8.90 (s, 1H, $CHN(CH_3)_2$), 8.45 (s, 1H, 2-H), 8.43 (s, 1H, 8-H), 6.49 (t, J=6.5 Hz, 1H, 1'-H), 4.59 (m, 1H, 3'-H), 4.04 (m, 1H, 4'-H), 3.95 (dd, J=3.7, 11.3 Hz, 1H, one of 5'-H), 3.85 (dd, J=2.8, 11.3 Hz, 1H, one of 5'-H), 3.25 (s, 3H, one of $NCH_3$), 3.24 (s, 3H, one of $NCH_3$), 2.73-2.81 (m, 1H, one of 2'-H), 2.48-2.55 (ddd, J=4.0, 6.4, 13.5 Hz, 1H, one of 2'-H), 0.90 (s, 9H, $C(CH_3)_3$), 0.08 (s, 3H, one of $SiCH_3$), 0.07 (s, 3H, one of $SiCH_3$); $^{13}$C NMR (100 MHz, $CD_3OD$) δ 160.6, 159.7, 153.0, 151.7, 141.8, 126.5, 88.9, 85.7, 72.1, 64.3, 41.6, 41.5, 35.3, 26.5, 19.3, −5.0, −5.1; HRMS (FAB+) calcd for $C_{19}H_{33}O_3N_6Si$ (M+H+): 421.2383, found: 421.2390.

3'-O-Allyl-5'-O-(t-butyldimethylsilyl)-N6-[(dimethylamino)methylene]-2'-deoxyadenosine (57). The procedure was similar to the synthesis of 35, and the crude product was purified by flash column chromatography using $CH_3OH$—$CH_2Cl_2$ (1:25) and $CH_3OH$-ethyl acetate (1:10) as the eluent to afford 57 as colorless oil (875 mg; 72% yield): $^1$H NMR (400 MHz, $CD_3OD$) δ 8.90 (s, 1H, $CHN(CH_3)_2$), 8.44 (s, 1H, 2-H), 8.41 (s, 1H, 8-H), 6.45 (dd, J=6.3, 7.2 Hz, 1H, 1'-H), 5.91-6.01 (m, 1H, $CH_2CH=CH_2$), 5.30-5.37 (dm, J=17.2 Hz, 1H, one of $CH_2CH=CH_2$), 5.18-5.22 (dm, J=10.5 Hz, 1H, one of $CH_2CH=CH_2$), 4.37 (m, 1H, 3'-H), 4.17 (m, 1H, 4'-H), 4.05-4.15 (m, 2H, $CH_2CH=CH_2$), 3.91 (dd, J=4.6, 11.1 Hz, 1H, one of 5'-H), 3.83 (dd, J=3.8, 11.1 Hz, 1H, one of 5'-H), 3.25 (s, 3H, one of $NCH_3$), 3.24 (s, 3H, one of $NCH_3$), 2.76-2.83 (ddd, J=6.0, 7.3, 13.6 Hz, 1H, one of 2'-H), 2.59-2.65 (ddd, J=3.0, 6.1, 13.6 Hz, 1H, one of 2'-H), 0.90 (s, 9H, $C(CH_3)_3$), 0.08 (s, 6H, $Si(CH_3)_2$); $^{13}$C NMR (100 MHz, $CD_3OD$) δ 160.7, 159.7, 153.1, 151.8, 141.9, 135.6, 126.5, 117.1, 86.7, 85.9, 80.1, 71.1, 64.5, 41.5, 38.7, 35.3, 26.5, 19.3, −5.0, −5.1; HRMS (FAB+) calcd for $C_{22}H_{37}O_3N_6Si$ (M+H+): 461.2696, found: 461.2695.

3'-O-Allyl-2'-deoxyadenosine (58). To a stirred solution of 57 (875 mg; 1.90 mmol) in anhydrous THF (45 mL), 1 M TBAF in THF solution (2.09 mL; 2.09 mmol) was added and the reaction was stirred at room temperature for 1 h. After evaporation, the residue was dissolved in 7 M ammonia in methanol solution (34 mL). The mixture was then stirred in a sealed flask at 50° C. for 9 h. After evaporation, the residue was purified by flash column chromatography using $CH_3OH$—$CH_2Cl_2$ (1:10) as the eluent to afford 58 as white solid (548 mg; 99% yield): $^1$H NMR (400 MHz, $CD_3OD$) δ 8.30 (s, 1H, 2-H), 8.17 (s, 1H, 8-H), 6.38 (dd, J=5.8, 8.6 Hz, 1H, 1'-H), 5.91-6.01 (m, 1H, $CH_2CH=CH_2$), 5.30-5.37 (dm, J=17.3 Hz, 1H, one of $CH_2CH=CH_2$), 5.17-5.22 (dm, J=10.6 Hz, 1H, one of $CH_2CH=CH_2$), 4.36 (m, 1H, 3'-H), 4.21 (m, 1H, 4'-H), 4.04-4.15 (m, 2H, $CH_2CH=CH_2$), 3.85 (dd, J=3.2, 12.3 Hz, 1H, one of 5'-H), 3.74 (dd, J=3.2, 12.3 Hz, 1H, one of 5'-H), 2.75-2.83 (ddd, J=5.7, 8.6, 13.6 Hz, 1H, one of 2'-H), 2.52-2.58 (ddd, J=1.8, 5.8, 13.6 Hz, 1H, one of 2'-H); $^{13}$C NMR (100 MHz, $CD_3OD$) δ 157.1, 153.1, 149.5, 141.2, 135.6, 120.6, 117.0, 87.5, 87.2, 80.9, 71.0, 63.9, 38.7; HRMS (FAB+) calcd for $C_{13}H_{18}O_3N_5$ (M+H+): 292.1410, found: 292.1426.

3'-O-Allyl-2'-deoxyadenosine-5'-triphosphate (59). The procedure was similar to the synthesis of 51 to yield 59 as colorless syrup: $^1$H NMR (300 MHz, $D_2O$) δ 8.46 (s, 1H, 2-H), 8.19 (s, 1H, 8-H), 6.43 (dd, J=6.3, 7.2 Hz, 1H, 1'-H), 5.90-6.02 (m, 1H, $CH_2CH=CH_2$), 5.31-5.40 (dm, J=17.1 Hz, 1H, one of $CH_2CH=CH_2$), 5.21-5.28 (dm, J=10.8 Hz, 1H, one of $CH_2CH=CH_2$), 4.55 (m, 1H, 3'-H), 4.40 (m, 1H, 4'-H), 4.06-4.20 (m, 4H, $CH_2CH=CH_2$ and 5'-H), 2.61-2.82 (m, 2H, 2'-H); $^{31}$P NMR (121.4 MHz, $D_2O$) δ −8.9 (d, J=19.1 Hz, 1P, γ-P), −11.2 (d, J=19.7 Hz, 1P, α-P), −22.8 (t, J=19.9 Hz, 1P, β-P).

4. Synthesis of 3'-O-allyl-dGTP (65)

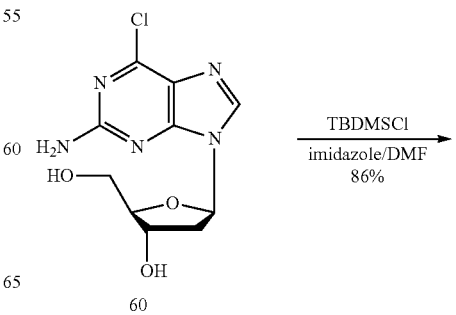

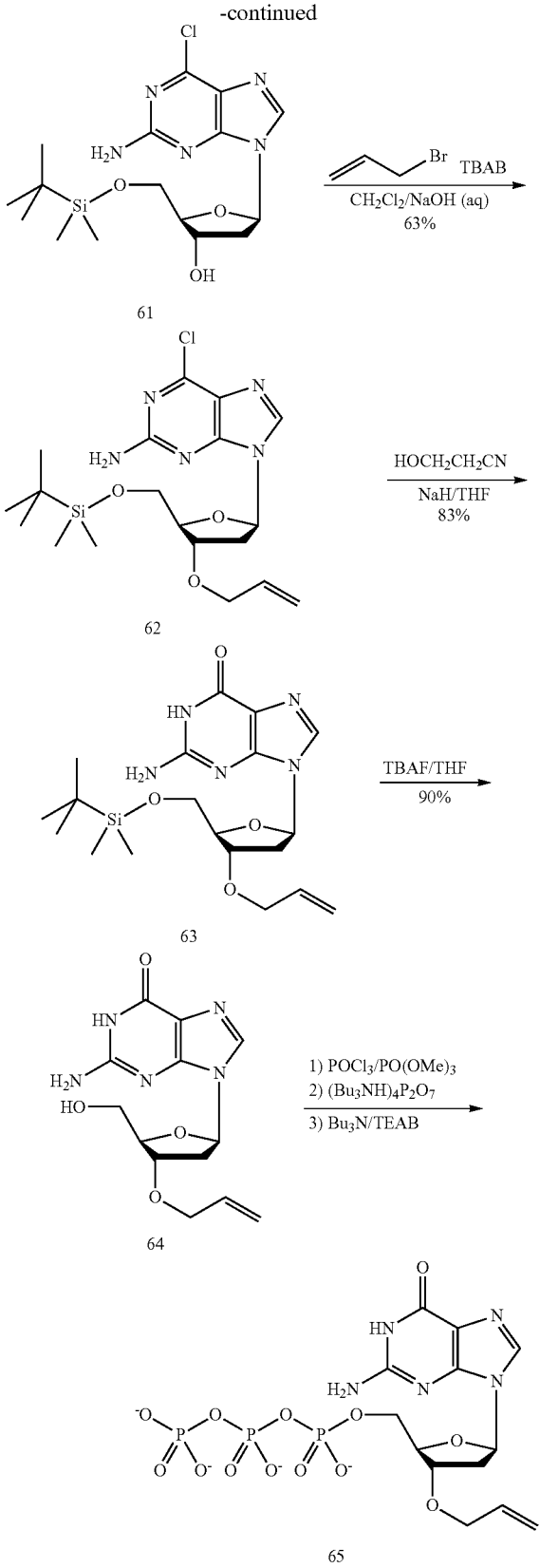

by flash column chromatography using CH₃OH—CH₂Cl₂ (1:20) as the eluent to afford 61 as white solid (1.20 g; 86% yield): ¹H NMR (400 MHz, CD₃OD) δ 8.25 (s, 1H, 8-H), 6.34 (t, J=6.4 Hz, 1H, 1'-H), 4.56 (m, 1H, 3'-H), 4.01 (m, 1H, 4'-H), 3.90 (dd, J=3.5, 11.4 Hz, 1H, one of 5'-H), 3.84 (dd, J=3.8, 11.4 Hz, 1H, one of 5'-H), 2.67-2.74 (m, 1H, one of 2'-H), 2.43-2.50 (ddd, J=4.2, 6.4, 13.5 Hz, 1H, one of 2'-H), 0.89 (s, 9H, C(CH₃)₃), 0.07 (s, 3H, one of SiCH₃), 0.06 (s, 3H, one of SiCH₃); ¹³C NMR (100 MHz, CD₃OD) δ 161.1, 154.2, 151.2, 142.0, 124.9, 88.9, 85.5, 72.0, 64.3, 41.4, 26.5, 19.3, −5.1 (two SiCH); HRMS (FAB+) calcd for C₁₆H₂₇O₃N₅ClSi (M+H⁺): 400.1572, found: 400.1561.

2-Amino-6-chloro-9-[β-D-3'-O-allyl-5'-O-(tert-butyldimethylsilyl)-2'-deoxyribo-furanosyl]-purine (62). The procedure was the same as that of 35, and the crude product 61 converted from 60 was purified by flash column chromatography using ethyl acetate-hexane (1:2) as the eluent to afford 62 as white solid (832 mg; 63% yield): ¹H NMR (400 MHz, CD₃OD) δ 8.23 (s, 1H, 8-H), 6.30 (t, J=6.7 Hz, 1H, 1'-H), 5.89-5.99 (m, 1H, CH₂CH=CH₂), 5.28-5.35 (dm, J=17.3 Hz, 1H, one of CH₂CH=CH₂), 5.16-5.21 (dm, J=10.5 Hz, 1H, one of CH₂CH=CH₂), 4.33 (m, 1H, 3'-H), 4.13 (m, 1H, 4'-H), 4.03-4.12 (m, 2H, CH₂CH=CH₂), 3.86 (dd, J=4.3, 11.2 Hz, 1H, one of 5'-H), 3.81 (dd, J=3.9, 11.2 Hz, 1H, one of 5'-H), 2.68-2.75 (m, 1H, one of 2'-H), 2.53-2.59 (ddd, J=3.2, 6.2, 13.6 Hz, 1H, one of 2'-H), 0.88 (s, 9H, C(CH₃)₃), 0.08 (s, 3H, one of SiCH₃), 0.07 (s, 3H, one of SiCH₃); ¹³C NMR (100 MHz, CD₃OD) δ 161.1, 154.2, 151.2, 141.9, 135.5, 124.9, 117.1, 86.7, 85.6, 80.0, 71.1, 64.5, 38.7, 26.5, 19.3, −5.1, −5.2; HRMS (FAB+) calcd for C₁₉H₃₁O₃N₅ClSi (M+H⁺): 440.1885, found: 440.1870.

3'-O-Allyl-5'-O-(tert-butyldimethylsilyl)-2'-deoxyguanosine (63). To a stirred suspension of 95% NaH power (223 mg; 8.83 mmol) in anhydrous THF (82 mL), 3-hydroxypropionitrile (550 μL; 8.00 mmol) was added and the mixture was stirred at room temperature for 20 min. Then 62 (832 mg; 1.89 mmol) in anhydrous THF (20 mL) was added and the mixture was stirred at 40° C. for 1 h. At room temperature, 80% acetic acid (630 μL; 8.83 mmol) was added and stirred for 20 min. After evaporation, ethyl acetate (100 mL) was added. The mixture was washed by saturated aqueous NaHCO₃, NaCl, and dried over anhydrous Na₂SO₄. After evaporation, the residue was purified by flash column chromatography using CH₃OH—CH₂Cl₂ (1:20) as the eluent to afford 63 as white solid (661 mg; 83% yield): ¹H NMR (400 MHz, CD₃OD) δ 7.92 (s, 1H, 8-H), 6.22 (dd, J=6.4, 7.3 Hz, 1H, 1'-H), 5.89-5.99 (m, 1H, CH₂CH=CH₂), 5.29-5.35 (dm, J=17.3 Hz, 1H, one of CH₂CH=CH₂), 5.17-5.21 (dm, J=10.5 Hz, 1H, one of CH₂CH=CH₂), 4.30 (m, 1H, 3'-H), 4.11 (m, 1H, 4'-H), 4.03-4.12 (m, 2H, CH₂CH=CH₂), 3.79-3.86 (m, 2H, 5'-H), 2.56-2.64 (ddd, J=5.9, 7.4, 13.5 Hz, 1H, one of 2'-H), 2.49-2.55 (ddd, J=3.0, 6.1, 13.5 Hz, 1H, one of 2'-H), 0.91 (s, 9H, C(CH₃)₃), 0.10 (s, 3H, one of SiCH₃), 0.09 (s, 3H, one of SiCH₃); ¹³C NMR (100 MHz, CDCl₃) δ 158.7, 153.4, 151.0, 135.3, 134.1, 117.2, 117.1, 85.0, 83.8, 78.7, 70.2, 63.3, 38.2, 26.1, 18.5, −5.1, −5.3; HRMS (FAB+) calcd for C₁₉H₃₂O₄N₅Si (M+H⁺): 422.2224, found: 422.2209.

3'-O-Allyl-2'-deoxyguanosine (64). The procedure was similar to the synthesis of 20 and the crude product was purified by flash column chromatography using CH₃OH—CH₂Cl₂ (1:10) as the eluent to afford 64 as white solid (434 mg; 90% yield): ¹H NMR (400 MHz, CD₃OD) δ 7.94 (s, 1H, 8-H), 6.22 (dd, J=5.9, 8.4 Hz, 1H, 1'-H), 5.90-6.00 (m, 1H, CH₂CH=CH₂), 5.29-5.36 (dm, J=17.2 Hz, 1H, one of CH₂CH=CH₂), 5.17-5.21 (dm, J=10.5 Hz, 1H, one of CH₂CH=CH₂), 4.31 (m, 1H, 3'-H), 4.14 (m, 1H, 4'-H), 2-Amino-6-chloro-9-[β-D-5'-O-(tert-butyldimethylsilyl)-2'-deoxyribofuranosyl] purine (61). The procedure was similar to the synthesis of 18, and the crude product was purified 4.03-4.13 (m, 2H, CH$_2$CH=CH$_2$), 3.80 (dd, J=3.8, 12.0 Hz, 1H, one of 5'-H), 3.72 (dd, J=3.7, 12.0 Hz, 1H, one of 5'-H), 2.63-2.71 (ddd, J=5.9, 8.4, 13.6 Hz, 1H, one of 2'-H), 2.45-2.52 (ddd, J=2.1, 5.9, 13.6 Hz, 1H, one of 2'-H); $^{13}$C NMR (100 MHz, DMSO-d6) δ 156.4, 153.4, 150.6, 135.1, 134.8, 116.5, 116.3, 84.9, 82.6, 79.1, 69.0, 61.8, 36.4; HRMS (FAB+) calcd for C$_{13}$H$_{18}$O$_4$N$_5$ (M+H$^+$): 308.1359, found: 308.1358.

3'-O-Allyl-2'-deoxyguanosine-5'-triphosphate (65). The procedure was similar to the synthesis of 51 to yield 65 as colorless syrup: $^1$H NMR (300 MHz, D$_2$O) δ 7.90 (s, 1H, 8-H), 6.21 (dd, J=6.1, 8.1 Hz, 1H, 1'-H), 5.86-5.96 (m, 1H, CH$_2$CH=CH$_2$), 5.27-5.35 (m, 1H, one of CH$_2$CH=CH$_2$), 5.15-5.20 (m, 1H, one of CH$_2$CH=CH$_2$), 4.30 (m, 1H, 3'-H), 4.15 (m, 1H, 4'-H), 4.02-4.14 (m, 2H, CH$_2$CH=CH$_2$), 3.75-3.85 (m, 2H, 5'-H), 2.60-2.73 (m, 1H, one of 2'-H), 2.42-2.50 (m, 1H, one of 2'-H); $^{31}$P NMR (121.4 MHz, D$_2$O) δ −10.9 (d, J=18.9 Hz, 1P, γ-P), −11.3 (d, J=19.6 Hz, 1P, α-P), −22.9 (t, J=19.6 Hz, 1P, β-P).

III. Construction of a Chip with Immobilized Self-priming DNA Template

The DNA chip was constructed as shown in FIG. 5 and involved the following three steps:

Synthesis of the alkyne-functionalized DNA template. The 5'-amino-hairpin DNA templates (GeneLink, NY) 5'-NH$_2$-TTT-TTG-TTT-TTT-TTT-TCG-ATC-GAC-TTA-AGG-CGC-TTG-CGC-CTT-AAG-TCG-3' (SEQ ID NO:3) and 5'-NH$_2$-AGT-CAG-TCT-CTC-ATC-TCG-ACA-TCT-ACG-CTA-CTC-GTC-GAT-CGG-AAA-CAG-CTA-TGA-CCA-TGC-TTG-CAT-GGT-CAT-AGC-TGT-TTC-C-3' (SEQ ID NO:4) were coupled with 6-heptynoic acid by adding 300 μL DMSO solution of 6-heptynoic-NHS ester [succinimidyl N-(6-heptynoate)] (0.8 M) into the 1000 μL DNA template solution (200 μM, in 0.25 M Na$_2$CO$_3$/NaHCO$_3$ buffer, pH 9.0). The reaction mixture was stirred for 5 h at room temperature to produce a terminal alkynyl group on the 5'-end of the hairpin DNA. The resulting alkyne-functionalized DNA was separated from the excess reagent by size-exclusion chromatography using PD-10 columns (GE Health, NJ). Further desalting with an oligonucleotide purification cartridge (Applied Biosystems, CA) and drying afforded the crude product which was further purified by reverse-phase HPLC (Waters HPLC system containing Waters Delta 600 controller, Rheodyne 77251 injector and 2996 photodiode array detector, Milford, MA) using a C-18 reverse column (Xterra MS C18, 4.6 mm×50 mm, 2.5 μm) at a flow rate of 0.5 mL/min, with detection at 260 nm, and elution with a linear gradient of 12-34.5% of B in A over 40 min (A: 4.4 mM triethylamine and 100 mM hexafluoroisopropyl alcohol aqueous solution, pH 8.1; B: methanol). The fractions containing the desired product were collected and evaporated to dryness under vacuum. MALDI-TOF MS was used to characterize the product on a Voyager DE matrix assisted laser spectrometer (Applied Biosystems, CA) using 3-hydroxypicolinic acid as a matrix.

Azide functionalization of an amine-modified glass surface. The amine-modified glass slide (Corning® GAPS II) was cleaned and pre-treated by immersion into a basic solution [N,N-diisopropyl ethylamine (DIPEA)/dimethylformamide (DMF), 1:9 (V/V)] for 30 min. The glass slide was then washed with DMF, and transferred into the 2 mL DMF coupling solution containing 100 mM O-(2-azidoethyl)-O'-[2-(diglycolyl-amino)-ethyl]heptaethylene glycol (Fluka, Switzerland), Benzotriazole-1-yl-oxy-tris-pyrrolidino-phosphonium hexafluorophosphate (PyBOP) (Novabiochem, CA) and 200 mM DIPEA. The reaction vessel was gently shaken for 4 h at room temperature. The azide functionalized glass slide was washed thoroughly with DMF and ethanol, and then dried under argon gas stream.

DNA immobilization on the azide-modified glass surface using 1,3-dipolar alkyne-azide cycloaddition chemistry. A coupling mixture was prepared by mixing tetrakis-(acetonitrile)copper (I) hexafluorophosphate (2 mM/DMSO), tris-(benzyltriazolylmethyl) amine (TBTA) (2 mM/DMSO), sodium ascorbate (2.6 mM/H$_2$O) and alkynyl DNA (50 μM/H$_2$O) with a volumetric ratio of 3:3:2.3:3. This coupling mixture was then spotted onto the azide-functionalized glass slide in the form of 11.0 μL drops with the aid of adhesive silicone isolators (Grace Bio-Labs, OR) to create uniform spots on the glass surface. The DNA spotted glass slide was incubated in a humid chamber at room temperature for 8 h, then washed with de-ionized water and SPSC buffer (50 mM sodium phosphate/1 M NaCl, pH 7.5) for ½ h to remove non-specifically bound DNA, and finally rinsed with dH$_2$O. The formation of a stable hairpin was ascertained by covering the DNA spots with 1× Thermolpol II reaction buffer (10 mM KCl, 10 mM (NH$_4$)$_2$SO$_4$, 20 mM Tris-HCl, 0.1% Triton X-100, 4 mM MnCl$_2$, pH 8.8), incubating it in a humid chamber at 95° C. for 5 min to dissociate any partial hairpin structure, and then cooling slowly for re-annealing.

IV. Continuous DNA Polymerase Reaction Using Four Chemically Cleavable Fluorescent Nucleotides as Reversible Terminators in Solution We characterized the four nucleotide analogues 3'-O-allyl-dCTP-allyl-Bodipy-FL-510, 3'-O-allyl-dUTP-allyl-R6G, 3'-O-allyl-dATP-allyl-ROX and 3'-O-allyl-dGTP-allyl-Bodipy-650, by performing four continuous DNA-extension reactions sequentially using a primer (5'-AGAGGATCCAACCGAGAC-3', SEQ ID NO:5) and a synthetic DNA template (5'-GTGTACATCAACATCACC-TACCACCATGTCAGTCTCGGTTGGATCCTCTATTGT GTCCGG-3', SEQ ID NO:6) based on a portion of exon 7 of the human p53 gene. The four nucleotides in the template immediately adjacent to the annealing site of the primer are 3'-ACTG-5'. First, a polymerase extension reaction using a pool of all four nucleotide analogues along with the primer and the template was performed producing a single base extension product. The reaction mixture for this, and all subsequent extension reactions, consisted of 80 pmol of template, 50 pmol of primer, 100 pmol of 3'-O-allyl-dNTPs-allyl-fluorophore, 1× Thermopol II reaction buffer, 40 nmol of Mn$^{2+}$ and 2 U of 9°N mutant DNA polymerase (exo-) A485L/Y409V in a total volume of 20 μL. The reaction consisted of 20 cycles at 94° C. for 20 sec, 48° C. for 40 sec, and 62° C. for 90 sec. Subsequently, the extension product was purified by using reverse-phase HPLC. The fraction containing the desired DNA product was collected and freeze-dried for analysis using MALDI-TOF mass spectrometry. For deallylation, the purified DNA extension product bearing the fluorescent nucleotide analogue was resuspended in degassed water and added to a deallylation cocktail [1× Thermopol I reaction buffer/Na$_2$PdCl$_4$/P (PhSO$_3$Na)$_3$] and incubated for 30 s to yield deallylated DNA product which was characterized by MALDI-TOF MS. The DNA product with both the fluorophore and the 3'-O-allyl group removed to generate a free 3'-OH group was used as a primer for a second extension reaction using 3'-O-allyl-dNTPs-allyl-fluorophore. The second extended DNA product was then purified by HPLC and deallylated.

The third and the fourth extensions were carried out in a similar manner using the previously extended and deallylated product as the primer.

V. 4-Color SBS Reaction on a Chip with Four Chemically Cleavable Fluorescent Nucleotides as Reversible Terminators Ten microliters of a solution consisting of 3'-O-allyl-dCTP-allyl-Bodipy-FL-510 (3 pmol), 3'-O-allyl-dUTP-allyl-R6G (10 pmol), 3'-O-allyl-dATP-allyl-ROX (5 pmol) and 3'-O-allyl-dGTP-allyl-Cy5 (2 pmol), 1 U of 9°N mutant DNA polymerase, and 1× Thermolpol II reaction buffer was spotted on the surface of the chip, where the self-primed DNA moiety was immobilized. The nucleotide analogue complementary to the DNA template was allowed to incorporate into the primer at 68° C. for 10 min. To synchronize any unincorporated templates, an extension solution consisting of 30 pmol each of 3'-O-allyl-dCTP, 3'-O-allyl-dTTP, 3'-O-allyl-dATP and 3'-O-allyl-dGTP, 1 U of 9°N mutant DNA polymerase, and 1× Thermolpol II reaction buffer was spotted on the same spot and incubated at 68° C. for 10 min. After washing the chip with a SPSC buffer containing 0.1% Tween 20 for 5 min, the surface was rinsed with $dH_2O$, dried briefly and then scanned with a 4-color ScanArray Express scanner (Perkin-Elmer Life Sciences) to detect the fluorescence signal. The 4-color scanner is equipped with four lasers with excitation wavelengths of 488, 543, 594, and 633 nm and emission filters centered at 522, 570, 614, and 670 nm. For deallylation, the chip was immersed in a deallylation cocktail [1× Thermolpol I reaction buffer/$Na_2PdCl_4$/$P(PhSO_3Na)_3$] and incubated for 5 min at 60° C. The chip was then immediately immersed in a 3 M Tris-HCl buffer (pH 8.5) and incubated for 5 min at 60° C. Finally, the chip was rinsed with acetonitrile/$dH_2O$ (1:1, V/V) and $dH_2O$. The chip surface was scanned again to compare the intensity of fluorescence after deallylation with the original fluorescence intensity. This process was followed by the next polymerase extension reaction using 3'-O-allyl-dNTPs-allyl-fluorophore and 3'-O-allyl-dNTPs, with the subsequent washing, fluorescence detection, and deallylation processes performed as described above. The same cycle was repeated multiple times using the four chemically cleavable fluorescent nucleotide mixture in polymerase extension reaction to obtain de novo DNA sequencing data on various different DNA templates.

REFERENCES

1. Collins, F. S., Green, E. D., Guttmacher, A. E. & Guyer, M. S. (2003) *Nature* 422, 835-847.
2. Smith, L. M., Sanders, J. Z., Kaiser, R. J., Hughes, P., Dodd, C., Connell, C. R., Heiner, C., Kent, S. B. & Hood, L. E. (1986) *Nature* 321, 674-679.
3. Prober, J. M., Trainor, G. L., Dam, R. J., Hobbs, F. W., Robertson, C. W., Zagursky, R. J., Cocuzza, A. J., Jensen, M. A. & Baumeister, K. (1987) *Science* 238, 336-341.
4. Ju, J., Ruan, C., Fuller, C. W., Glazer, A. N. & Mathies, R. A. (1995) *Proc. Natl. Acad. Sci. USA* 92, 4347-4351.
5. Kan, C. W., Doherty, E. A. & Barron, A. E. (2003) *Electrophoresis* 24, 4161-4169.
6. Drmanac, S., Kita, D., Labat, I., Hauser, B., Schmidt, C., Burczak, J. D. & Drmanac, R. (1998) *Nat. Biotechnol.* 16, 54-58.
7. Fu, D. J., Tang, K., Braun, A., Reuter, D., Darnhofer-Demar, B., Little, D. P., O'Donnell, M. J., Cantor, C. R. & Koster, H. (1998) *Nat. Biotechnol.* 16, 381-384.
8. Roskey, M. T., Juhasz, P., Smirnov, I. P., Takach, E. J., Martin, S. A. & Haff, L. A. (1996) *Proc. Natl. Acad. Sci. USA* 93, 4724-4729.
9. Edwards, J. R., Itagaki, Y. & Ju, J. (2001) *Nucleic Acids Res.* 29, E104-4.
10. Kasianowicz, J. J., Brandin, E., Branton, D. & Deamer, D. W. (1996) *Proc. Natl. Acad. Sci. USA* 93, 13770-13773.
11. Shendure, J., Porreca, G. J., Reppas, N. B., Lin, X., McCutcheon, J. P., Rosenbaum, A. M., Wang, M. D., Zhang, K., Mitra, R. D. & Church, G. M. (2005) *Science* 309, 1728-1732.
12. Ronaghi, M., Uhlen, M. & Nyren, P. (1998) *Science* 281, 363-365.
13. Braslavsky, I., Hebert, B., Kartalov, E. & Quake, S. R. (2003) *Proc. Natl. Acad. Sci. USA* 100, 3960-3964.
14. Mitra, R. D., Shendure, J., Olejnik, J., Edyta Krzymanska, O. & Church, G. M. (2003) *Anal. Biochem.* 320, 55-65.
15. Hyman, E. D. (1988) *Anal. Biochem.* 174, 423-436.
16. Margulies, M., Egholm, M., Altman, W. E., Attiya, S., Bader, J. S., Bemben, L. A., Berka, J., Braverman, M. S., Chen, Y.-J., Chen, Z., et. al. (2005) *Nature* 437, 376-380.
17. Cheeseman, P. C. (1994) U.S. Pat. No. 5,302,509.
18. Metzker, M. L., Raghavachari, R., Richards, S., Jacutin, S. E., Civitello, A., Burgess, K. & Gibbs, R. A. (1994) *Nucleic Acids Res.* 22, 4259-4267.
19. Welch, M. B. & Burgess, K. (1999) *Nucleosides Nucleotides* 18, 197-201.
20. Lu, G. & Burgess, K. (2006) *Bioorg. Med. Chem. Lett.* 16, 3902-3905.
21. Metzker, M. L. (2005) *Genome Res.* 15, 1767-1776.
22. Pelletier, H., Sawaya, M. R., Kumar, A., Wilson, S. H. & Kraut, J. (1994) *Science* 264, 1891-1903.
23. Rosenblum, B. B., Lee, L. G., Spurgeon, S. L., Khan, S. H., Menchen, S. M., Heiner, C. R. & Chen, S. M. (1997) *Nucleic Acids Res.* 25, 4500-4504.
24. Zhu, Z., Chao, J., Yu, H. & Waggoner, A. S. (1994) *Nucleic Acids Res.* 22, 3418-3422.
25. Ju, J., Li, Z., Edwards, J. & Itagaki, Y. (2003) U.S. Pat. No. 6,664,079.
26. Seo, T. S., Bai, X., Kim, D. H., Meng, Q., Shi, S., Ruparel, H., Li, Z., Turro, N. J. & Ju, J. (2005) *Proc. Natl. Acad. Sci. USA* 102, 5926-31.
27. Bi, L., Kim, D. H. & Ju, J. (2006) *J. Am. Chem. Soc.* 128, 2542-2543.
28. Ruparel, H., Bi, L., Li, Z., Bai, X., Kim, D. H., Turro, N. J. & Ju, J. (2005) *Proc. Natl. Acad. Sci. USA* 102, 5932-5937.
29. Meng, Q., Kim, D. H., Bai, X., Bi, L., Turro, N. J. & Ju, J. (2006) *J. Org. Chem.* 71, 3248-3252.
30. Barnes, C., Balasubramanian, S., Liu, X., Swerdlow, H., Milton, J. (2006) U.S. Pat. No. 7,057,026.

What is claimed is:

1. A plurality of different deoxyribonucleic acids covalently immobilized on a solid support, wherein at least one of the plurality different deoxyribonucleic acids comprises a polymerase-incorporated labeled nucleotide analogue derived from the group consisting of labeled nucleotide analogues A-D, and wherein at least one of the plurality of different deoxyribonucleic acids comprises a polymerase-incorporated un-labeled nucleotide analogue derived from the group consisting of un-labeled nucleotide analogues A'-D'

(A)

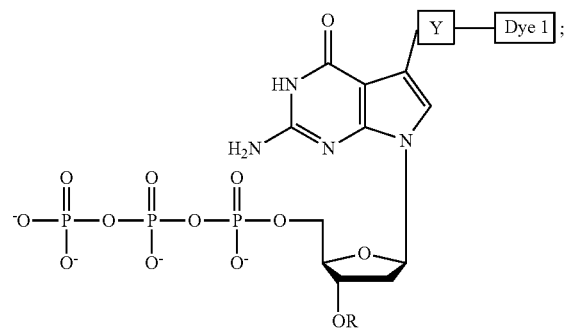

(B)

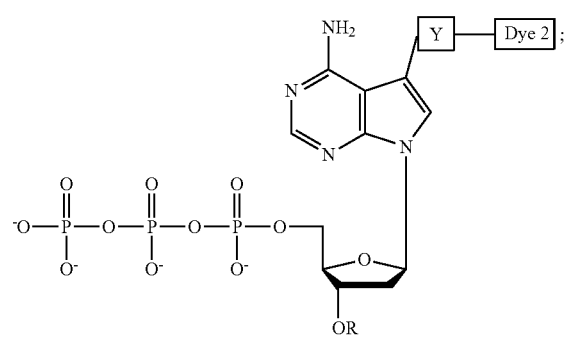

(C)

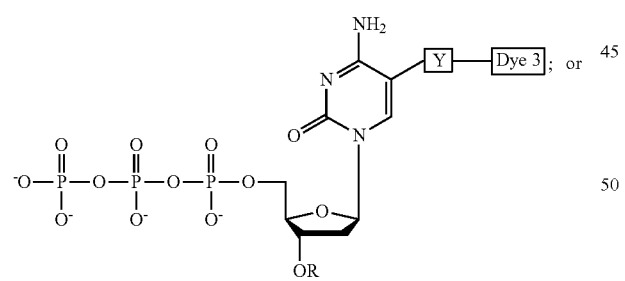

(D)

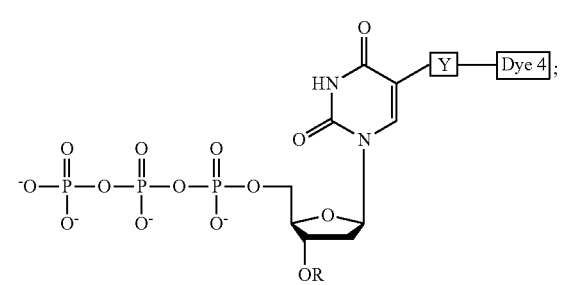

(A')

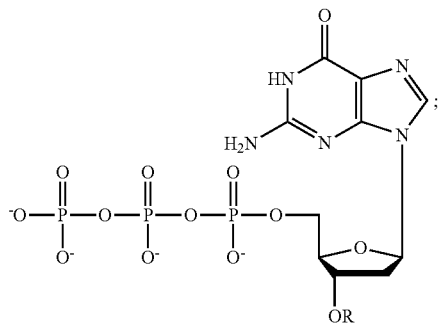

(B')

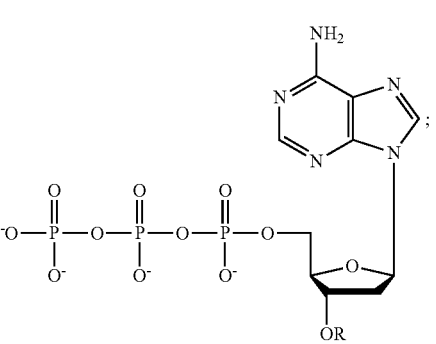

(C')

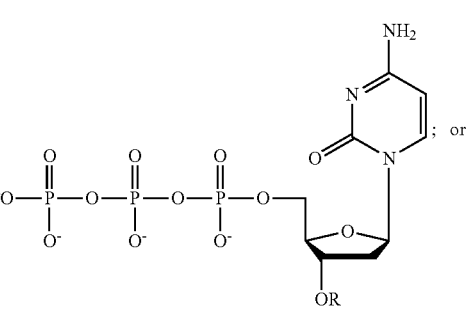

(D')

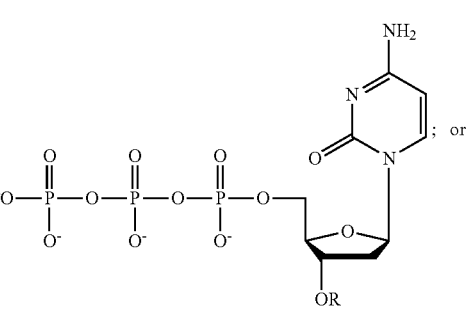

wherein R (a) represents a cleavable, chemical group capping the oxygen at the 3' position of the deoxyribose of the deoxyribonucleotide analogue, (b) does not interfere with recognition of the analogue as a substrate by the DNA polymerase or with incorporation of the analogue into the growing DNA strand during the DNA polymerase reaction, and (c) is stable during the DNA polymerase reaction;

wherein the covalent bona between the 3'-oxygen and R is stable during the DNA polymerase reaction;

wherein each of Dye 1, Dye 2, Dye 3 and Dye 4 represents a distinguishable, detectable moiety;

wherein (i) the nucleotide analogue is incorporated into the growing DNA strand as a result of the DNA polymerase reaction, (ii) the incorporated analogue is identified, and (iii) the covalent bond between the 3'-oxygen and R is cleaved under conditions compatible with DNA sequencing to allow the incorporation and detection of the next nucleotide analogue;

wherein Y represents a cleavable, chemical linker which (a) does not interfere with recognition of the analogue as a substrate by the DNA polymerase or with incorporation of the analogue into the growing DNA strand during the DNA polymerase reaction and (b) is stable during the DNA polymerase reaction;

wherein the nucleotide analogue:
  i) is recognized as a substrate by the DNA polymerase for incorporation into the growing' DNA strand during the DNA polymerase reaction,
  ii) is efficiently and accurately incorporated at the end of the growing DNA strand during the DNA polymerase reaction,
  iii) produces a 3'—OH group on the deoxyribose upon cleavage of R under conditions compatible with DNA sequencing, and
  iv) no longer includes a detectable moiety on the base upon cleavage of Y under conditions compatible with DNA sequencing;

and wherein if the nucleotide analogue is: (A) or (A'), it forms hydrogen bonds with cytosine or a cytosine nucleotide analogue; (B) or (B'), it forms hydrogen bonds with thymine or a thymine nucleotide analogue; (C) or (C'), it forms hydrogen bonds with guanine or a guanine nucleotide analogue, or (D) or (D'), it forms hydrogen bonds with adenine or an adenine nucleotide analogue.

2. The plurality of different deoxyribonucleic acids of claim 1, wherein the polymerase-incorporated labeled nucleotide analogue is derived from A and the polymerase-incorporated un-labeled nucleotide analogue is derived from A'.

3. The plurality of different deoxyribonucleic acids of claim 1, wherein the polymerase-incorporated labeled nucleotide analogue is derived from B and the polymerase-incorporated un-labeled nucleotide analogue is derived from B'.

4. The plurality of different deoxyribonucleic acids of claim 1, wherein the polymerase-incorporated labeled nucleotide analogue is derived from C and the polymerase-incorporated un-labeled nucleotide analogue is derived from C'.

5. The plurality of different deoxyribonucleic acids of claim 1, wherein the polymerase-incorporated labeled nucleotide analogue is derived from D and the polymerase-incorporated un-labeled nucleotide analogue is derived from D'.

* * * * *

UNITED STATES PATENT AND TRADEMARK OFFICE
CERTIFICATE OF CORRECTION

PATENT NO. : 11,939,631 B2
APPLICATION NO. : 17/405341
DATED : March 26, 2024
INVENTOR(S) : Jingyue Ju et al.

It is certified that error appears in the above-identified patent and that said Letters Patent is hereby corrected as shown below:

On the Title Page

In the ABSTRACT Item (57), please replace:
"This invention provides a process for sequencing single-stranded DNA by employing a nanopore and modified nucleotides."

With:
--This invention provides a process for sequencing single-stranded DNA by employing modified nucleotides.--

Signed and Sealed this
Thirtieth Day of April, 2024

Katherine Kelly Vidal
*Director of the United States Patent and Trademark Office*